(12) United States Patent
Chen

(10) Patent No.: US 7,799,521 B2
(45) Date of Patent: *Sep. 21, 2010

(54) THERMAL CYCLING

(75) Inventor: Shuqi Chen, Brookline, MA (US)

(73) Assignee: Chen & Chen, LLC, Framingham, MA (US)

( * ) Notice: Subject to any disclaimer, the term of this patent is extended or adjusted under 35 U.S.C. 154(b) by 1300 days.

This patent is subject to a terminal disclaimer.

(21) Appl. No.: 10/241,816

(22) Filed: Sep. 11, 2002

(65) Prior Publication Data

US 2003/0049833 A1    Mar. 13, 2003

Related U.S. Application Data

(63) Continuation-in-part of application No. 09/782,732, filed on Feb. 13, 2001, now Pat. No. 6,780,617, and a continuation-in-part of application No. 09/910,233, filed on Jul. 20, 2001, now Pat. No. 6,748,332, which is a continuation of application No. 09/339,056, filed on Jun. 23, 1999, now Pat. No. 6,318,191.

(60) Provisional application No. 60/259,025, filed on Dec. 29, 2000, provisional application No. 60/090,471, filed on Jun. 24, 1998, provisional application No. 60/318,768, filed on Sep. 11, 2001.

(51) Int. Cl.
*C12Q 1/68* (2006.01)
*C12M 1/34* (2006.01)

(52) U.S. Cl. .............. 435/6; 435/91.2; 435/286.5; 435/287.2; 435/287.3; 435/288.5; 435/288.7; 435/303.1

(58) Field of Classification Search .............. 435/303.1, 435/286.7, 286.5
See application file for complete search history.

(56) References Cited

U.S. PATENT DOCUMENTS

| | | | |
|---|---|---|---|
| 3,036,894 A | 5/1962 | Forestiere | |
| 3,441,205 A | 4/1969 | Young, Jr. | .................... 233/26 |
| 3,556,731 A | 1/1971 | Martin | |
| 3,579,303 A | 5/1971 | Pickering | |
| 3,607,097 A | 9/1971 | Auphan et al. | |

(Continued)

FOREIGN PATENT DOCUMENTS

DE    2 007 405    10/1970

(Continued)

OTHER PUBLICATIONS

Findlay et al., "Automated Closed-Vessel System . . .", Nov. 9, 1993, pp. 1927-1933.*

(Continued)

*Primary Examiner*—William H Beisner
(74) *Attorney, Agent, or Firm*—Scott E. Kamholz; Foley Hoag LLP

(57) ABSTRACT

A device for processing a biological sample includes a processing unit having at least one opening to receive a sample vessel and a plurality of processing stations positioned along the opening. The processing stations each have a compression member adapted to compress the sample vessel within the opening and thereby move a substance within the sample vessel among the processing stations. An energy transfer element can be coupled to one or more of the processing stations for transferring thermal energy to the content at a processing station.

94 Claims, 22 Drawing Sheets

U.S. PATENT DOCUMENTS

| | | | |
|---|---|---|---|
| 3,620,678 A | 11/1971 | Gulgan et al. | |
| 3,698,822 A | 10/1972 | Polanyi | |
| 3,819,158 A * | 6/1974 | Sharpe et al. | 366/349 |
| 3,888,629 A | 6/1975 | Bagshawe | |
| 3,918,913 A | 11/1975 | Stevenson et al. | |
| 4,038,030 A * | 7/1977 | Albright et al. | 436/165 |
| 4,065,263 A | 12/1977 | Woodbridge, III | 23/253 |
| 4,166,457 A | 9/1979 | Jacobsen et al. | |
| 4,187,861 A | 2/1980 | Heffernan | 128/764 |
| 4,267,149 A | 5/1981 | Bruckner et al. | |
| 4,329,698 A | 5/1982 | Smith | |
| 4,426,451 A | 1/1984 | Columbus | |
| 4,430,139 A | 2/1984 | Baverstock | |
| 4,446,232 A | 5/1984 | Liotta | |
| 4,472,498 A | 9/1984 | Masuda et al. | |
| 4,596,271 A | 6/1986 | Brundage | |
| 4,608,275 A | 8/1986 | Kukanskis et al. | |
| 4,695,430 A | 9/1987 | Coville et al. | |
| 4,752,449 A | 6/1988 | Jackson et al. | |
| 4,803,154 A | 2/1989 | Uo et al. | |
| 4,820,297 A | 4/1989 | Kaufman et al. | |
| 4,822,568 A | 4/1989 | Tomita et al. | |
| 4,846,005 A | 7/1989 | Bacehowski et al. | |
| 4,900,321 A | 2/1990 | Kaufman et al. | |
| 4,917,864 A | 4/1990 | Marsoner et al. | |
| 5,019,348 A | 5/1991 | Ohms et al. | |
| 5,057,438 A | 10/1991 | Imai et al. | |
| 5,061,445 A | 10/1991 | Zoski et al. | |
| 5,073,484 A | 12/1991 | Swanson et al. | |
| 5,087,425 A | 2/1992 | Flossdorf et al. | |
| 5,089,233 A | 2/1992 | DeVaney, Jr. et al. | 422/99 |
| 5,098,660 A | 3/1992 | Devaney, Jr. | |
| 5,120,662 A | 6/1992 | Chan et al. | |
| 5,143,084 A | 9/1992 | Macemon et al. | |
| 5,176,203 A | 1/1993 | Larzul | |
| 5,178,832 A | 1/1993 | Phillips et al. | |
| 5,187,084 A | 2/1993 | Hallsby | |
| 5,229,297 A | 7/1993 | Schnipelsky et al. | |
| 5,244,813 A | 9/1993 | Walt et al. | |
| 5,270,183 A | 12/1993 | Corbett et al. | |
| 5,356,785 A | 10/1994 | McMahon et al. | |
| 5,374,395 A | 12/1994 | Robinson et al. | |
| 5,380,665 A | 1/1995 | Cusack et al. | |
| 5,391,478 A | 2/1995 | Greene et al. | |
| 5,422,271 A | 6/1995 | Chen et al. | |
| 5,424,220 A | 6/1995 | Goerlach-Graw et al. | |
| 5,430,957 A | 7/1995 | Eigen et al. | |
| 5,455,175 A | 10/1995 | Wittwer et al. | |
| 5,460,780 A | 10/1995 | DeVaney, Jr. et al. | 422/99 |
| 5,475,610 A | 12/1995 | Atwood et al. | |
| 5,491,067 A | 2/1996 | Setcavage et al. | |
| 5,504,007 A | 4/1996 | Haynes | |
| 5,508,197 A | 4/1996 | Hansen et al. | |
| 5,567,617 A | 10/1996 | Caprio et al. | 435/287.2 |
| 5,571,410 A | 11/1996 | Swedberg et al. | 210/198.2 |
| 5,576,218 A | 11/1996 | Zurek et al. | |
| 5,591,573 A | 1/1997 | Whalen et al. | |
| 5,602,756 A | 2/1997 | Atwood et al. | |
| 5,626,732 A | 5/1997 | Allington | |
| 5,631,683 A | 5/1997 | Nishioka et al. | |
| 5,656,501 A | 8/1997 | Yedgar et al. | |
| 5,668,330 A | 9/1997 | Bartlett-Hooker et al. | |
| 5,709,668 A | 1/1998 | Wacks | |
| 5,714,380 A | 2/1998 | Neri et al. | |
| 5,735,824 A | 4/1998 | Hjertman | |
| 5,736,106 A | 4/1998 | Ishiguro et al. | |
| 5,780,222 A | 7/1998 | Peddada et al. | |
| 5,795,547 A | 8/1998 | Moser et al. | |
| 5,801,052 A | 9/1998 | Bartlett-Hooker et al. | |
| 5,810,778 A | 9/1998 | Hjertman | |
| 5,827,480 A | 10/1998 | Haff et al. | |
| 5,830,411 A | 11/1998 | Marinell Gisper-Sauch | |
| 5,847,734 A | 12/1998 | Pawlowski, Jr. | |
| 5,863,502 A | 1/1999 | Southgate et al. | |
| 5,866,366 A | 2/1999 | Kallender | |
| 5,897,842 A | 4/1999 | Dunn et al. | |
| 5,942,432 A | 8/1999 | Smith et al. | |
| 5,985,651 A | 11/1999 | Hunicke-Smith | |
| 6,016,683 A | 1/2000 | Betts et al. | 73/1.03 |
| 6,019,945 A | 2/2000 | Ohishi et al. | |
| 6,033,880 A | 3/2000 | Haff et al. | |
| 6,066,296 A | 5/2000 | Brady et al. | |
| 6,159,727 A | 12/2000 | Bochkariov | |
| 6,163,714 A | 12/2000 | Stanley et al. | |
| 6,174,670 B1 | 1/2001 | Wittwer et al. | |
| 6,186,982 B1 | 2/2001 | Gross et al. | |
| 6,194,160 B1 | 2/2001 | Levin | |
| 6,210,369 B1 | 4/2001 | Wilmot et al. | |
| 6,210,958 B1 * | 4/2001 | Brust et al. | 435/287.2 |
| 6,251,660 B1 | 6/2001 | Muir et al. | |
| 6,264,892 B1 | 7/2001 | Kaltenbach et al. | 422/68.1 |
| 6,274,726 B1 | 8/2001 | Laugharn, Jr. et al. | 536/25.4 |
| 6,299,601 B1 | 10/2001 | Hjertman | |
| 6,303,083 B1 | 10/2001 | Johnson et al. | |
| 6,318,191 B1 | 11/2001 | Chen | 73/863.11 |
| 6,439,759 B1 * | 8/2002 | Ray et al. | 366/197 |
| 6,440,725 B1 | 8/2002 | Purahmadi et al. | |
| 6,748,332 B2 | 6/2004 | Chen | 702/19 |
| 6,780,617 B2 | 8/2004 | Chen | 435/91.2 |
| 2004/0105782 A1 | 6/2004 | Chen | 422/60 |
| 2004/0161788 A1 | 8/2004 | Chen et al. | 435/6 |
| 2004/0209331 A1 * | 10/2004 | Ririe | 435/91.2 |
| 2004/0223878 A1 | 11/2004 | Chen | 422/68.1 |
| 2005/0019875 A1 | 1/2005 | Chen | 435/91.2 |

FOREIGN PATENT DOCUMENTS

| | | |
|---|---|---|
| DE | 27 53 865 | 6/1979 |
| EP | 0 047806 | 3/1982 |
| EP | 0139373 | 5/1985 |
| EP | 0312394 | 4/1989 |
| EP | 0435380 A2 | 7/1991 |
| EP | 0435380 A3 | 7/1991 |
| EP | 0488769 A2 | 11/1991 |
| EP | 0504772 A2 | 9/1992 |
| EP | 0739241 B1 | 8/1998 |
| EP | 0955097 A1 | 11/1999 |
| EP | 1000661 A1 | 5/2000 |
| EP | 1 106 250 A2 | 6/2001 |
| FR | 1 513 306 | 5/1968 |
| FR | 2 590 673 | 5/1987 |
| FR | 2 672 231 | 8/1992 |
| WO | WO 94/20831 | 9/1994 |
| WO | WO 97/27324 | 7/1997 |
| WO | WO 97/40939 | 11/1997 |
| WO | WO 97/48818 | 12/1997 |
| WO | WO-9809728 | 3/1998 |
| WO | WO-9816313 | 4/1998 |
| WO | WO 98/43740 | 10/1998 |
| WO | WO 98/50147 | 11/1998 |
| WO | WO 99/26724 | 6/1999 |
| WO | WO 99/67646 | 12/1999 |
| WO | WO 00/13014 | 3/2000 |
| WO | WO 00/25920 | 5/2000 |

OTHER PUBLICATIONS

Partial International Search Report Mailed on Jul. 8, 2003.

Rasmussen, et al. "Quantitative PCR by Continuous Fluorescense Monitoring of a Double Strand DNA Specific Binding Dye," Biochemica, No. 2 (1998), pp. 8-11.

Wittwer, et al. "Minimizing the Time Required for DNA Amplification by Efficient Heat Transfer to Small Samples," Anal Biochem 1990, 186:328-331.

Schober, et al. "Multichannel PCR and Serial Transfer Machine as a Future Tool in Evolutionary Biotechnology," Biotechinques 1995, 18:652-661.

Kopp, et al. "Chemical Amplification: Continuous-Flow PCR on a Chip," Science, vol. 280, May 15, 1998.

Chen, et al., "Rolling and transient tethering of leukocytes on antibodies reveal specializations of selectins," Proc. Natl. Acad. Sci. USA 94:3172-3177(1997).

Taylor, et al., "Enhanced Human Red Blood Cell Aggregation While Diving," Naval Medical Research Institute, Bethesda, MD and Dept. of Biochemistry, Hebrew University-Hadasseh Medical School, Jerusalem, Israel (1997).

World Wide Web Page, *Quantitation of DNA/RNA Using Real-time PCR Detection*, www.appliedbiosystems.com/molecularbiology/about/white.htm/per/sds/ (Applied Biosystems), pp. 1-8, Oct. 31, 2000.

World Wide Web Page, *Quantitative Real-Time PCR*, www.lsc.psu.edu/stf/naf/quantitative.hun/ (PennState Life Sciences Consortium, Shared Technology Facilities), pp. 1-3, Oct. 31, 2000.

(Nalge Nunc International), World Wide Web Page, *DIAPOPS*, http://nunc.nalgenunc.com/resource/technical/nag/dp0014.htm, pp. 1-4, Oct. 31, 2000.

Boehringer Mannheim, *Lighteveler Instrument*, pp. 1-16, Jul. 1998.

Roche Molecular Biochemicals, *LightCycler System, Real-time PCR—as flexible as you are*, pp. 1-34, Jan. 2000.

Belgrader, P., et al., *PCR Detection of Bacteria in Seven Minutes*, Science 284, pp. 449-450. Apr. 16, 1999.

Intergen, *Amplifluor Universal Detection System, Versatile, Quantitative Detection for PCR in Endpoint and Real-time*.

Kenneth Mason Publications; "Simplified PCT Processor and Method", Research Disclosure, Hampshire, GB, vol. 401, pp. 651-655, (Sep. 1, 1997).

Kenneth Mason Publications; "PCR Processor", Research Disclosure, Hampshire, GB, vol. 396 pp. 207-211, (Apr. 1, 1997).

International Search Report Dated Oct. 19, 1999 regarding PCT/US99/14105 (Jun. 23, 1999).

International Search Report Completed on Jun. 27, 2002 and Mailed on Jul. 16, 2002.

Alon, et al, "The Kinetics of L-selectin Tethers and the Mechanics of Selectin-mediated Rolling,", *J. Cell Biol.*, 138 (5); 1169-1180 (1997).

Ben-Hur et al., "Photodynamic Treatment of Red Blood Cell Concentrates for Virus Inactivation Enhances Red Blood Cell Aggregation: Protection with Antioxidants," *Photochem. and Photobiol.*, 66(4):509-512 (1997).

Chen et al, "Monitoring of Red Blood Cell Aggregability in a Flow-Chamber by Computerized Image Analysis," *Clin. Hemorheology*, 14(4): 497-507 (1994).

Chen, et al., "Red blood cell aggregability is enhanced by physiological levels of hydrostatic pressure", *Biochimica et Biophysica Acta 1192*, Elsevier Science B. V., 247-252 (1994).

Chen, et al., "Monitoring of Erythrocyte Aggregate Morphology Under Flow by Computerized Image Analysis," Biorheology, 32(4):498-496 (1995).

Chen, et al., "Enhanced aggregability of red blood cells of β-thalassemia major patients," Am. Physiol. Soc., H1951-1956 (1996).

* cited by examiner

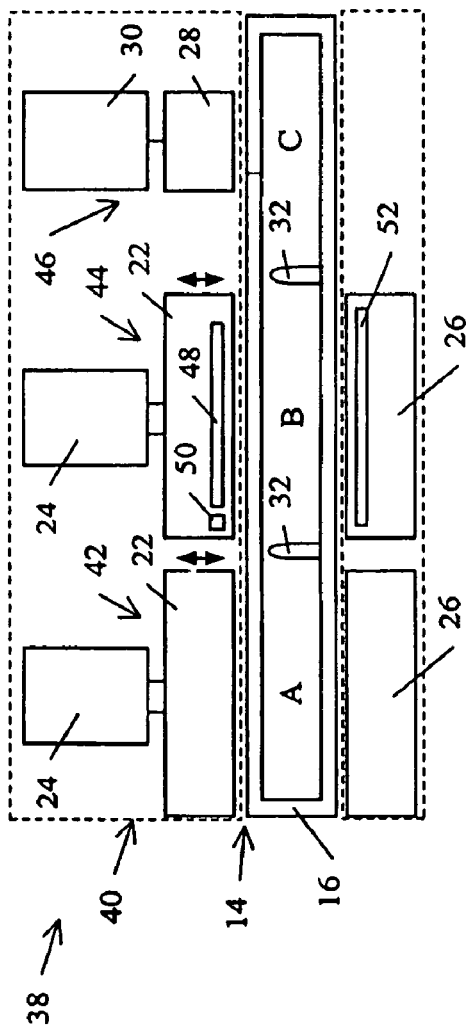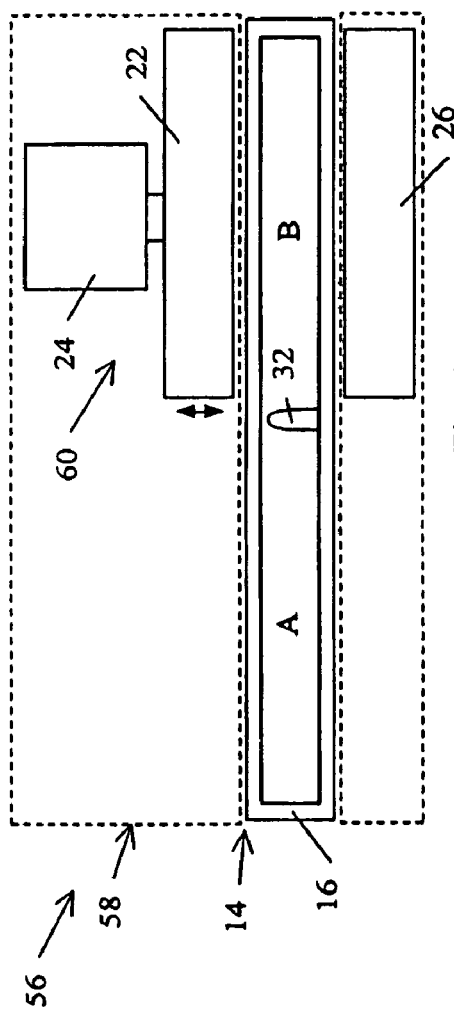

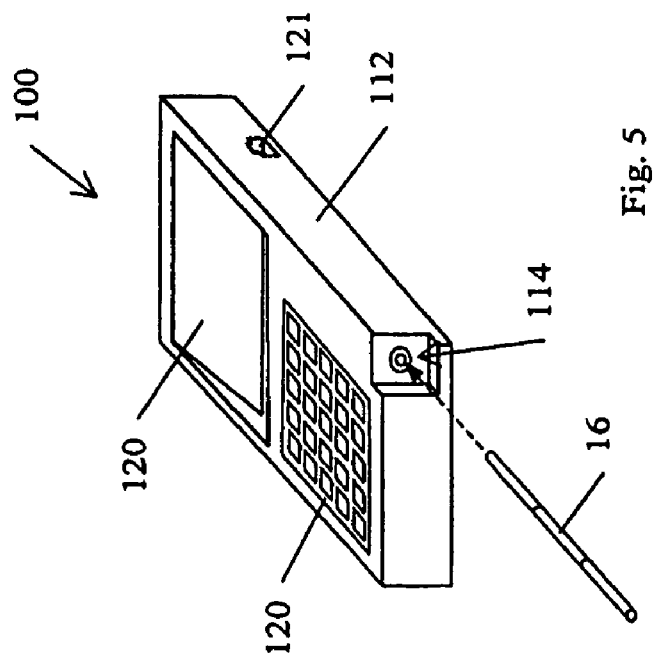
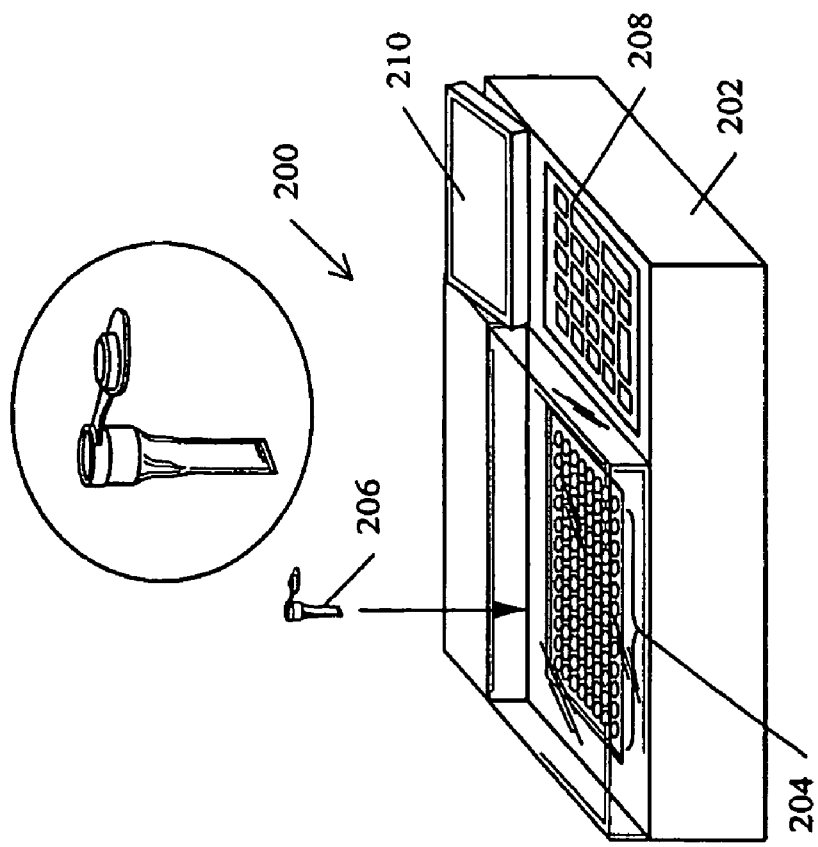
Fig. 5
Fig. 6

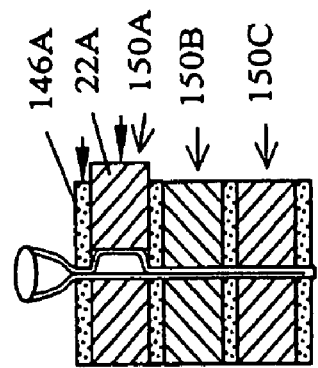
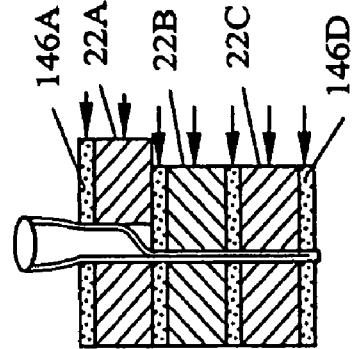
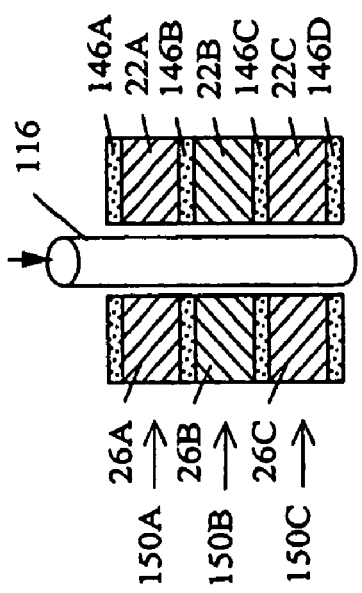
Fig. 13A
Fig. 13B
Fig. 13C
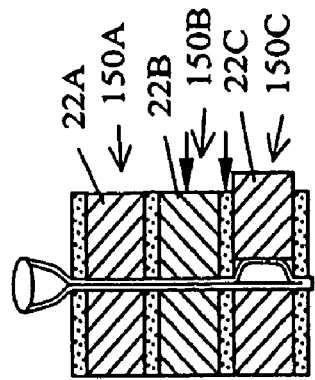
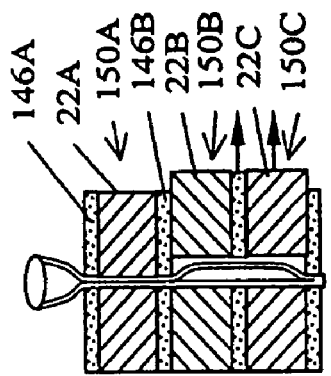
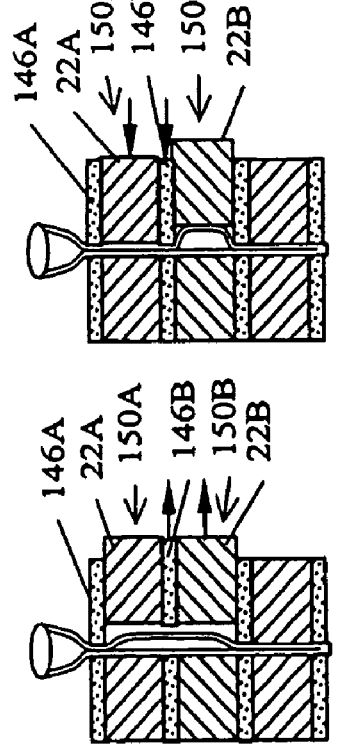
Fig. 13E
Fig. 13D
Fig. 13F
Fig. 13G

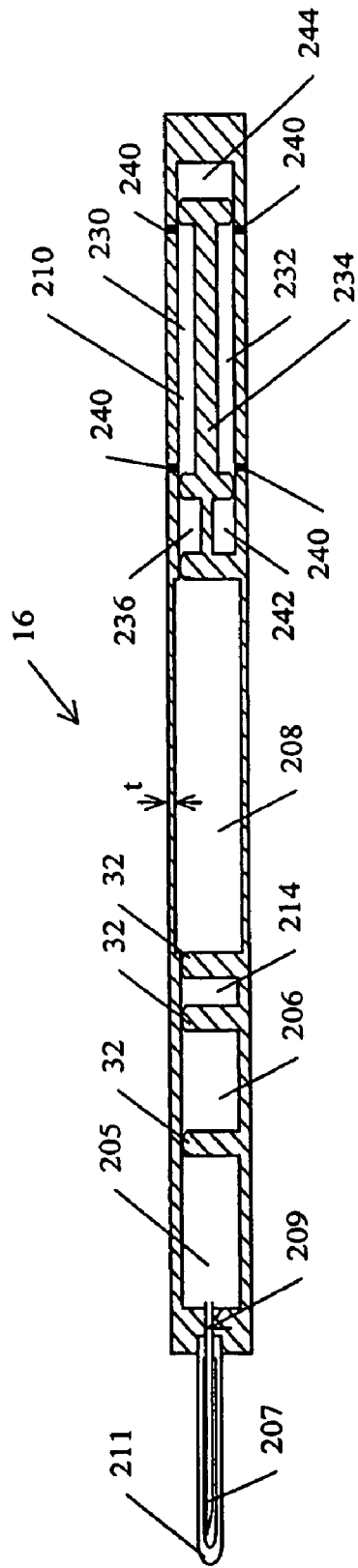
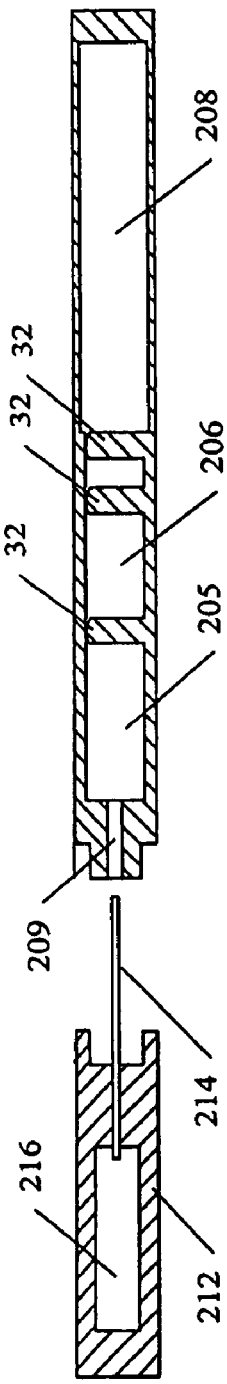
Fig. 15A
Fig. 15B

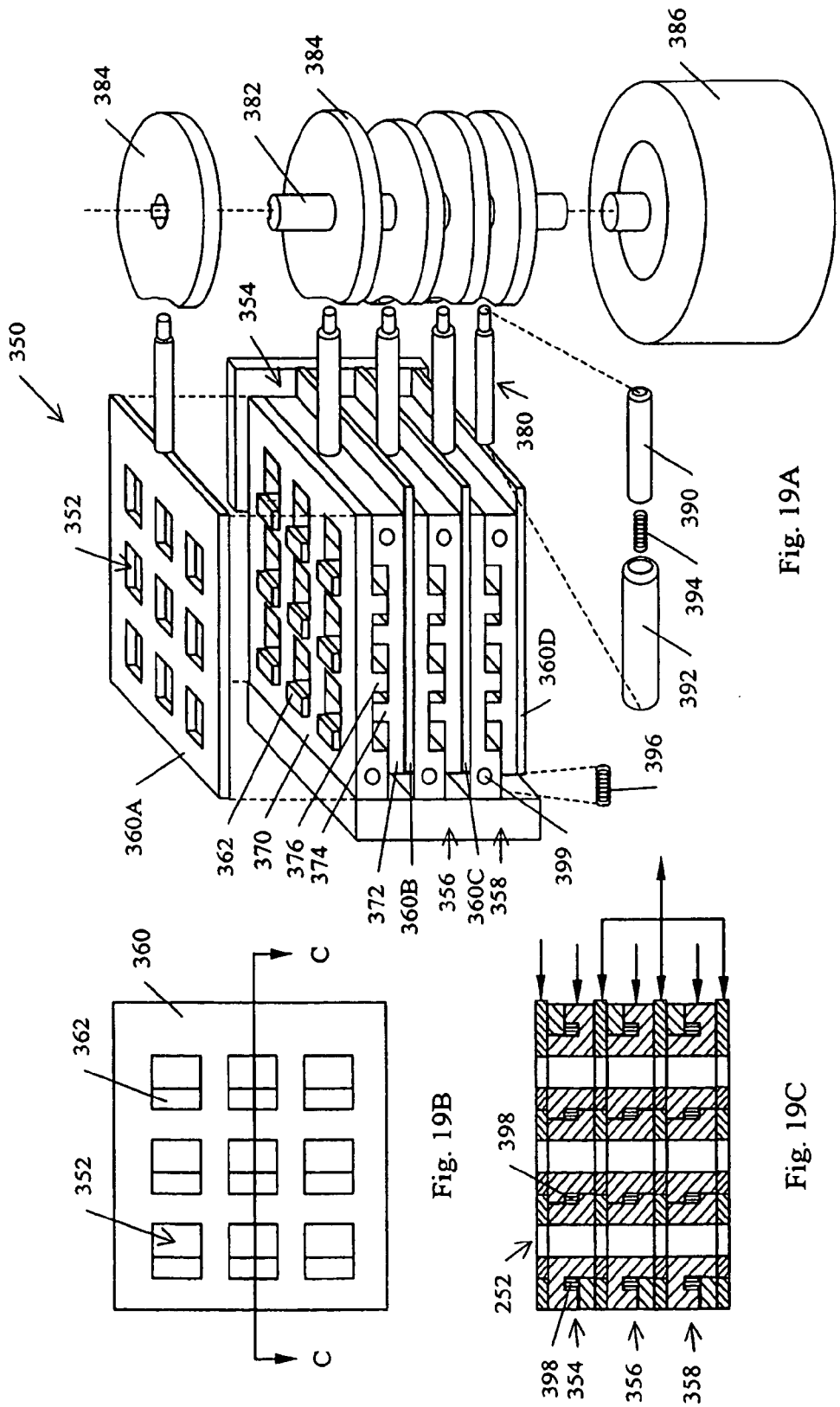

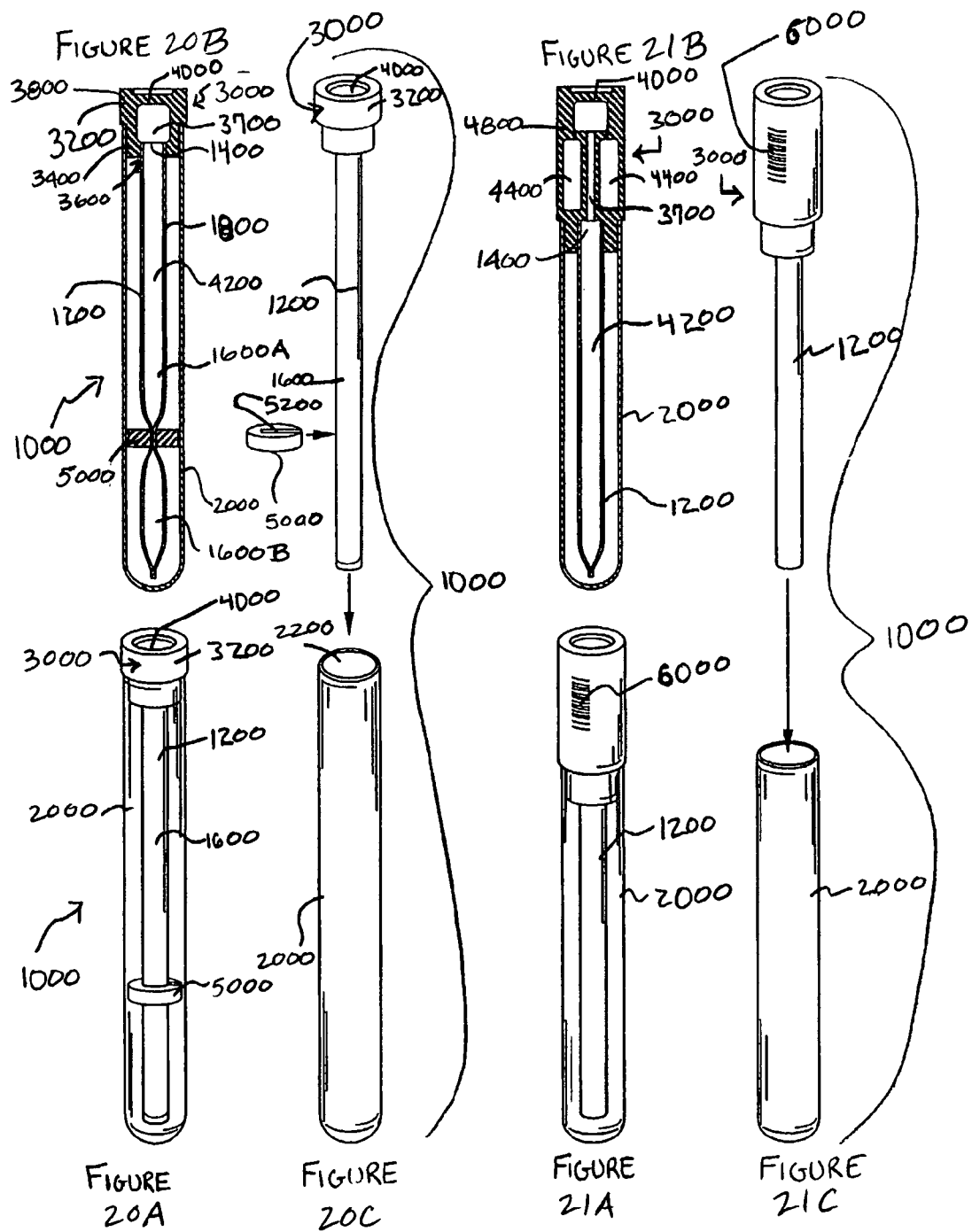

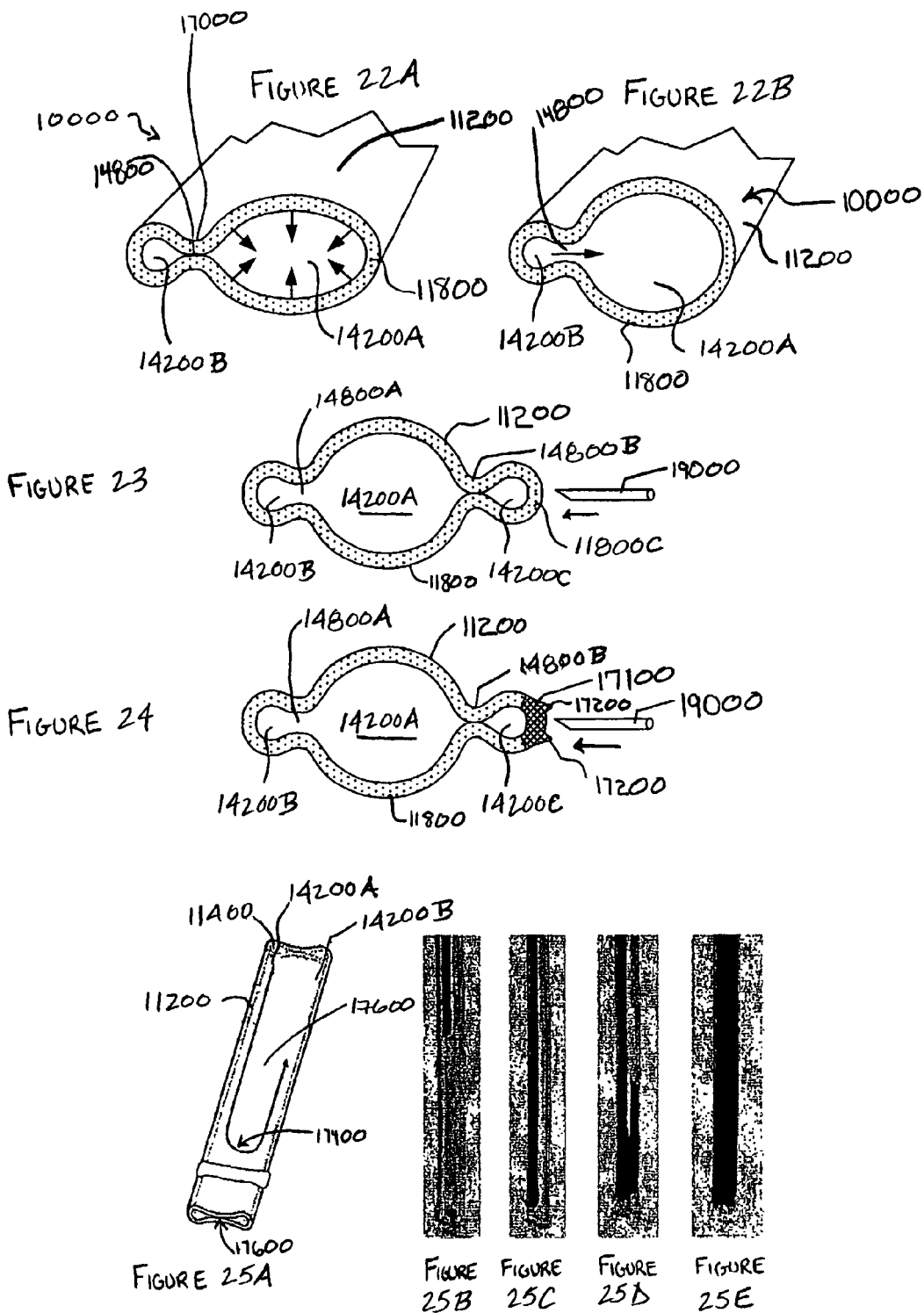

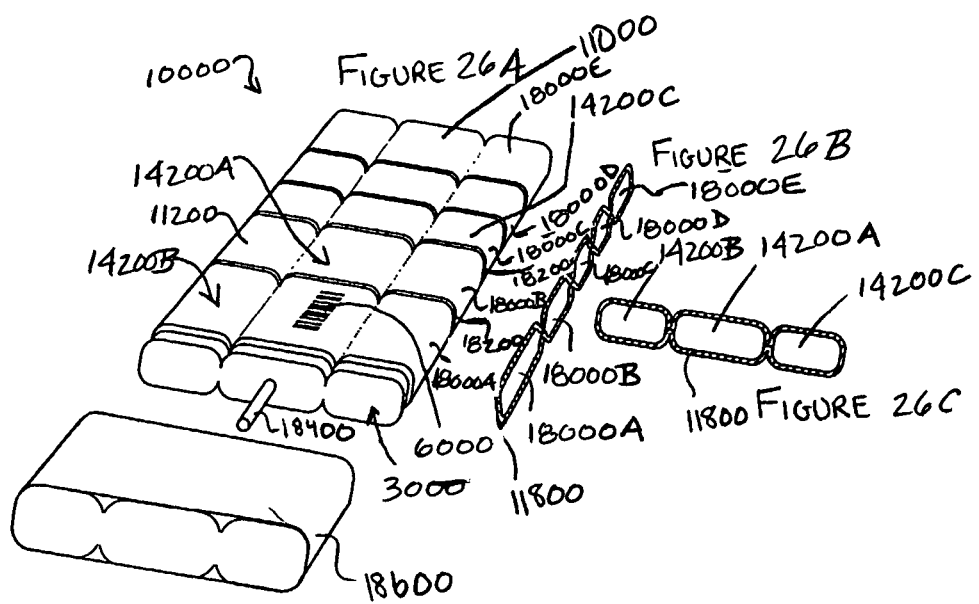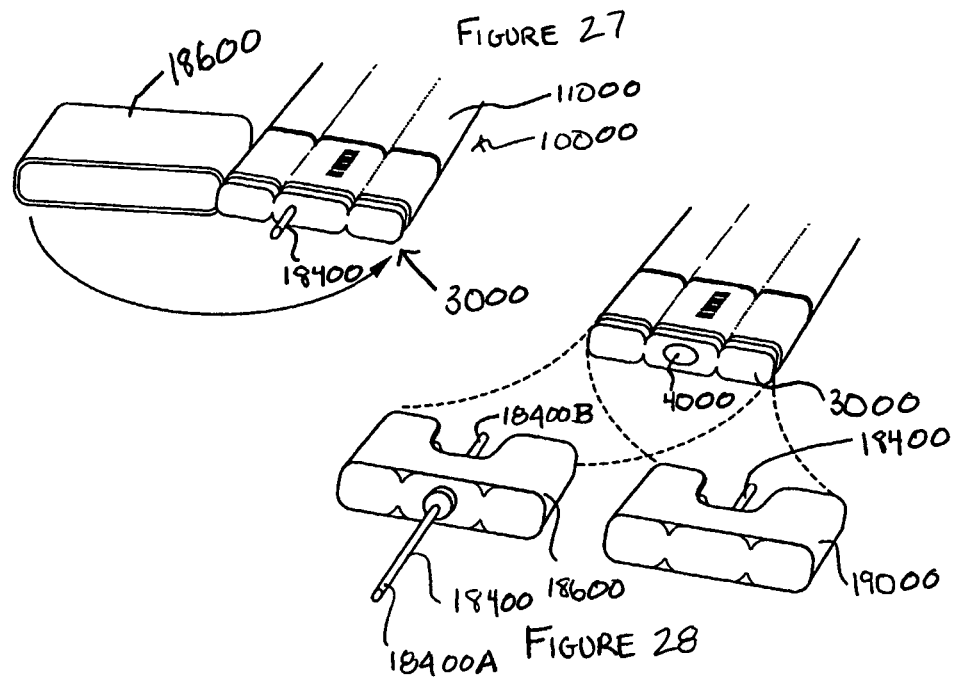

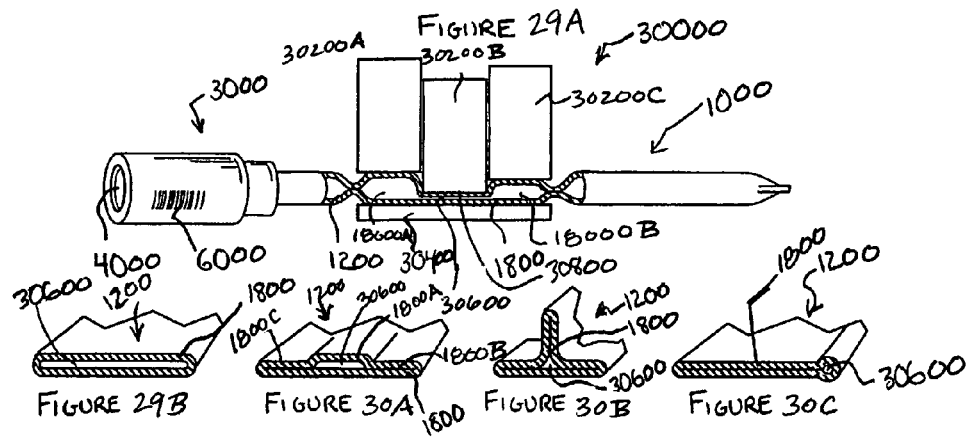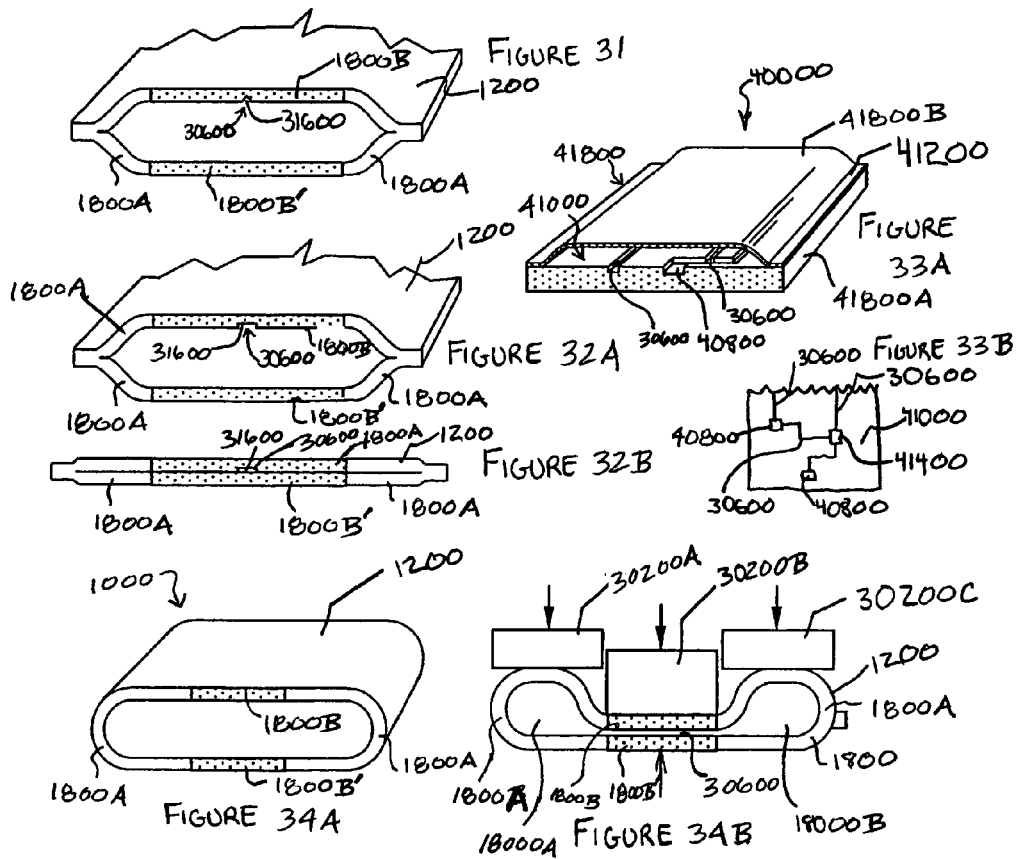

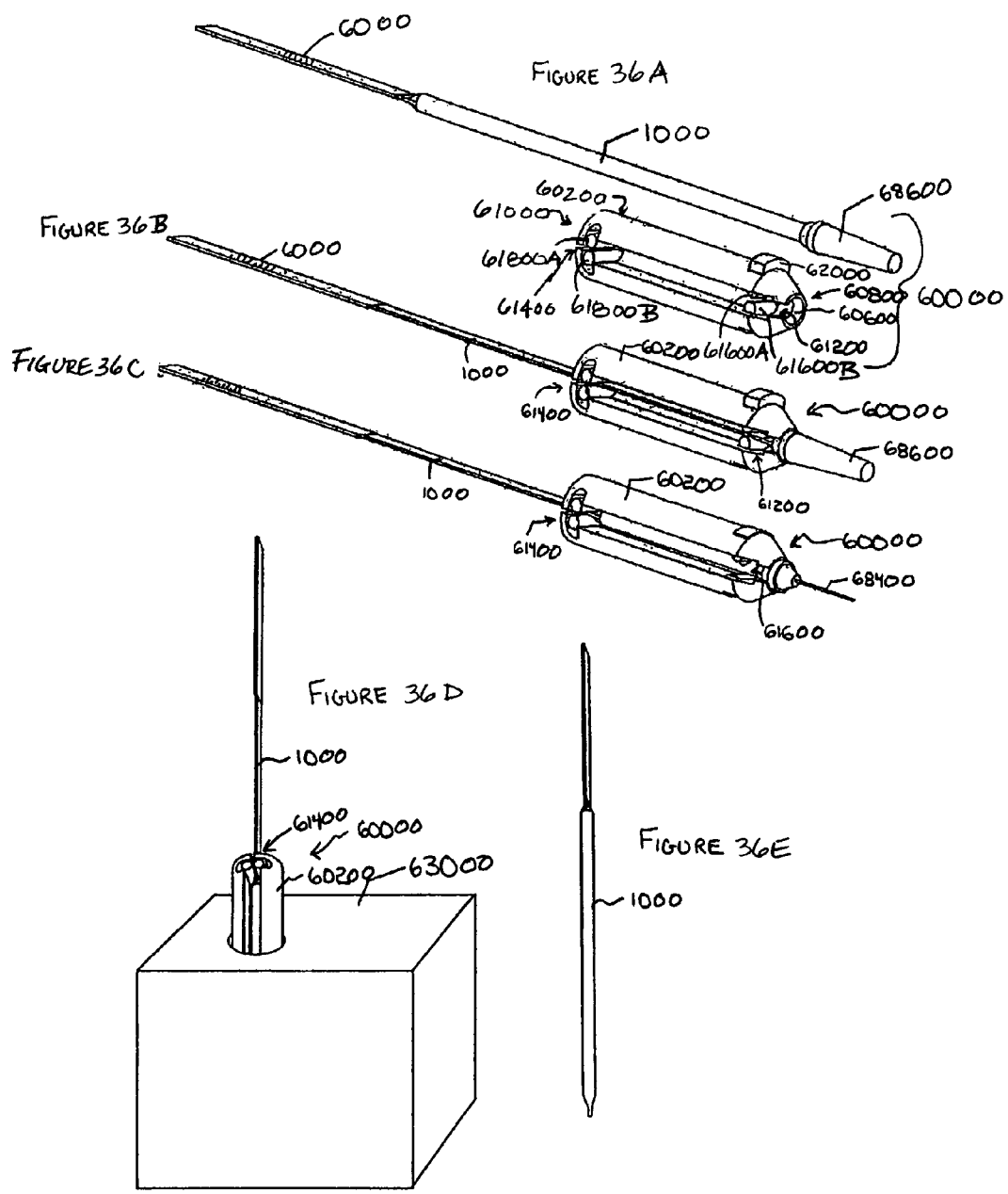

THERMAL CYCLING

CROSS-REFERENCE TO RELATED APPLICATIONS

This application is a continuation-in-part of U.S. patent application Ser. No. 09/782,732, filed Feb. 13, 2001, now U.S. Pat. No. 6,780,617, which claims priority to U.S. Provisional Patent Application Ser. No. 60/259,025, filed Dec. 29, 2000, and a continuation-in-part of U.S. patent application Ser. No. 09/910,233, filed Jul. 20, 2001, now U.S. Pat. No. 6,748,332, which is a continuation of U.S. patent application Ser. No. 09/339,056, filed Jun. 23, 1999, now U.S. Pat. No. 6,318,191, which claims priority to U.S. Provisional Patent Application Ser. No. 60/090,471, filed Jun. 24, 1998. This application further claims priority to U.S. Provisional Patent Application Ser. No. 60/318,768, filed Sep. 11, 2001. Each of the aforementioned patent applications and patents is incorporated herein by reference.

STATEMENT REGARDING FEDERALLY SPONSORED RESEARCH OR DEVELOPMENT

Portions of the disclosed subject matter were made with government support under grant numbers 1R43HL65768, 1R43HL65867 and 1R43HL67568 awarded by the National Institutes of Health. The government has certain rights in those portions.

BACKGROUND

As result of the Human Genome Project and other genetic research, a tremendous amount of genomic and biomarker information is presently available to healthcare providers. Using molecular diagnostic testing, genomic and biomarker information can provide a resource to healthcare providers to assist in the rapid and accurate diagnosis of illness. However, the development of diagnostic testing systems allowing the use of such genetic information, particularly in the clinical setting, has failed to match pace with the genetic research providing the information. Current diagnostic testing systems are mainly limited to large medical testing centers or research labs due to the high costs associated with acquiring and operating the systems and the complexity of the molecular diagnostic assays being employed. These current systems require a large initial capital investment and incur high costs for reagents, disposables, operation, maintenance, service and training.

Sample preparation and handling generally includes sample collection and any preprocessing required for subsequent biological and chemical assays. Sample collection and handling is an important part of in vitro diagnostic (IVD) testing, and is an important factor in determining the feasibility of test automation. With the advancement of medicine, the number of possible assays available to perform is continually increasing. In parallel, sample collection methods have evolved over the last several decades. In the case of blood sample collection, for example, disposable plastic syringes first replaced glass syringes to improve safety. Later developments had vacuum tubes replacing the traditional syringes to simplify the blood collection process. However, a vacuum tube is generally not suitable for use as an IVD test reaction chamber. Thus, a re-sampling process is necessary for delivery of the sample to distinct assay containers for each of a variety of IVD tests. Automation of these processes is a daunting task. Indeed, in large clinical testing centers giant automation testing systems costing several million dollars are currently used. The major automated task in these machines is liquid handling, which entails the pipetting of the sample from sample tubes to 96-well plates, the addition of the reagent(s) to the wells, as well as moving reaction mixtures from well to well.

Recently, nanotechnology has emerged to revolutionize automation and testing formats. In this direction, by using silicone micro-fabrication and etching technology, the lab-on-a-chip platform was developed in an attempt to integrate and miniaturize certain parts of the automation process into a chip with dimensions less than 2 mm by 2 mm. Liquid processing rates for certain lab-on-a-chip platforms can be on the scale of nanoliters per second. However, it is often difficult for users to interface with this type of platform to, for example, deliver the sample to the chip.

Another concern of current sample handling devices is the large sample volume routinely drawn from a patient for IVD testing. In the case of blood sample collection, for example, a small vacuum tube may take close to 5 ml whole blood. When multiple samples are required in the testing of various assays, several tubes of blood are frequently ordered. However, only a small amount is needed for each assay. The drawing of a large volume of blood for multiple tests is a concern for pediatric patients as it can lead to iron deficiency anemia. It is even more critical for patients with pre-existing anemia or a bleeding disorder.

SUMMARY

The present invention provides sample processing devices and methods that facilitate the rapid analysis of biological samples, such as blood, saliva, or urine, in an efficient and cost effective manner with minimal, if any, exposure to biohazards. The sample processing devices and methods of the present invention are particularly suited to the clinical setting, allowing the clinician to readily proceed from acquisition of a test sample to analysis of the test results, with minimal human intervention. The sample processing devices of the present invention may be implemented as a hand-held system suitable for the processing of a single sample or as a larger, bench top unit suitable for the simultaneous processing of multiple samples. The present invention may be valuable in all diagnostic and therapeutic monitoring areas, including in the point-of-care or clinical setting, in high-throughput screening, and in biological warfare detection. In addition, the present invention provides a sample vessel for holding a biological sample throughout the processing of the sample.

In accordance with one embodiment of the present invention, a device for processing a sample includes a processing unit having an opening to receive a sample vessel and at least one processing station positioned along the opening. The processing station includes a compression member adapted to compress the sample vessel within the opening and thereby displace a content of the sample vessel within the sample vessel. The content displaced by the compression member can be, for example, the sample, a reagent, or a mixture of the content and a reagent In accordance with another aspect, the processing station may include an energy transfer element for transferring energy to or from the content within the sample vessel and a control system coupled to the energy transfer element to control the energy transferred to or from the content. The energy transfer element can be, for example, an electronic heat element, a microwave source, a light source, an ultrasonic source or a cooling element.

In accordance with a further aspect, the energy transfer element transfers thermal energy to or from the content within the sample vessel. An energy insulator may be positioned adjacent the processing station. The energy insulator can be, for example, an energy shielding layer, an energy absorption layer, an energy refraction layer, or a thermal insulator, depending on the type of energy transfer element employed. A temperature sensor may be coupled to the control system to monitor temperature at the processing station. Alternatively, the processing station may include a heat sink to dissipate thermal energy from the processing station.

In accordance with another aspect, the processing station may include a stationary member opposing the compression member across the opening. The compression member can operate to compress the sample vessel against the stationary member within the opening.

In accordance with a further aspect, a driver may be coupled to the compression member to selectively move the compression member and thereby compress the sample vessel within the opening. The driver can be, for example, a motor coupled to the compression member by a cam. Alternatively, the driver can be an electromagnetic actuating mechanism.

In accordance with another aspect, the processing device can include a sensor for detecting a signal from the content within the sample vessel. An energy source can optionally be provided for applying energy to the content within the sample vessel to generate a signal from the content. In one embodiment, the processing device can include an electrophoresis system comprising a pair of electrodes adapted to have a predetermined voltage difference and an electrode actuator for inserting the electrodes into the sample vessel.

In accordance with a further aspect, the processing device may include a reagent injector cartridge actuator adapted to receive a reagent injector cartridge having at least one needle in fluid communication with a reagent reservoir. The reagent injector cartridge actuator can be operable to move the reagent injector cartridge to inject a quantity of reagent into the sample vessel.

In accordance with another embodiment of the invention, a sample vessel for holding a sample includes a sample containing portion for holding the sample and a handling portion for handling the sample vessel. The sample containing portion can have a wall constructed of a flexible material permitting substantial flattening of a selected segment of the sample containing portion. The handling portion can be coupled to the sample containing portion and preferably has a generally rigid construction to facilitate handling of the sample vessel.

In accordance with another aspect, the sample containing portion of the sample vessel can be a tubule.

In accordance with a further aspect, the sample vessel can include at least one pressure gate disposed within the sample containing portion to divide the sample containing portion into a plurality of segments. At least one of the segments of the sample vessel can have a filter contained therein that is structured to separate selected components of a sample material from other components of the sample material. Additionally, at least one of the segments of the sample vessel can contain a reagent. The reagent can be, for example, an anticoagulant, a cell lyses reagent, a nucleotide, an enzyme, a DNA polymerase, a template DNA, an oligonucleotide, a primer, an antigen, an antibody, a dye, a marker, a molecular probe, a buffer, or a detection material. The sample containing portion also can include an electrophoresis segment containing a gel for electrophoresis. The electrophoresis segment can include a pair of electrodes adapted to maintain a predetermined voltage difference therebetween. Additionally, one of the segments can contain multilayer membranes or a microarray bio-chip for analyzing the sample.

In accordance with another aspect, the sample containing portion can include a self-sealing injection channel formed therein. The self sealing injection channel is preferably normally substantially free of sample material and capable of fluid communication with the sample material in the sample containing portion.

In accordance with another aspect, the sample vessel can include an instrument for obtaining a sample coupled to the sample vessel.

In accordance with a further aspect, the handling portion of the sample vessel includes an opening for receiving a sample. The sample vessel also can include a closure for selective closing the opening. Preferably, the closure seats against the handling portion to close the opening. In addition, the instrument for obtaining a sample can be coupled to the closure of the sample vessel.

In accordance with another aspect, the handling portion has a wall thickness greater than a thickness of the wall of the sample containing portion. Preferably, the thickness of the wall of the sample containing portion is less than or equal to 0.3 mm. In one embodiment, the handling portion can include a cylindrical sleeve sized and shaped to fit over a portion of the sample containing portion. The handling portion is preferably positioned longitudinally adjacent the sample containing portion.

In accordance with another embodiment, a sample vessel for holding a sample includes a sample containing portion having at least one pressure gate disposed within the sample containing portion to divide the sample containing portion into a plurality of segments. Preferably, at least one segment of the sample containing portion has a wall constructed of a flexible material permitting substantial flattening of the segment of the sample containing portion.

In accordance with another embodiment, a method of processing a sample within a sample vessel includes the steps of introducing the sample vessel into a device for processing the sample and compressing the sample vessel to move the sample within the sample vessel from a first segment to a second segment of the sample vessel.

In accordance with another aspect, the method of processing a sample can include the step of introducing a reagent to the sample within a segment of the sample vessel.

In accordance with a further aspect, the method of processing a sample can include the step of heating the sample in the first segment to a first temperature. The method can also include the step of heating the sample to a second temperature in the second segment. In one embodiment, the first temperature can be effective to denature the sample and the second temperature is one at which nucleic acid annealing and nucleic acid synthesis can occur. The method of processing a sample can further include the steps of compressing the sample vessel to move the sample within the sample vessel from the second segment to the first segment of the sample vessel and heating the sample to the first temperature in the first segment.

In accordance with another aspect, the method of processing the sample can include the step of analyzing the sample by detecting a signal from the sample within a segment of the sample vessel and analyzing the detected signal to determine a condition of the sample. The analyzing step can include applying an excitation energy to the sample within the segment of the sample vessel. Additionally, the analyzing step can include conducting electrophoresis analysis of the sample by applying a selective voltage to the sample within a segment of the sample vessel, detecting light emitted from the sample, and analyzing the detected light to determine a condition of the sample.

Alternatively, the analyzing step can include applying an excitation energy to a bio-array member contained within a segment of the sample vessel, detecting light emitted from the bio-array member, and analyzing the detected light to determine a condition of the sample. The bio-array member can be, for example, a multi-layer membrane or a micro-array biochip.

In accordance with a further aspect, the method of processing a sample can include the step of agitating the sample within a segment of the sample vessel.

In accordance with another embodiment, a method of treating a sample within a sample vessel can include the steps of introducing the sample vessel into a device for processing the sample within the sample vessel and compressing one of the segments to mix the reagent with the sample within the sample vessel. Preferably, the sample vessel has a plurality of segments including a segment for containing a reagent and a segment for containing the sample.

In accordance with another aspect, the method of processing the sample can include the step of introducing the reagent into a reagent segment of the sample after the step of introducing the sample vessel into the device for processing the sample.

In accordance with another embodiment, a thermal cycler includes a processing unit having an opening to receive a sample vessel containing a sample. The processing unit can have a first processing station, a second processing station, and a third processing station positioned along the opening. The first processing station can include a first compression member adapted to compress the sample vessel within the opening and a first energy transfer element for transferring energy to the sample at the first processing station. The second processing station can include a second compression member adapted to compress the sample vessel within the opening and a second energy transfer element for transferring energy to the sample at the second processing station. The third processing station can include a third compression member adapted to compress the sample vessel within the opening and a third energy transfer element for transferring energy to the sample at the third processing station. Compression of the sample vessel by of one of the compression members can displace the sample within the sample vessel between the processing stations.

The present disclosure is also directed to sample vessels that can permit the collection and the processing of biological and chemical samples, such as, for example, blood, saliva, tissue, or urine, in a closed system. Sample devices disclosed herein may provide a uniform sample handling system that simplifies the sample collection process and reduces exposure to biohazards. One or more of the sample vessels disclosed herein can accommodate multiple fluid samples and a plurality of assays of different types, while concomitantly reducing the volume of sample necessary for testing.

In accordance with one exemplary embodiment, a sample vessel may comprise a tubule having an opening for receiving a sample material and at least one compressible section, a generally rigid container receiving at least a portion of the tubule, and an interface in fluid communication with the opening in the tubule. The at least one compressible section may have a wall constructed at least partially from a material having sufficient flexibility to permit compression of opposed sections of the wall into contact. The interface may facilitate delivery of a sample material to the tubule through the opening.

In accordance with another exemplary embodiment, a sample vessel may comprise a tubule having a plurality of lumens and a wall constructed at least partially from a material having sufficient flexibility to permit compression of opposed sections of the wall into contact with one another, and a pressure gate connecting at least two lumens of the plurality of lumens. The pressure gate may permit selective fluid flow between the at least two lumens.

In accordance with another exemplary embodiment, a sample vessel may comprise a tubule having a wall that forms a lumen when the tubule is in an open configuration. The wall may have a plurality of sections including at least a first section of the wall having sufficient flexibility to permit compression of a portion of the tubule and at least a second section of the wall having sufficient rigidity to support a flow channel within the tubule during compression of the tubule.

In accordance with another exemplary embodiment, an apparatus for drawing a sample into a sample vessel may comprise a cylindrical housing having an opening for receiving the sample vessel, first means for compressing a first portion of the sample vessel, and second means for compressing a second portion of the sample vessel. The first compression means may be positioned at a proximal end of the housing and the second compression means may be positioned at a distal end of the housing.

BRIEF DESCRIPTION OF THE DRAWINGS

These and other features and advantages of the sample vessels and processing devices and methods disclosed herein will be more fully understood by reference to the following detailed description in conjunction with the attached drawings in which like reference numerals refer to like elements through the different views. The drawings illustrate principles of the sample vessels and methods disclosed herein and, although not to scale, show relative dimensions.

FIG. 3 is a schematic diagram of an alternative embodiment of a device for processing a sample according to the present invention;

FIG. 4 is a schematic diagram of an alternative embodiment of a device for processing a sample according to the present invention;

FIG. 5 is a perspective view of an embodiment of a hand held device for processing a sample according to the present invention;

FIG. 6 is a perspective view of an embodiment of a bench top device for processing a sample according to the present invention;

FIGS. 13A-13G are side elevational views, in cross-section, of a processing unit of the present invention, illustrating the operation of the processing unit;

FIGS. 15A-15B are side elevational views, in cross-section, of embodiments of a sample vessel according to the present invention;

FIGS. 19A-19C illustrate an alternative embodiment of a processing unit of the present invention.

FIG. 20A is a perspective view of an exemplary embodiment of a sample vessel;

FIG. 20B is a side-elevational view in cross-section of the sample vessel of FIG. 20A;

FIG. 20C is an exploded view of the sample vessel of FIG. 20A, illustrating the tubule and collar removed from the container;

FIG. 21A is a perspective view of an exemplary embodiment of a sample vessel;

FIG. 21B is a side-elevational view in cross-section of the sample vessel of FIG. 21A;

FIG. 21C is an exploded view of the sample vessel of FIG. 21A, illustrating the tubule and collar removed from the container;

FIGS. 22A-22B are side-elevational views in cross-section of an exemplary embodiment of a sample vessel having a pair of lumens separated by a pressure gate;

FIG. 23 is a side-elevational view in cross-section of an exemplary embodiment of a sample vessel having three lumens separated by a pair of pressure gates;

FIG. 24 is a side-elevational view in cross-section of another exemplary embodiment of a sample vessel having three lumens separated by a pair of pressure gates, illustrating a self-sealing, reinforced wall section for facilitating injection by a needle;

FIG. 25A is a perspective view of an exemplary embodiment of a sample vessel having a pair of lumens connected by a micro-fluidic channel;

FIGS. 25B-25C are digital photographs of the sample vessel of FIG. 25A illustrating fluid flow through the lumens of the sample vessel;

FIG. 26A is a perspective view of an exemplary embodiment of a segmented sample vessel having a plurality of lumens;

FIGS. 26B and 26C are cross-sectional views of the sample vessel of FIG. 26A;

FIG. 27 a perspective view of another exemplary embodiment of a segmented sample vessel having a plurality of lumens, illustrating a hinged cover for the sample vessel;

FIG. 28 a perspective view of an exemplary embodiment of a segmented sample vessel having a plurality of lumens, illustrating alternative interfaces for the sample vessel;

FIG. 29A is a side elevational view in partial cross-section of an exemplary embodiment of a sample vessel, illustrating the compression of the sample vessel;

FIG. 29B is a cross-sectional view of the sample vessel of FIG. 29A taken along a line transverse to the longitudinal axis of the tubule 1200;

FIGS. 30A-30C are side elevational views in cross-section of an exemplary embodiment of a sample vessel, illustrating compression of the sample vessel into a plurality of configurations;

FIG. 31 is a side elevational view in cross-section of an exemplary embodiment of a sample vessel having a composite cross-section and a micro-fluidic flow channel;

FIGS. 32A-32B are side elevational views in cross-section of another exemplary embodiment of a sample vessel having a composite cross-section and a micro-fluidic flow channel, illustrating the sample vessel in a open configuration (FIG. 32A) and a compressed configuration (FIG. 32B);

FIG. 33A is a side elevational view in cross-section of an exemplary embodiment of a sample vessel having a plurality micro-fluidic flow channels interconnecting a plurality of depressions formed on an interior wall surface of the sample vessel;

FIG. 33B is a top view of an interior wall surface of the sample vessel of FIG. 33A;

FIGS. 34A and 34B are side elevational views in cross-section of an exemplary embodiment of a sample vessel having a composite cross-section including opposed planar wall sections, illustrating the sample vessel in an open configuration (FIG. 34A) and a compressed configuration (FIG. 34B);

FIGS. 36A-36E are perspective views of an apparatus for drawing a sample into a sample vessel, illustrating the operation of the apparatus.

DETAILED DESCRIPTION

Figure 1:
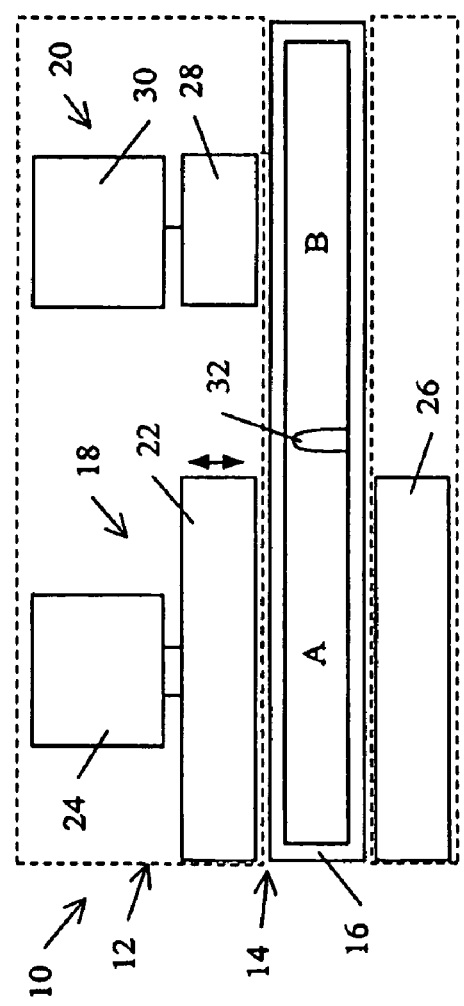
FIG. 1 is a schematic diagram of a device for processing a sample according to the present invention.

To provide an overall understanding, certain exemplary embodiments will now be described; however, it will be understood by one of ordinary skill in the art that the sample vessels and methods described herein can be adapted and modified to provide devices and methods for other suitable applications and that other additions and modifications can be made without departing from the scope of the present disclosure.

Unless otherwise specified, the exemplary embodiments described below can be understood as providing exemplary features of varying detail of certain embodiments, and therefore, unless otherwise specified, features, components, modules, and/or aspects of the exemplary embodiments can be otherwise combined, separated, interchanged, and/or rearranged without departing from the scope of the present disclosure. Additionally, the shapes and sizes of components are also exemplary and unless otherwise specified, can be altered without affecting the disclosed devices or methods.

The present disclosure provides devices and methods for processing a sample. The term "processing" as used herein generally refers to the preparation, treatment, analysis, and/or the performance of other testing protocols or assays on a content of the sample vessel in one or more steps. Exemplary processing steps include, for example: displacing a content, e.g., the sample or a reagent, of the sample vessel within the sample vessel to, for example, adjust the volume of the content, separate content components, mix contents within the sample vessel; effecting a chemical or biological reaction within a segment of the sample vessel by, for example, introducing a reagent to the sample, agitating the sample, transferring thermal energy to or from the sample, incubating the sample at a specified temperature, amplifying components of the sample, separating and/or isolating components of the sample; or analyzing the sample to determine a characteristic of the sample, such as, for example, the quantity, volume, mass, concentration, sequence, or nucleic acid size or other analyte size, of the sample. One skilled in the art will appreciate that the forgoing exemplary processing steps are described herein for illustrative purposes only. Other processing steps may be employed without departing from the scope of the present invention.

A device for processing a sample according to the present invention can integrate one or more processing units into a single system depending on the process being employed. The processing units can include one or more processing stations at which one or more processing steps can be performed on the sample within the sample vessel. Sample materials that can be processed according to the present invention are generally biological samples or samples containing biological substance and include, for example, blood, urine, saliva, cell suspensions, biofluids, a piece of tissue, soil or other samples. A sample processing device of the present invention is particularly suited for nucleic acid amplification, such as polymerase chain reaction (PCR) or ligase chain reaction (LCR) amplification, and can include, for example, a sample pretreatment unit for extracting nucleic acid from sample, a thermal cycling reaction unit for amplification of the nucleic acid or signal, and (optionally) an analysis or detection unit for analyzing the amplified product. The sample processing device of the present invention can also be used for isothermal reaction of nucleic acid or signal amplifications, such as strand displacement amplification (SDA), rolling circle amplification (RCA), and transcription-mediated amplification (TMA). Other exemplary processes to be performed on samples can include clinical diagnosis, therapeutic monitoring, and screening of chemical compounds for discovery of new drugs. The following description primarily focuses on PCR amplification for illustration. However, one skilled in the art will appreciate that the devices and methods of the present invention are not limited to PCR amplification, as the devices and methods described below can be employed in other sample processing.

An exemplary embodiment of a device for processing a sample is illustrated in FIG. 1. The processing device 10 illustrated in FIG. 1 includes a processing unit 12 having an opening 14 to receive a sample vessel 16. The opening 14 can be a tubular shaped opening, an open-faced slot or other structure for receiving the sample vessel 16 in a removable and replaceable manner. The processing unit 12 includes a first processing station 18 and a second processing station 20, each positioned along the length of the opening 14. The first processing station 18 includes a compression member 22 adapted to compress the sample vessel 16 within the opening 14 and thereby displace a content of the sample vessel within the sample vessel 16. The content of the sample vessel can be, for example, the sample, a reagent contained within the sample vessel, or a mixture of the sample and the reagent. A driver 24 is coupled to the compression member 22 to selectively move the compression member 22 and thereby compress the sample vessel 16 within the opening 14. The driver 24 can be, for example, an electromagnetic actuating mechanism, a motor, a solenoid, or any other device for imparting motion, preferably reciprocal motion, to the compression member 22, as described in further detail below.

Preferably, the compression member 22 is constructed from a rigid material such as a rigid plastic or a metal. The compression member can be constructed in any shape sufficient to impart a compressive force on the sample vessel. For example, the compression member 22 can be a block having a rectilinear, planar surface for engaging the sample vessel 16, as illustrated in FIG. 1. Alternatively, the compression member can have a curved, angular, or non-planar surface for engaging the sample vessel 16.

Moreover, the compression member 22 alternatively can be an inflatable membrane that can be inflated by a fluid, e.g., air, nitrogen, saline, or water, to impart a compressive force on the sample vessel. In this embodiment, the amount of compression of the sample vessel may be controlled by the adjusting the inflation pressure of the membrane.

Figure 2:
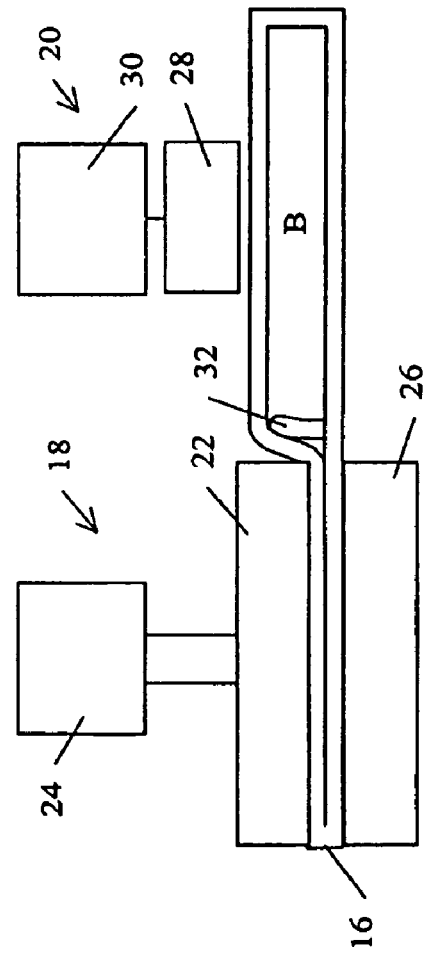
FIG. 2 is a schematic diagram of the device of FIG. 1, illustrating a compression member of a processing station of the device compressing the sample vessel.

The first processing station 18 can optionally include a stationary member 26 positioned opposite the compression member 22 across the opening 14. The compression member 22, thus, can compress a portion of the sample vessel 16 within the opening 14 against the stationary member 26, as illustrated in FIG. 2. One skilled in the art will appreciate that the stationary member 26 may be replaced with a second compression member, such that the processing station includes two compression members that move together to compress the sample vessel therebetween. In addition, a stationary member or second compression member may be omitted by securing the sample vessel 16 within the opening on either side of the compression member.

In the illustrated embodiment, the sample vessel 16 is a closed tubule flow-chamber for holding the sample. Preferably, one or more segments of the sample vessel 16 are constructed of a flexible, compressible material, such as, for example, polyethylene or polyurethane, to allow selective compression, and preferably flattening, of the sample vessel to move the sample, or other contents of the sample vessel, within the sample vessel, preferably while the sample vessel 16 remains in the device 10. In one preferred embodiment, the sample vessel 16 includes a plurality of segments separated by an integral, internal structure, such as a micro-fluidic pressure gate, as described in more detail below. Alternatively, the sample vessel 16 can be constructed without internal, integral structures to form segments and the device 10 can be utilized to segment the sample vessel by compressing selective portions of the sample vessel. One skilled in the art will appreciate that other types of sample vessels suitable for containing a sample may be used with the device 10 without departing from the scope of the present invention.

The second processing station 20 can include a sensor 28 for detecting a signal from the content, e.g., the sample or a reagent, of the sample vessel 16. For example, the sensor 28 can be an optical sensor for measuring light, for example fluorescent light, emitted from the sample or from fluorescent probes within the sample. In addition, multiple sensors or a spectrum sensor can be used when detection of multiple wavelength light is required. The detected signal can be sent to a CPU 30 to analyze the detected signal and determine a characteristic of the sample.

In operation, a sample can be introduced to a first segment A of the sample vessel 16 by injecting the sample through the walls of the sample vessel 16 or by introducing the sample through an opening formed in the sample vessel 16, as described in more detail below. In the present exemplary embodiment illustrated in FIGS. 1 and 2, the sample vessel 16 includes a pressure gate 32 that divides the sample vessel 16 into a first segment A and a second segment B. The sample vessel 14 can be inserted into the opening 14 of the device 10 such that the first segment A of the sample vessel 16 is aligned with the first processing station 18 and the second segment B is aligned with the second processing station 20, as illustrated in FIG. 1.

The driver 24 can operate to move the compression member 22 into contact with the sample vessel 16 such that the first segment A of the sample vessel 16 is compressed within the opening 14 between the compression member 22 and the stationary member 26. As the first segment A of the sample vessel 16 is compressed, a quantity of sample is displaced from the first segment A to the second segment B through the pressure gate 32. The volume of sample displaced is proportional to the amount of compression of the first segment A by the compression member 22. Thus, the compression member 22 of the first processing station 18 can be used to displace a specific quantity of sample into the second segment B of the sample vessel 16 for analysis at the second processing station 20. Substantially all of the sample can be displaced from the first segment A of the sample vessel 16 by completely flattening the first segment A of the sample vessel 16, as illustrated in FIG. 2. The sample can be analyzed in the second segment B of the sample vessel 16 at the second processing station 20.

An alternative embodiment of a device for processing a sample is illustrated in FIG. 3. The device 38 includes a processing unit 40 having three processing stations positioned along the opening 14, namely, a first process station 42, a second processing station 44 adjacent the first processing station 42, and a third processing station 46 adjacent the second processing station 44.

The first processing station 42 includes a compression member 22 coupled to a driver 24 and adapted to compress a segment of the sample vessel 16 against a stationary member 26 within the opening 16. The first processing station 42 can operate to displace a selective quantity of the sample from a first segment A of the sample vessel into other segments of the sample vessel.

The second processing station 44 includes a compression member 22 coupled to a driver 24 and adapted to compress a second segment B of the sample vessel 16 against a stationary member 26 within the opening 16. The second processing station 44 includes an energy transfer element 48 for transferring energy to or from the contents of the sample vessel 16. The energy transfer element 48 can be, for example, an electronic heat element, a microwave source, a light source, an ultrasonic source, a cooling element, or any other device for transferring energy. In one embodiment, the energy transfer element 48 transfers thermal energy to or from the sample within the sample vessel. The energy transfer element 48 can be embedded in or otherwise coupled to the compression member 22, as illustrated in FIG. 3. Alternatively, the energy transfer element 48 can be coupled to the stationary member 26 or can be positioned within the processing station independent of the compression member or the stationary member. The energy transfer element 48 can be coupled to a control system that controls the energy transferred to or from the sample vessel 16 by the energy transfer element 48. The control system can be a component system of the CPU 30 or can be an independent system. The control system can also include a temperature sensor 50 to monitor the temperature of the energy transfer element.

The second processing station 44 also can include a sensor 52 for detecting a signal from the content of the sample vessel, particularly during processing in the second processing station. For example, the sensor 52 can be an optical sensor for measuring light, for example fluorescent light, emitted from the sample or from fluorescent probes within the sample. The sensor 52 can be coupled to the CPU 30 for analysis of the detected signal to determine a characteristic of the sample.

The third processing station 46 can include a sensor 28 for detecting a signal from the content, e.g., the sample or a reagent, of the sample vessel 16. For example, the sensor 28 can be an optical sensor for measuring light, for example fluorescent light, emitted from the sample or from fluorescent probes within the sample. In addition, multiple sensors or a spectrum sensor can be used when detection of multiple wavelength light is required. The detected signal can be sent to a CPU 30 to analyze the detected signal and determine a characteristic of the sample.

In operation, a sample can be introduced into a first segment A of the sample vessel 16 and the sample vessel 16 can be introduced into the opening 14 of the device 10. In the embodiment illustrated in FIG. 3, the sample vessel 16 includes two pressure gates 32 that divide the sample vessel 16 into three segments, namely, the first segment A, a second segment B, and a third segment C. The first processing station 42 can operate to displace a selective amount of the sample into the second segment B of the sample vessel 16 for processing at the second processing station 44.

At the second processing station 44, energy can be transferred to or from the sample within the second segment B. In this manner, a biological or chemical reaction involving the sample may be carried out in the second segment B. The sensor 52 can be used to monitor the reaction during the reaction process.

Upon completion of the reaction, the sample can be moved into the third segment C of the sample vessel 16 by compressing the sample vessel 16 within the opening at the second processing station 44. Preferably, the compression member 22 of the first processing station 42 substantially flattens the first segment A of the sample vessel 16 to inhibit the sample from entering the first segment A. The sample can be analyzed in the third segment C of the sample vessel 16 at the third processing station 46.

A further embodiment of a device for processing a sample is illustrated in FIG. 4. The device 56 includes a processing unit 58 having a processing station 60 positioned along the opening 14. The processing station 60 includes a compression member 22 coupled to a driver 24 and adapted to compress a segment of the sample vessel 16 against a stationary member 26 within the opening 16. In the embodiment illustrated in FIG. 4, the sample vessel 16 includes a pressure gate 32 that divides the sample vessel 16 into two segments, namely, a first segment A and a second segment B. The processing station 60 can operate to displace a selective quantity of the content from the second segment B of the sample vessel into the first segment A of the sample vessel. For example, a reagent can be introduced into the second segment B of the sample vessel 16. A quantity of reagent can be displaced from the second segment B into the first segment A of the sample vessel 16 to mix with the sample in the first segment A. Alternatively, the reagent can be introduced into the first segment A of the sample vessel 16 and a quantity of the sample can be displaced from the second segment B into the first segment A by the processing station 60. Thus, the first segment A of the sample vessel 16 can act as a reaction mixture chamber for the sample and the reagent. The reagent can be pre-packaged in the sample vessel 16 or can be introduced to the sample vessel 16 after the sample is introduced to the sample vessel 16. For example, the reagent can be introduced using a reagent injector cartridge, described below, that is included with the device.

Referring to FIG. 5, another embodiment of device for processing a sample is illustrated. The illustrated device 100 is a hand held system for processing a nucleic acid sample, preferably in an "insert and test" format in which a sample vessel containing a nucleic acid sample is inserted into the device 100 and processing results are produced by the device with minimal human intervention. The device 100 can include a housing 112 having an opening 114 for receiving a sample vessel 116 containing a sample for processing by the device 100. The opening 114 can be a tubular shaped opening, as illustrated in FIG. 5, or can be an open-faced slot or other structure for receiving the sample vessel in a removable and replaceable manner. A control panel 118 is located on the top of the housing 112 for inputting information to the device 100 and a monitor 120 is provided for displaying operating information, such as the results of processing. An external communication port 121 can be located on the housing 112 for receiving information or outputting information, such as the results of processing and remote diagnosing of the system, to a remote system, such as a computer network. A battery 123 (FIG. 7) can be located within the housing to provide electrical power to the components of the device 100.

A multi-sample device 200 for processing multiple samples is illustrated in FIG. 6. The device 200 is a bench top thermal cycling system for processing up to 96 nucleic acid samples simultaneously. The sample processing device 200 operates on the same principals as the sample processing device 100 illustrated in FIG. 5, except that the multi-sample device 200 provides increased capacity and throughput. The multi-sample processing device 200 can include a housing 202 having a plurality of wells or openings 204, with each well being capable of receiving a sample vessel 206 containing a sample for processing by the device. The exemplary multi-sample device 200 illustrated in FIG. 6 has ninety-six wells for treating up to 96 samples simultaneously. One skilled in the art will appreciate that a multi-sample processing device according to the present invention may be designed with any number of wells, depending on the sample being tested and the processes being employed, without departing from the scope of the present invention. A control panel 208 is located on the top of the housing 202 for inputting information to the multi-sample processing device 200 and a monitor 210 is provided for displaying operating information, such as the results of testing.

Figure 7:
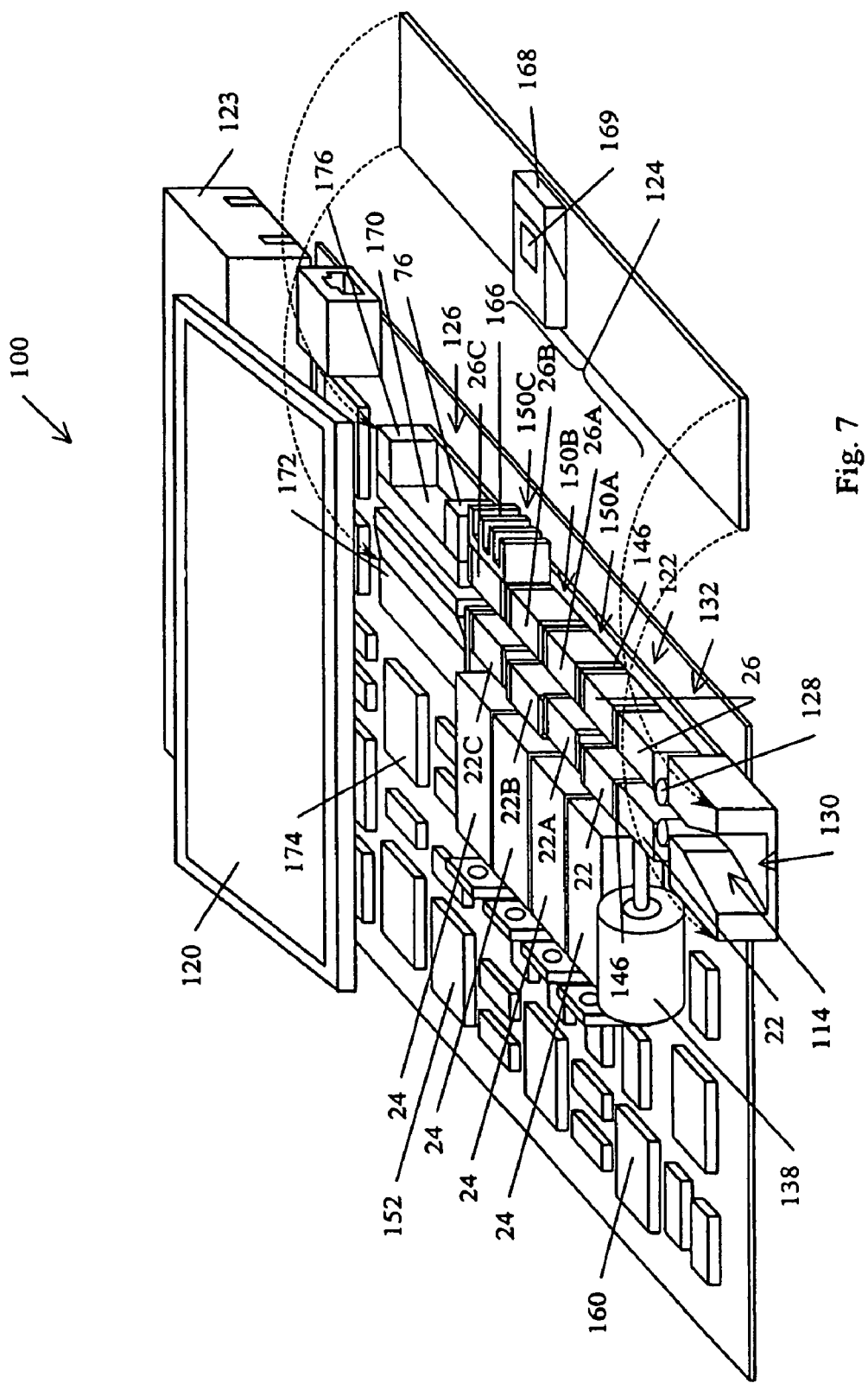
FIG. 7 is a perspective view of the device of FIG. 6, illustrating the device with the top cover removed.

FIG. 7 illustrates the general components of the sample processing device 100 illustrated in FIG. 5. The illustrated device 100 includes three primary processing units for processing a sample within the sample vessel, namely, a pretreatment unit 122 for pretreating the sample, a reaction unit 124 for amplifying certain components of the sample, and an analysis unit 126 for analyzing the sample. The sample vessel can be loaded into the device 100 through the opening 114. The processing units of the device are preferably arranged along the axis of elongation of the opening 114. This arrangement allows the sample to be moved within the sample vessel between the processing units of the device 100 in a manner described in detail below. Preferably, the processing units are arranged linearly as illustrated in FIG. 7, however, other arrangement are possible so long as the sample vessel can be positioned adjacent one or more of the processing units of the device 100.

Continuing to refer to FIG. 7, a pair of sample vessel loading wheels 128 is located at the entrance 130 of the sample vessel opening 114. The entrance 130 is preferably tapered to facilitate loading of the sample vessel into the opening 114 of the device 100. The loading wheels 128 further facilitate loading of the sample vessel by guiding the sample vessel into the opening 114. A sample collection unit 132 can be positioned proximate the entrance 130 of the opening 114 to allow a selective volume of the sample to dispense into the next processing unit or units within the sample vessel. The sample collection unit 132 can include a compression member 22 opposed to a stationary member 26 across the width of the opening 114. A linear motor 138 is coupled to the compression member 22. The linear motor 138 can operate to move the compression member 22 toward or away from the stationary member 26 to selectively open and close the opening 114 therebetween. When the sample vessel is positioned within the opening 114, the linear motor 138 can operate to compress the sample vessel between the compression member 22 and the stationary member 26. As a result, a selective volume of the sample can be moved to the next processing unit within the sample vessel. Preferably, the sample vessel remains compressed between the compression member 22 and the stationary member 26 of the sample collection unit 132 during processing of the sample by the other processing units to prevent the sample from exiting the processing unit area during processing.

The pretreatment unit 122 is positioned adjacent the initial sample collection unit 132. Depending on the process being implemented, the sample may require pretreatment or preparation before proceeding with additional processing steps. Pretreatment can include, for example, adding a reagent or other material to the sample and incubating the mixture for certain time period. The pretreatment unit 122 of the device 100 allows for any of such pretreatment steps to be implemented. For PCR testing, the sample pretreatment unit 122 can provide for nucleic acid extraction from a biological sample, such as blood. Any known methods for extracting nucleic acid can be utilized in the pretreatment unit, including using a cell lysis reagent, boiling the nucleic acid sample, GITC, or formamide for solubilization. Alternatively, filters can be used within the sample vessel to separate nucleic acid from unwanted cellular debris.

The pretreatment unit 122 can include a compression member 22 and a stationary member 26 opposed to the compression member 26 across the opening 114. The compression member 22 and/or the stationary member 26 can optionally include an energy transfer element for transferring energy, e.g. thermal energy, to the sample within the sample vessel. The energy transfer element can be, for example, an electronic heat element (such as Kapton heater, a Nomex heater, a Mica heater, or a silicone rubber heater), a microwave generator, a light source, an electronic cooling element (such as Peltier element), an ultrasonic energy transfer element, or any another device suitable for transferring thermal energy. A driver 24, for example an electromagnetic actuator such as linear stepper actuator, a relay actuator, or a solenoid, is coupled to the compression member 22 and operates as a driver. During operation of the pretreatment unit 122, the driver 24, moves the compression member 22 to open the opening 114 between the compression member 22 and the stationary member 26 of the pretreatment unit 122 to allow receipt of a sample vessel. After a sample vessel is loaded, the driver 24 drives the compression member 22 toward the stationary member 26, resulting in good surface contact between the sample vessel and the compression member and the stationary member and thus improved pretreatment. Once the pretreatment is completed, the driver 24 moves the compression member 22 of the pretreatment unit 122 to further compress the pretreatment segment of the sample vessel to move a selective amount of pretreated sample within the sample vessel to the next processing unit.

The reaction unit 124 can include a plurality of processing stations 150A-150C and is preferably positioned adjacent the pretreatment unit 122. The reaction unit 124 can effect thermal-cycling of the sample by selectively moving the sample, with the sample vessel, between the processing stations 150A-150C. The phrase "thermal cycling" as used herein refers to a process of heating and/or cooling a sample in two or more steps, with each step preferably occurring at a different temperature range from the previous step. Each of the processing stations 150A-150C can be maintained at a preselected temperature range controlled by a temperature control system 152 and a CPU 174. Although the exemplary embodiment includes three thermal cycling processing stations 150A-150C, the reaction unit 124 can include any number of processing stations 150, depending on the thermal cycling process employed. Alternatively, the reaction unit 124 can incubate a sample at a selective temperature for an isothermal reaction such as for TMA or SDA process.

In PCR based testing, thermal cycling can be used to denature, anneal, elongate and thereby amplify the nucleic acid sample. The PCR thermal cycling steps each occur at specified temperature ranges. Denaturing occurs at approximately 92° C.-96° C.; elongation occurs at approximately 70° C.-76° C.; and annealing occurs at approximately 48° C.-68° C. Each of the PCR thermal cycling steps, i.e. denaturing, annealing, and elongation, can be carried out independently at a separate processing station of the reaction unit 124 by maintaining the processing stations at the temperature ranges effective for carrying out each of the PCR thermal cycling steps. For example, the denaturing step can be carried out at processing station 150A, the elongation step at processing station 150B, and the annealing step at processing station 150C. Alternatively, one or more of the PCR thermal cycling steps can be combined and carried out at the same processing station, thereby reducing the number of processing stations required. For example, denaturing can be carried out at processing station 150A and elongation and annealing can be carried out at processing station 150B, thus, eliminating the need for a third processing station.

Moreover, a processing station can be provided within the reaction unit 122 for cooling of the sample by using a thermal energy element, a Peltier thermal electric element for example, to transfer thermal energy from the processing station. In PCR processing, for example, a processing station can be provided to preserve the nucleic acid sample between process steps by cooling the sample to a refrigeration temperature, e.g., 4° C. Additionally, a processing station can optionally be provided to cool the sample between thermal cycling steps to decrease the temperature down ramping time between successive thermal cycling steps. For example, as denaturing generally occurs at 92° C.-96° C. and annealing generally occurs at a significantly lower temperature, e.g., 48° C.-68° C., the sample can be cooled after denaturing in a cooling processing station, preferably at a temperature lower than the annealing temperature, to bring the sample temperature more quickly into the annealing temperature range. A thermal cycling processing station can optionally include a heat sink 166 coupled to either the compression member 22 or the stationary member 26 to conduct heat away from the station and radiate the heat to the environment.

Each of the illustrated processing stations of the reaction unit 124 includes a compression member 22 and a stationary member 26. The compression member 22 of each thermal cycling processing unit can be coupled to a driver 24 for selectively moving the compression member 22 toward and away from the stationary member 26. As discussed above, the drivers 24 can be any device capable of imparting motion, preferably reciprocal motion, to the compression members. A driver control system 160 is coupled to the drivers 24 to control the operation of the drivers 24. In one preferred embodiment illustrated in FIG. 7, the drivers 24 are electromagnetic actuators coupled to the driver control system 160, which can be, for example, a control system for controlling the reciprocal motion of the actuators. Alternative drivers, compression members and stationary members are described below in connection with FIGS. 8-12. The driver control system 160 is coupled to the CPU 174 such that the sample incubation time period, the pressure and the sample moving speed within the sample vessel can be controlled and coordinated by the CPU 174 to achieve the best reaction results.

Each of the thermal cycling processing station 150A-150C can optionally include an energy transfer element for transferring energy, such as thermal energy, to the sample within the sample vessel. The energy transfer elements can be, for example, an electronic heat element, a microwave generator, a light source, an electronic cooling element, or any another device suitable for applying thermal energy. Each of the energy transfer elements is coupled to the temperature control system 152 to maintain the associated processing station within a selected temperature range. One or more temperature sensors, coupled to the temperature control system 152, can be positioned proximate the processing stations 150A-150C to monitor the temperature of the stations.

Between two adjacent processing units or two adjacent processing stations, at least one layer of energy insulator 146 can optionally be provided to insulate the processing unit or the processing station from adjacent units or stations. An energy insulator layer can also be formed on the boundary of a processing station to prevent energy transfer to or from the environment. The energy insulator 146 can be, for example, an energy shielding layer, an energy absorption layer, an energy refraction layer, or a thermal insulator, depending on the type of energy transfer element employed. A thermal insulator can be constructed from a low thermal conductivity material such as certain ceramics or plastics. In one embodiment, the thermal insulator can be attached to the compression members and the stationary members. Alternatively, the thermal insulators can be separate from the compression members and stationary members and can be controlled independently by a driver to open and close the opening 114. In this embodiment, all the compression members and insulators can open initially to allow loading of the sample vessel, and then, the thermal insulators can compress the sample vessel within the opening to close the vessel and form separate segments within the sample vessel. Additionally, a spring element or other biasing mechanism can be optionally utilized to bias each thermal insulator. Through the spring element, a driver associated with one of the thermal insulators can apply sufficient pressure on the thermal insulator to minimize the quantity of sample remaining in the junction between adjacent processing stations during an incubation period, while still allowing sample flow through the thermal insulator when a higher pressure is applied to the sample in an adjacent processing station. This design simplifies the operation of multiple thermal insulators.

In an alternative embodiment, the processing stations can be spaced apart to inhibit conductive heat transfer between adjacent processing stations and, thereby, eliminate the need for insulators between the stations.

Operation of the thermal cycling reaction unit 124 will be generally described with reference to FIGS. 13A-13G. The thermal cycling process begins by opening each of the processing stations, e.g. first processing station 150A, second processing station 150B, and third processing station 150C, to receive the sample vessel within the opening 114, as illustrated in FIG. 13A. After the sample vessel is loaded with pretreated sample material, or the pretreated sample is dispensed from pretreatment unit 122 into the reaction unit 124, the second processing station 150B and the third processing station 150C are closed by moving the compression member 22B and the compression member 22C of each station toward the respective stationary member 26B and 26C, as illustrated in FIG. 13B. As the second processing station 150B and the third processing station 150C are closed, the sample vessel is compressed between the compression member and the stationary member, displacing the sample within the sample vessel into a segment of the sample vessel adjacent the first processing station 150A.

Next, the compression member 22A and the insulator 146A can compress the sample vessel to adjust the sample volume contained within the segment of the sample vessel adjacent the first processing station 150A, as well as the surface area to volume ratio of the segment. The insulator 146A can then be closed to seal the sample in the first processing station 150A, as illustrated in FIG. 13C. Alternatively, if the device 100 is provided with a sample pretreatment unit, the sample pretreatment unit can function to close the sample vessel within the first processing station 150A. Other alternatives include pre-sealing the sample vessel after loading a sample, or providing the sample vessel with pressure gates, discussed below, formed between adjacent reaction zones. Once the sample is sealed within the first processing station 150A, the sample can be heated or cooled by the first processing station 150A. In PCR thermal cycling, for example, the sample can be heated to a temperature effective to denature the nucleic acid sample. Preferably, the sample vessel is pressed into contact with the compression member 22A and the stationary member 26A by the compression member 22A to flatten the sample vessel and to ensure good thermal contact between the sample vessel and the compression member 22A and the stationary member 26A. The compression member 22A can also optionally periodically squeeze the sample vessel to agitate the sample and to generate sample flow in the segment of the sample vessel during the reaction period to speed up the reaction.

After a predetermined period, the second processing station 150B can be opened to allow the sample to move into the second processing station 150B, as illustrated in FIG. 13D. Next, the first processing station 150A closes, compressing the sample vessel and moving the entire sample, within the vessel 16, into a segment of the sample vessel adjacent the second processing station 150B, as illustrated in FIG. 13E. The third processing station 150C can then open to allow the sample to move into the segment of the sample vessel adjacent the third processing station 150C, as illustrated in FIG. 13F. The second processing station 150B closes, compressing the sample vessel and moving the sample completely into the segment of the sample vessel adjacent the third processing station 150C, as illustrated in FIG. 13G. The sample can then be heated or cooled by the third processing station 150C for a set time period. In PCR thermal cycling for example, the sample can be heated to a temperature effective to anneal the nucleic acid sample in the third processing station 150C. The heat sink 166 can facilitate the temperature transition from the denaturing temperature of the first processing station 150A to the annealing temperature of the third processing station 150C by dissipating excess heat to the environment. Thus, the sample can be moved from the denaturing step at the first processing station to the annealing step at the third processing station.

After a predetermined time period, the second processing station 150B opens to allow the sample to move into the second processing station, as illustrated in FIG. 13F. The third processing station 150C then closes, compressing the sample vessel 16 and moving the sample entirely into the segment of the sample vessel adjacent the second processing station 150B, as illustrated in FIG. 13E. The sample can then be heated or cooled by the second processing station 150B for a set time period. In PCR thermal cycling for example, the sample can be heated to a temperature effective to elongate the nucleic acid sample. Upon conclusion of the elongation step, the sample can be returned to the segment of the sample vessel adjacent the first processing station 150A to repeat the cycle, i.e., denaturing and annealing and elongating or, the sample can be moved to a segment of the sample vessel adjacent the sample detection unit 126 if PCR thermal cycling is completed.

The illustrated thermal cycling reaction unit 124 provides denaturing in the first processing station 150A, annealing in the third processing station 150C, and elongation in the second processing station 150B, as this arrangement is deemed thermodynamically efficient. One skilled in the art will appreciate, however, that the PCR thermal cycling steps can occur in any of the processing stations without departing from the scope of the present invention.

Sample thermal cycling using the reaction unit 124 of the present invention results in faster thermal cycling times and lower energy consumption compared to conventional thermal cycling devices. Sample vessel shape alteration, i.e. flattening, by the reaction unit 124 results in significant increases in the surface/volume ratio and sample vessel contact with the members of the reaction unit. This allows the processing stations of the reaction unit 124 to heat the sample more directly, increasing the sample temperature ramping rate and avoiding unnecessary temperature ramping of the members and thus decreasing the amount of energy consumed. Equally important is that sample vessel shape alteration provides for the uniform transfer of thermal energy to the sample, dramatically reducing reaction mixture temperature gradients. The reaction unit 124 further allows the use of fluid flow to mix the sample as the sample is moved from one processing station to another.

Moreover, the reaction unit 124 allows the use of a disposable, single-use sample vessel that minimizes contamination of the sample, contamination of the reaction unit and exposure of the operator to biohazards. Additionally, the reaction unit 124 does not require a fluid handling system, as the sample can be moved within the sample vessel during processing.

Referring again to FIG. 7, the reaction unit 124 can optionally include a reaction sensor 168 for monitoring the reaction in real-time within the reaction unit 124 by analyzing the sample, including any reaction products from the reaction with the sample. The reaction sensor 168 can include an integral light source 169 for applying excitation energy to the sample within the sample vessel. Alternatively, a light source, or other source of excitation energy, can be provided separate from the reaction sensor 168. The reaction sensor 168 can be an optical sensor for measuring light, for example fluorescent light, emitted from the sample or from fluorescent probes within the sample. In the case of PCR, any known real-time PCR detection system can be employed, including, for example, using fluorescent dyes, such as ethidium bromide, intercalating into the DNA molecule, using a dual labeled probe tagged with a reported dye and a quenching dye, or using hybridization probes, which will result in Fluorescence Resonance Energy Transfer (FRET) only when the two probes are hybridized and in close proximity. In each of these approaches, the fluorescence signal is substantially proportional to the amount of specific DNA product amplified. The reaction detection sensor 168 is placed to monitor the fluorescence from the sample, preferably in the annealing processing station, or other processing stations of the reaction unit, dependent on the assay selected. Multiple sensors or a spectrum sensor can be used when detection of multiple wavelength light is required. The detected signal is then sent to the CPU 174 for further analyzing the amount of product.

Continuing to refer to FIG. 7, the sample detection or analysis unit 126 of the device 100 is provided to analyze the sample after processing by the reaction unit 124. The analysis unit 126 is preferably positioned proximate the reaction unit 124. In one embodiment of the invention, a source of excitation energy, for example a light source, can apply excitation energy to the sample and a signal detector, for example an optical sensor, can detect light emitted from the sample in response to illumination by the excitation light. Specific illustrative practices, include detecting the transmission of light through the sample, detecting reflected light, detecting scattering light, and detecting emitted light. The detected light, in the form of the signal output from the sensor, can be analyzed by a CPU 174 provided in the device through known signal processing algorithms. Suitable sample analysis systems, employing a light source and an optical sensor or sensors, detects signals including light intensity at a given wavelength, phase or spectrum of the light, as well as location of the signal. For example, the flow induced testing system described in U.S. Pat. No. 6,318,191 and the multi-layer testing system described in U.S. Pat. App. Pub. No. US 2004/0105782 A1, both of which are incorporated herein by reference, describe suitable sample analysis systems.

Figure 14:
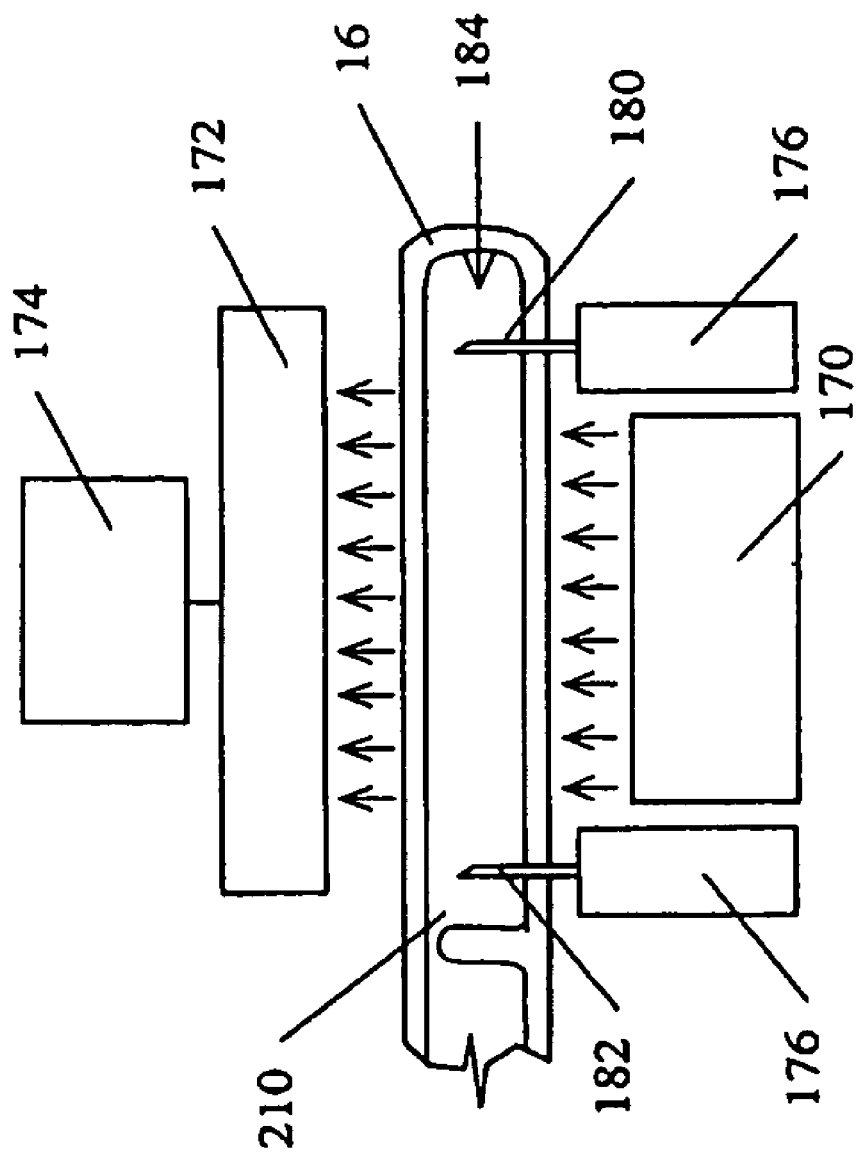
FIG. 14 is a side elevational view, in cross section, of a gel electrophoresis analysis unit of the present invention.

In the case of a PCR based assay, gel electrophoresis or capillary electrophoresis can be employed to analyze the nucleic acid sample, as illustrated in FIGS. 7 and 14. Suitable nucleic acid sizing gels include agarose and polyacrylamide. The gel 184 can be introduced to the sample vessel 16 during processing or, preferably, is pre-loaded into an analysis segment 210 of the sample vessel, as discussed in more detail below. The exemplary analysis unit 126 includes a light source 170 for illuminating the nucleic acid sample and the gel and an optical sensor 172 in the form of linear charge coupled device (CCD). Electrode activators 176 operate to insert a positive electrode 180 and a negative electrode 182 into the sample vessel 16. The positive electrode 180 and the negative electrode 182 are electrically connected to a voltage source, which creates a voltage difference between the electrodes. As nucleic acid products are negatively charged, the nucleic acid products within the sample will move through the gel 184 toward the positive electrode 180. The gel separates the sample components by size, allowing smaller components, such as nucleic acid products, to travel faster, and thus, further, than larger components. A suitable dye or fluorescent tag can be introduced to gel to identify the nucleic acid products. Light from the light source 170 can illuminate the dyed or tagged nucleic acid products in the gel and the optical sensor 172 can then identify the illuminated nucleic acid products. The output signal of the optical sensor 172 can be analyzed by CPU 174 according to known signal processing method to determine the presence, absence, quantity or other condition of the nucleic acid sample.

Alternatively, the nucleic acid sample can be analyzed in accordance with conventional nucleic acid analysis methods, such as, for example, chemiluminescence, fluorescently labeled primers, antibody capture, DNA chip, and/or magnetic bead detection methods.

One skilled in the art will appreciate that the processing units and the processing stations of the above-described exemplary embodiments of the sample processing device of the present invention can be arranged in any order depending on the sample being processed and the process being utilized. The sample processing device of the present invention may include any combination of the processing units and processing stations described herein, as well as additional processing units and processing stations that will be apparent to those skilled in the art upon reading this disclosure. Moreover, the sample processing device may include only a single processing unit, such as, for example, a reaction unit for thermal cycling a sample, or may include a only a single processing station, such as, for example, a processing station for displacing a specified volume of reagent or sample.

FIGS. 8-12 illustrate alternative embodiments of a reaction unit 250 for thermal cycling a sample according to the present invention. The reaction unit 250 can include one or more openings 252 for receiving one or more sample vessels 16. The embodiments illustrated in FIGS. 8-12 have three openings 252, permitting the simultaneous thermal cycling of up to three samples. The reaction unit 250 comprises three processing stations: a first processing station 254, a second processing station 256, and a third processing station 258. Thermal insulators 260A-260D are positioned between the processing stations and at the top of the first processing station 254 and the bottom of the third processing station 258.

Figure 8:
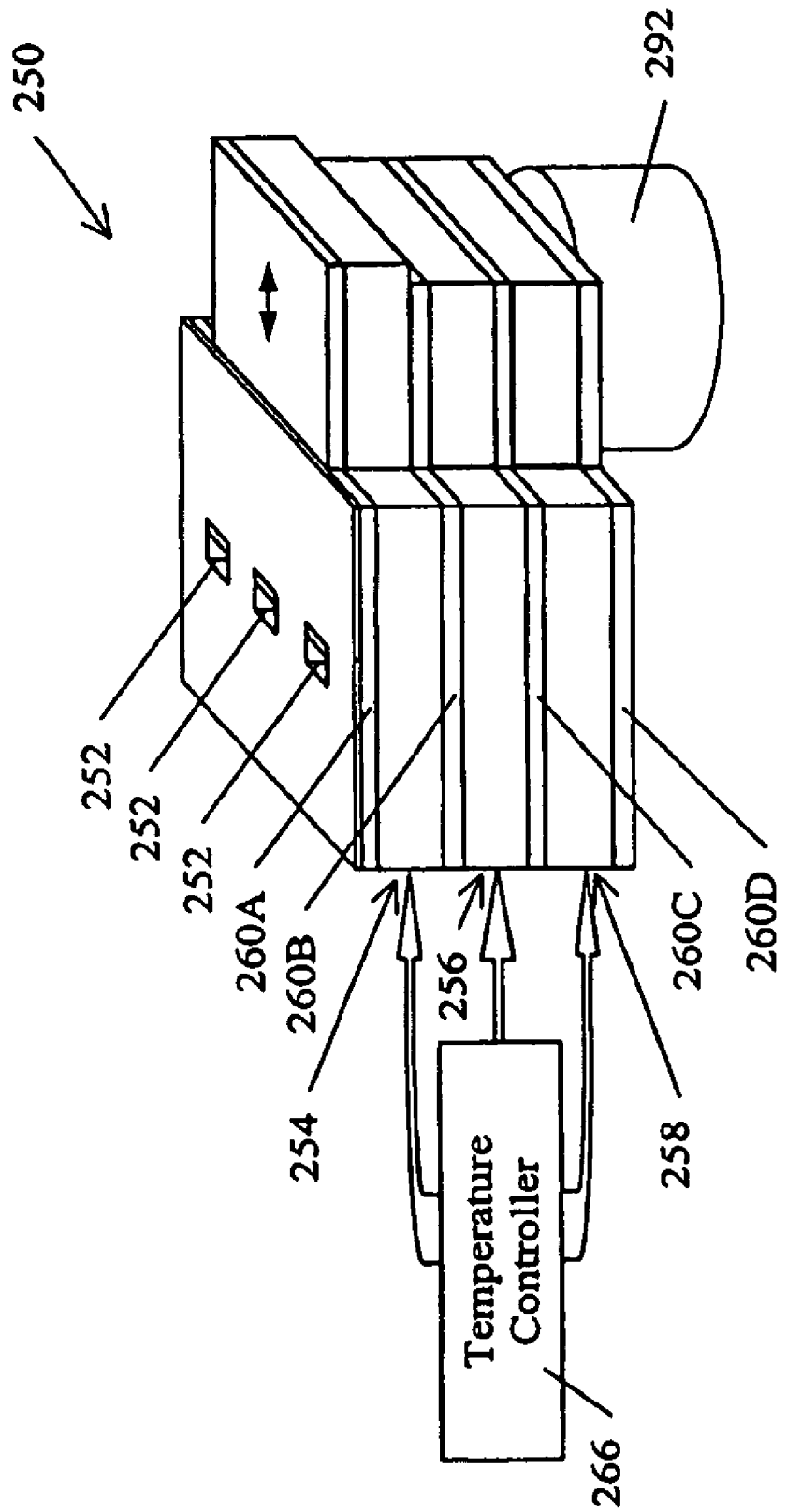
FIG. 8 is a perspective view of an embodiment of a thermal cycling processing unit according to the present invention.
Figure 10:
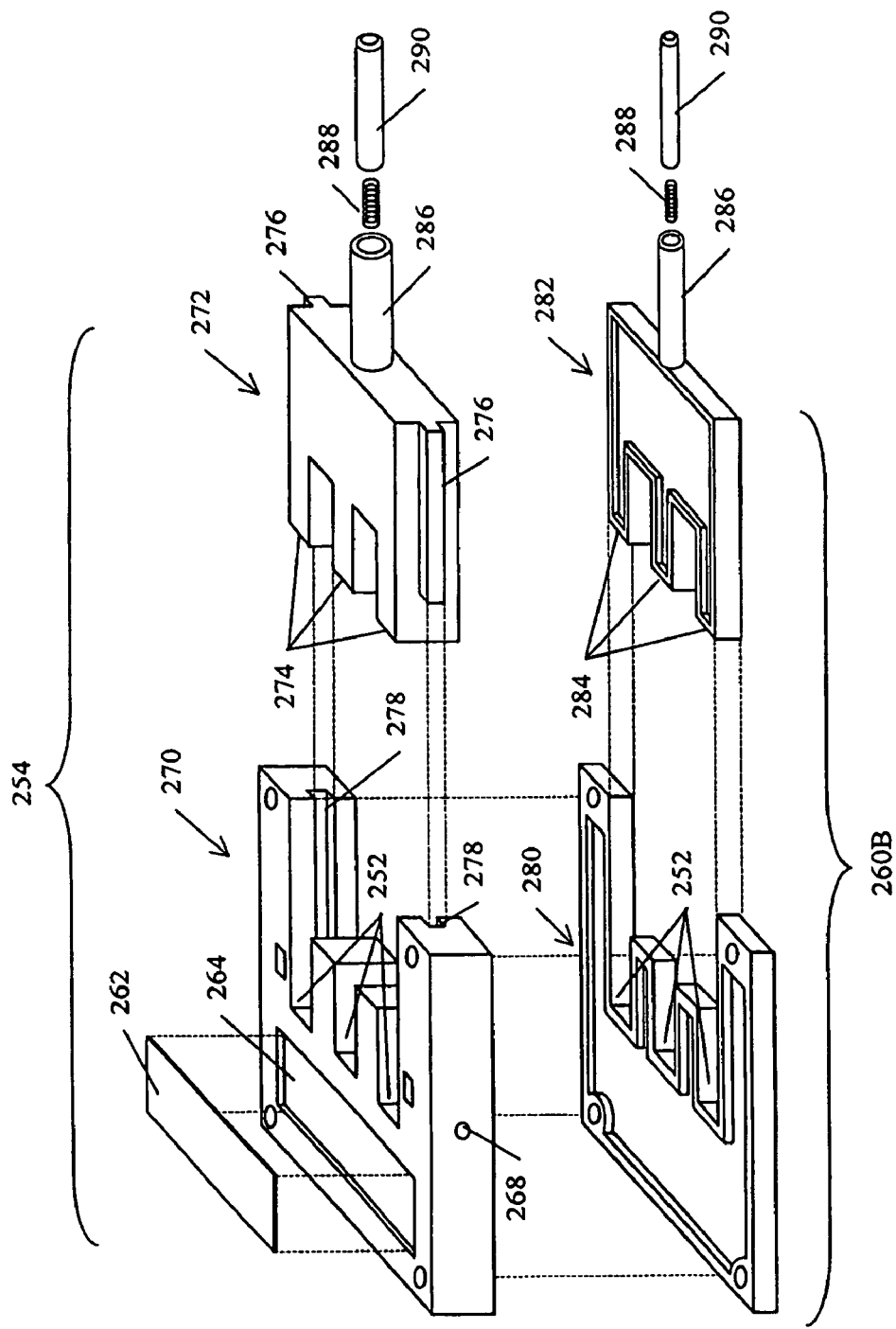
FIG. 10 is a partially exploded, perspective view of a processing station of the processing unit of FIG. 8, illustrating a heat block unit and an insulator block unit of the processing station.

Referring specifically to FIGS. 8 and 10, the first processing station 254, as well as the second and third processing stations 256 and 258, includes an embedded heat element 262 for transferring thermal energy to the sample vessel when the sample vessel is positioned within an opening 252. The heat element 262 can be a Kapton heater, a Nomex heater, a Mica heater, a silicone rubber heater or any other thermal energy transfer element suitable for delivering thermal energy. The heat element 262 can be seated in a recess 264 formed in the processing station 254 and secured to the processing station by an adhesive or other attachment means. The heat element 262 of each of the processing stations is preferably coupled to a temperature controller 266 for controlling the temperature of the heat element. One or more temperature sensors 268 can be positioned in the processing station 254 to measure the temperature of the processing station 254. The temperature sensor 268 can be coupled to the thermal controller 266 such that the temperature controller 266 can monitor and adjust the temperature of the processing station in a feedback control manner.

Figure 11:
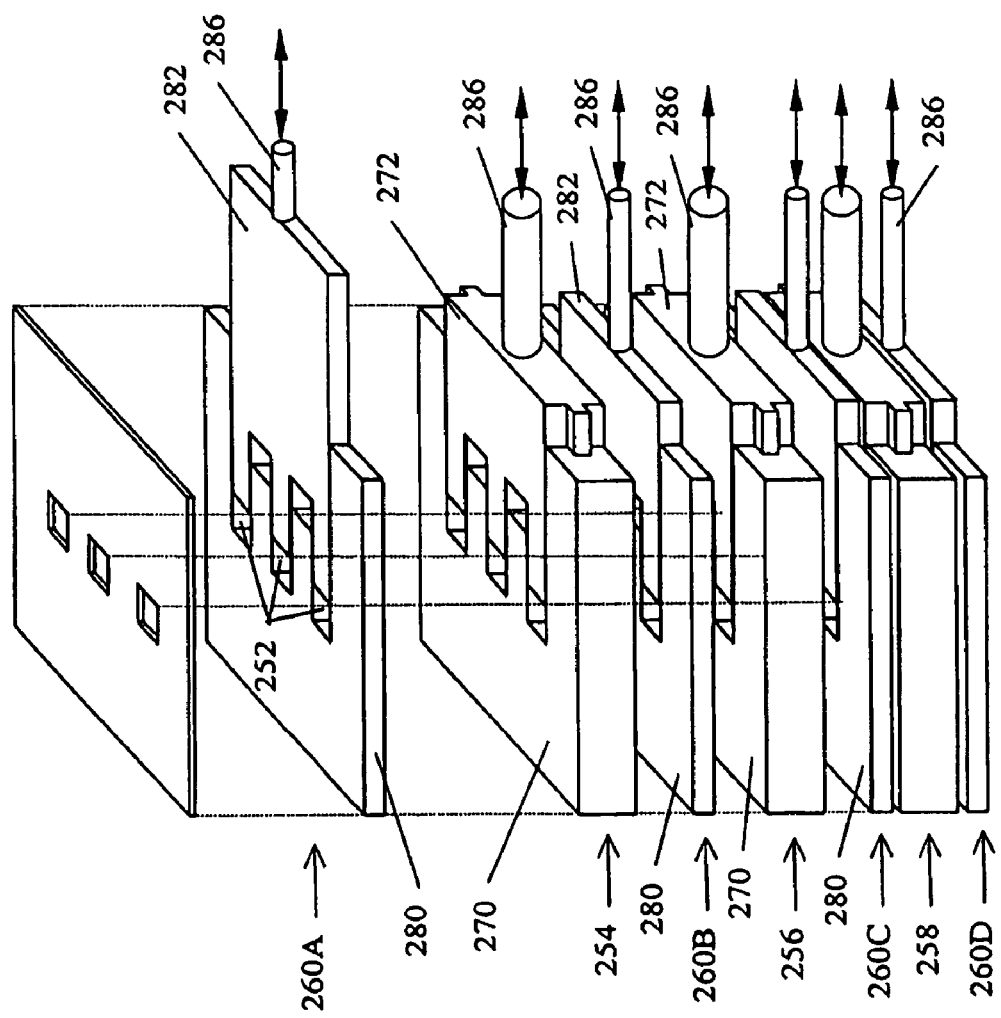
FIG. 11 is a partially exploded, perspective view of the processing unit of FIG. 8, illustrating a plurality of heating block units and insulator block units.
Figure 12:
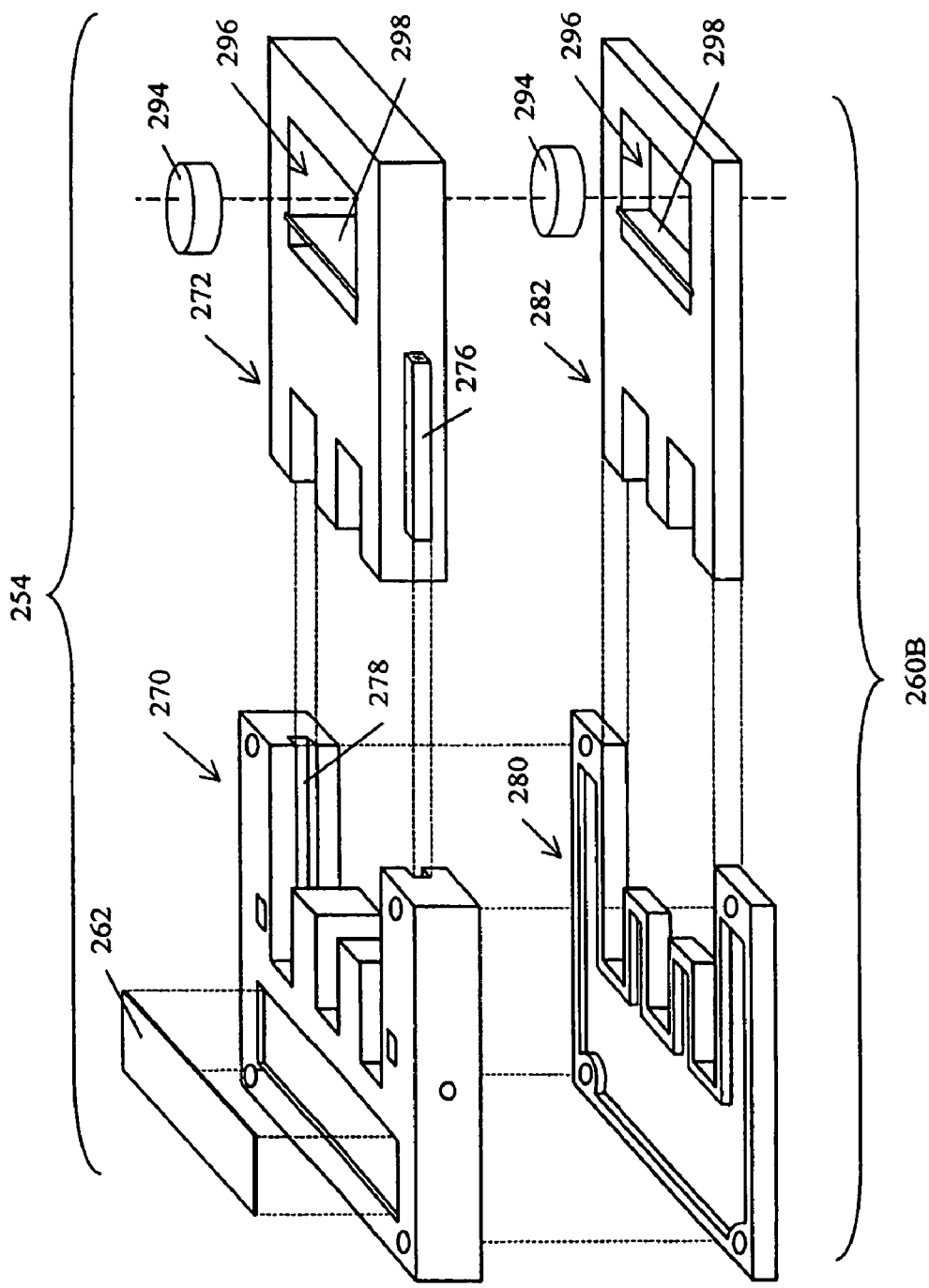
FIG. 12 is a partially exploded, perspective view of a processing station of an alternative embodiment of a processing unit according to the present invention.

Referring to FIGS. 10 and 11, each processing station comprises a stationary member 270 and a compression member 272 adapted to compress the sample vessel selectively within one or more of the openings 252 and thereby move the sample within the sample vessel. The compression member 272 is preferably complimentary in shape to the stationary member 270 and includes a plurality of finger-like closure elements or shutters 274 sized and shaped to slide within the openings 252. Guide rails 276 are positioned on either side of the compression member. The guide rails 276 are preferably sized and shaped to fit within grooves 278 formed in the side walls of the stationary member 270. The combination of the guide rails 276 and the grooves 280 allow the compression member 272 to reciprocate relative to the stationary member 270 to selectively open and close the openings 252.

Each thermal insulator 260 can be configured in a manner analogous to the processing stations. For example, the thermal insulator 260B comprises an insulator stationary member 280 and an insulator compression member 282 adapted to compress a sample vessel within one or more of the openings 252. The insulator compression member 282 includes a plurality of finger-like closure elements or shutters 284 sized and shape to slide within the openings 252 to selectively open and close the openings 252.

Figure 9:
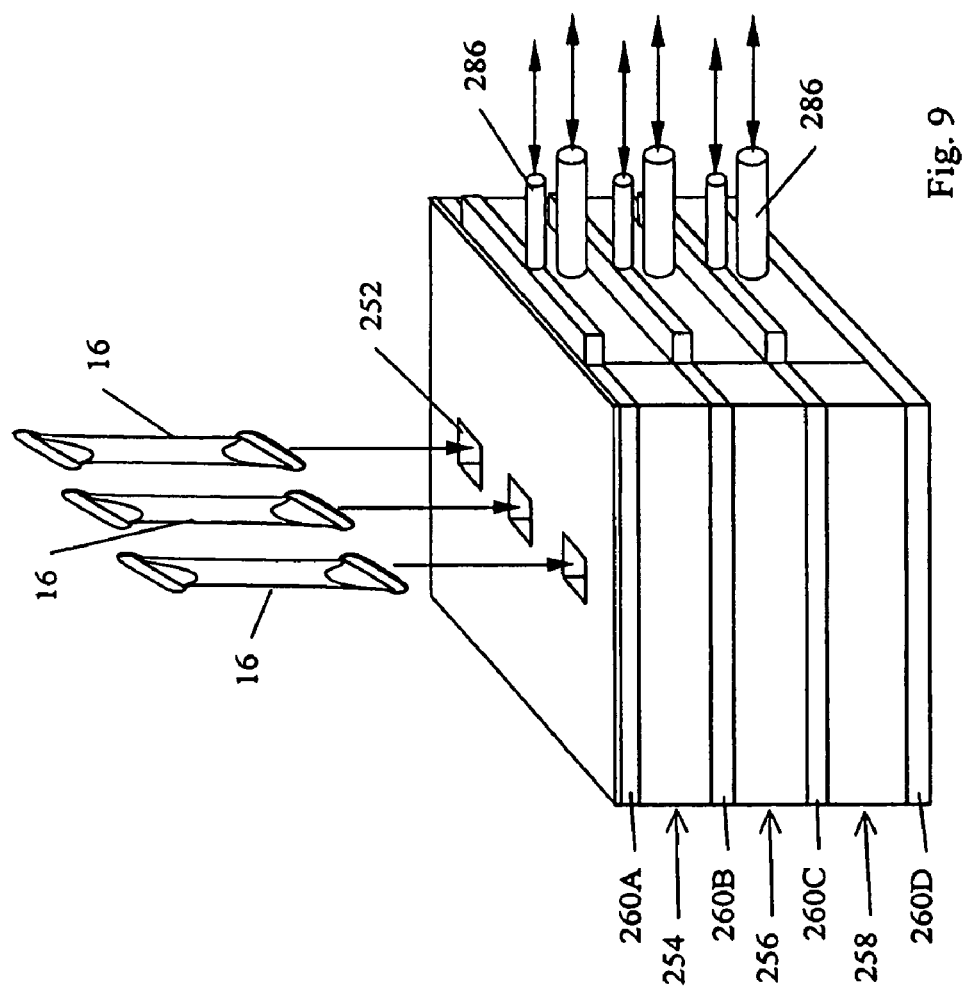
FIG. 9 is a perspective view of the processing unit of FIG. 8.

Each compression member 272 and insulator compression member 282 is coupled to a driver, such as an electromagnetic driver mechanism, as described above, or any other mechanism for imparting motion, preferably reciprocating motion, to the compression members. Each compression member can be coupled to an arm 286 for providing a connection between the compression member and the driver, as best illustrated in FIGS. 9-11. In one embodiment, illustrated in FIG. 10, the arms 286 are hollow tubes that receive coiled springs 288 and dowels 290. The springs 288 operate to bias the compression members 272, 282 in a direction away from the stationary member 270 and the insulator stationary member 280, respectively. An elastic element, such as the coiled spring used here, provides a simple mechanism for assisting the driver to regulate the compressing pressure applied to the sample vessel. The driver can be a motor 292 for driving a rotating shaft, as best illustrated in FIG. 8. The rotary motion of the shaft can be translated to reciprocating motion through cams 294 provided for each of the compression members 272 and 282. The cams 294 are coupled to the arms 286. The cams 294 can be configured to selectively open and close the compression members 272 and 282 in accordance with conventional cam design methods.

In one alternative embodiment of the reaction unit, the compression members 272 and 282 of each of the processing stations and insulators include holes 296 for receiving a cam 294 and a linear spring element 298. Spring elements 298 each operate to bias a respective compression member in a direction away from the corresponding stationary member. The cams 294, in combination with the springs 298, act to impart reciprocating motion to the actuators and regulate the compressing pressure on the sample vessel.

FIGS. 19A-19C illustrate a further embodiment of the reaction unit of the present invention. The reaction unit 350 includes nine openings 352 for receiving up to nine sample vessels simultaneously. The reaction unit 350 includes three processing stations: a first processing station 354, a second processing station 356, and a third processing station 358. Thermal insulators 360A-360D are positioned adjacent each of the processing stations and at the top of the first processing station 354 and the bottom of the third processing station. Top thermal insulator 360A and bottom thermal insulator 360D are movable independent of the first processing station 354 and the third processing station 358, respectively. Intermediate thermal insulators 360B and 360C are coupled to the first processing station 354 and the second processing station 356, respectively.

Each processing station comprises a stationary member 370 and a complementary compression member 372 adapted to compress the sample vessel selectively within one or more of the openings 352 and thereby move the sample within the sample vessel. Each stationary member 370 has a projection 374 aligned with one of the openings 352. The compression members 372 are each provided with a projection 376, positioned on an opposite side of the opening 352. When a compression member 372 is slid on the corresponding stationary member 370, the projections 374 and 376 engage and close the openings 352 therebetween.

Each compression member 372, as well as intermediate thermal insulators 360B and 360C, include an arm 380 coupled by a cam 384 to a rotary shaft 382. A stationary insulator member 362 is coupled, and aligned with an edge of each opening 352 on each stationary member 370. Each stationary insulator member 362 is inserted in each of the openings of a movable insulator compression member 360 to react to compression and open or close the opening. The shaft 382 is rotated by a stepper motor or a servo motor 386. The cams 384 translate the rotation of the shaft 382 into linear reciprocal motion, which is imparted to the arms 380 to effect selective opening and closing of the openings 352 and compression of the sample vessels therein.

Each arm 380 includes an inner shaft 390 received within an outer sleeve 392. A spring 394 is interposed between the inner shaft 390 and the respective compression member or thermal insulator. A second spring 396 is positioned on an opposite side of the respective compression member or thermal insulator. The spring 394 cooperates with the second spring 396 to allow the compression member or thermal insulator to "float" along the axis of the arm 380. In this manner, the arm 380 can apply sufficient force to the compression member or thermal insulator to compress the sample vessel within an opening 352 and, thereby, displace substantially all of the sample from the compressed portion of the sample vessel. An increase of pressure within the sample vessel, for example, from the compression of an adjacent portion of the sample vessel, however, can cause the sample to displace within the sample vessel through the compressed portion of the sample vessel, as the springs 394 and 396 will allow small axial movements of the compression member or thermal insulator.

Each stationary member 370 and compression member 372 can be provided with an embedded thermal energy transfer device 398 for each opening 352 to apply thermal energy to the sample vessel within the opening 352. In addition, the stationary member 370 and compression member 372 can include temperature sensors 399 associated with each energy transfer device 398 to monitor the temperature of the sample vessel.

FIGS. 15A and 15B illustrate embodiments of a sample vessel 16 according to the present invention. The illustrated sample vessel 16 is a closed tubule system that provides a disposable, single use container and reaction vessel for the sample. The sample vessel 16 can be constructed of a resiliently compressible, flexible, and ultra-high strength material, such as polyethylene or polyurethane. The sample vessel 16 can have a seamless, flattenable cross-sectional profile and thin-walled construction that is optimized for fast and uniform heat transfer, for maximum surface contact with the sample, and for high pressure resistance. Preferably, the walls are constructed to converge when the sample vessel is compressed in a direction perpendicular to the longitudinal axis of the sample vessel such that the volume of the compressed portion of the sample vessel decreases and the ratio of the surface area to the volume of the compressed portion increases, without fracturing of the sample vessel. In one illustrative preferred practice, the walls of the sample vessel 16 have a wall thickness of approximately 0.01 mm to 0.5 mm. Experimental results indicate that constructing a sample vessel having a wall thickness within this preferred range significantly increases the efficiency of heat transfer to the sample. In an alternative embodiment, a two-layer wall structure can be used, with the inner layer providing bio-compatibility, using material such as polyethylene or polyurethane, and the outer layer providing lower permeability, using material such as high density polyethylene or aluminum foil. In addition, the material selected to construct the portions of the wall of the sample vessel, such as a detection segment of the sample vessel 16, can be optically transmissive over a selected wavelength range to facilitate optical analysis of the sample within the sample vessel.

The sample vessel 16 can be divided into multiple segments by one or more pressure gates 32. In the case of PCR testing, for example, the sample vessel can be divided into a sample collection segment 205, a sample pretreatment segment 206, a sample reaction segment 208, and a sample analysis segment 210. The illustrated pressure gates 32 are internal to the tubule structure of the vessel 16 and provide a fluid tight seal between the segments of the sample vessel 16, under normal operating conditions. Preferably, the pressure gates 32 open upon the application of pressure greater than a certain value, for example, approximately 3 atmospheres. When external pressure is provided to one segment, the pressure gate 32 can open, allowing the sample to flow from the high pressure compartment to the low pressure compartment.

The sample vessel 16 can include a handling portion having a generally rigid construction to facilitate handling of the sample vessel. The handling portion can be coupled to one or more of the segments of the sample vessels used to contain the sample. For example, the handling portion can be a cylindrical sleeve constructed of a generally rigid material, such as a plastic or a metal, that is sized and shaped to fit over one or more of the segment of the sample vessel. In one embodiment, the cylindrical sleeve can be removable and replaceable. Alternatively, the handling portion can be a rigid segment, such as a rigid ring, positioned at an end of the sample vessel or between two segments of the sample vessel. In the embodiments illustrated FIGS. 15A and 15B, the handling portion is a segment of the sample vessel having an increased wall thickness. For example, the sample collection segment 205 and the sample pretreatment segment 206 have a wall thickness greater than the wall thickness of the reaction segment 208. The increased wall thickness provides sufficient rigidity to the sample collection segment 205 and the sample pretreatment segment 206 to facilitate handling of the sample vessel 16. In one embodiment, the wall thickness of the handling portion is greater than 0.3 mm.

The sample vessel 16 can include an instrument, such as a sampling pipette or a needle 107, for direct collection of the sample to be treated and analyzed within the sample vessel 16, as illustrated in FIG. 15A. The needle 207 can be positioned at one end of the sample vessel 16 and can be connected to the sample collection chamber 205 through a conduit 209 formed in the wall of the sample vessel 16. A needle cover 211 can be provided to secure the needle 207 prior to and after use. The needle cover 211 can be, for example, a penetrable rubber cover or a removable plastic cover.

In another embodiment, illustrated in FIG. 15B, a sampling instrument 214, such as a pipette, a stick, or a tweezer, can be coupled to a cover 212 that selectively closes the conduit or opening 209 formed in the wall of the sample vessel. The cover 212 can include a reservoir 216 for containing a reagent and a sample during sampling. For sampling, the cover 212 can be removed from the sample vessel to expose the sampling instrument 214. The sampling instrument 214 can be used to collect the sample, by pipetting, swabbing, or gathering the sample, for example, and then the sampling instrument 214 can be inserted into the sample collection segment 205 through the conduit 209. The sample can then be introduced to the sample collection segment 205 by compressing the cover 216 to displace the sample from the reservoir 216. Alternatively, the sample can be introduced to the sample collection segment 205 or to another segment of the sample vessel, depending of the segments present in the sample vessel, after collection by a separate instrument.

Sample vessel 16 can be particularly suited for PCR testing using the sample processing device of the present invention, as described above. For example, nucleic acid extraction can be performed within the sample pretreatment segment 206 of such a sample vessel 16. A cell lyses reagent, for example, GENERELEASER® from Bioventures, Release-ITT™ from CPG Biotech, or Lyse-N-Go™ from Pierce, or other extraction reagents can be introduced to the pretreatment segment 206 to extract nucleic acid from the initial sample. Extraction reagents can be stored within the pretreatment segment 206 or can be delivered to the segment. Additionally, one or more filters can be positioned within the pretreatment segment 206 of the sample vessel to separate nucleic acid from unwanted cellular debris.

After incubation of the sample for certain time period, a portion of pretreated sample can be moved into the reaction segment 208. For a reaction sample volume of approximately 5 µl-25 µl, a PCR reaction segment 208 of the sample vessel 16 according to one illustrative practice of the invention has a wall thickness, indicated by reference character t in FIG. 15A, of approximately 0.01 mm-0.3 mm, a diameter of less than approximately 6 mm, and a length of less than approximately 30 mm. PCR reagents, such as nucleotides, oligonucleotides, primers and enzymes, can be pre-packaged in the reaction segment or reaction segments 206, or can be delivered, for example, through the walls of the sample vessel using a needle, using for example, a reagent injector cartridge described below, before moving the sample into the segment.

A pre-packaged reagent storage segment 214 can be used to stored a pre-packaged reagent. Such a reagent storage segment can be formed between any two adjacent processing segments and may store any reagent needed for a reaction. For example, the reagent storage section 214 can store PCR reagents, while reagent storage sections 236 and 244, described below, may include detection reagents. If the reagent storage segment 214 is utilized, the sample vessel 16 can be compressed at the reagent storage segment 214 to displace the reagent into the pretreatment segment 206. Alternatively, the sample can be moved from the pretreatment segment 206, through the reagent storage segment 214 where mixing with the reagent, to the reaction segment 208.

Figure 16:
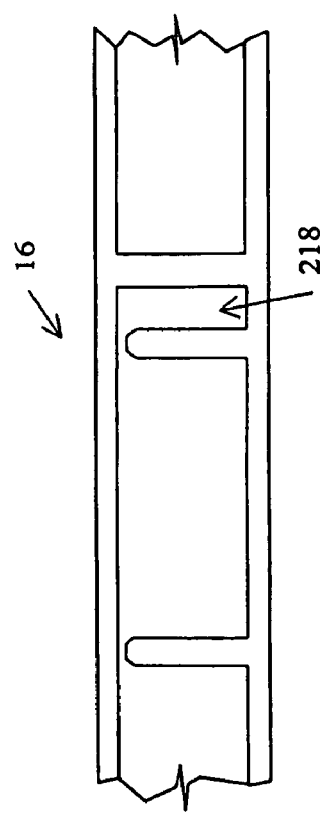
FIG. 16 is a side elevation view, in cross section, of a portion of a sample vessel according to the present invention, illustrating an injection channel formed in the sample vessel.
Figure 17:
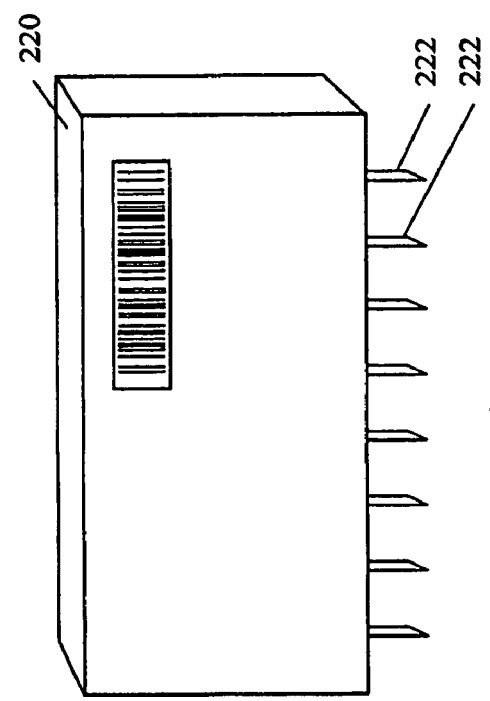
FIG. 17 is a side elevational view of a reagent cartridge according to the present invention.

A self-sealing injection channel 218 can be formed in the sample vessel to facilitate delivery of reagent or other materials to the sample vessel, as illustrated in FIG. 16. The illustrated self sealing injection channel 218 is normally substantially free of fluidic material and is capable of fluid communication with the adjacent segment in the vessel. An injection of reagent through an injection channel occurs preferably prior to moving any sample into the segment to avoid contamination. In addition, the sample treatment devices of the invention can utilize a reaction cartridge 220 with a single or multiple needles 222 in fluid communication with one or more reservoirs, as illustrated in FIG. 17. The reaction cartridge 220 can be used to inject or deposit reagent or other materials, simultaneously, or sequentially into multiple segments of the sample vessel. Suitable self-sealing injection channels and reagent cartridges are described in U.S. Pat. No. 6,318,191, incorporated herein by reference.

One skilled in the art will appreciate that while it may be preferable for the wall of the sample vessel to be uniform along the circumference and the longitudinal axis of the vessel, only a portion of the wall along the circumference and/or the longitudinal axis of the vessel need be resilient and compressible and have the preferred thickness to affect flattening of the sample vessel. Thus, the sample vessel need not have a uniform axial or circumferential cross-section.

PCR thermal cycling can be performed in the reaction segment 208 of the sample vessel 16. The thin walled, compressible construction of the sample vessel 16 greatly improves the rate and efficiency of thermal cycling. The construction of the sample vessel allows the vessel to deform or flatten readily, increasing thermal contact with the reaction unit of the device 10 and increasing surface/volume ratio of the sample within the sample vessel. As a result, the reaction mixture ramping rate is increased and thermal energy is more uniformly transferred to the sample.

PCR analysis can be performed in the sample vessel 16. For example, real-time detection methods can be used within the reaction segment 208; gel electrophoresis or other nucleic acid detection methods can be used within the analysis segment 210 to analyze the sample. In the case of gel electrophoresis, a gel can be introduced to the analysis segment 210 to facilitate gel electrophoresis, as described above in connection with FIG. 14.

In one preferred embodiment, illustrated in FIG. 15A, the analysis segment 210 is divided into two electrophoresis capillaries, namely, a sample capillary 230 and a control capillary 232, by a diametrically-central divider 234. Pressure gates 32 at either end of the capillaries control the movement of the sample and the reagents into both capillaries. Each capillary is filled with an electrophoresis gel such that gel electrophoresis can be performed simultaneously in both capillaries. A pair of electrodes 240, for both capillary 230 and 232, can be positioned within the walls of the sample vessel. A reagent storage segment 236 can be provided at the proximal end of the sample capillary 230 for storing reagent within the sample vessel prior to the sample entering the sample capillary 230. A control material can be stored in a control storage segment 242 positioned at the proximal end of the control capillary 232. A reagent can be stored in a reagent segment 244 positioned at the distal end of the capillaries and in communication with both the sample capillary 230 and the control capillary 232 for detection or display signal. The presence of the control capillary 232 facilitates detection and analysis of the sample by providing a basis of comparison for the sample analysis.

One skilled in the art will appreciate that the number of segments within the sample vessel is dependent upon the sample being processed and the processing methods being employed. For example, in the case of PCR testing, the number of segments within the sample vessel can be three or more. Alternatively, thermal cycling and analysis may be performed in one segment, reducing the number of segments to two. In certain cases, an isothermal nucleic acid amplification method, for example, only one segment may be necessary.

Figure 18:
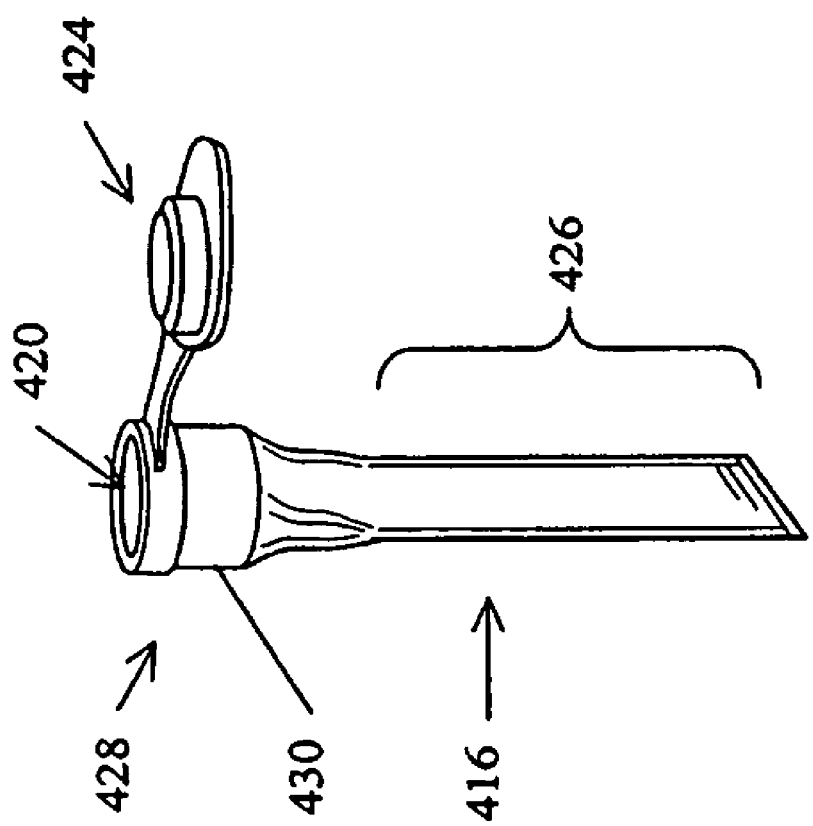
FIG. 18 is a side elevational view, in cross-section, of a sample vessel according to the present invention.

FIG. 18 illustrates a sample vessel 416 particularly suited for use in a multi-opening sample processing device such as, for example, the sample processing device illustrated in FIG. 6. The sample vessel 416 includes an opening 420 for receiving the sample, a cap or closure 424 for selectively closing and sealing the opening 420, and a sample containing portion 426 within which the sample can be treated. The opening 420 is formed in a handling portion 428 that is preferably constructed of a generally rigid or semi-rigid material, such as plastic or metal, to facilitate handling of the sample vessel 416. The handling portion 428 includes a collar 430 against which the cap 424 seats. Sample material can be introduced into the sample containing portion 426 of the sample vessel 416 through the opening 420. The collar 428 preferable tapers from a larger diameter to the smaller diameter of the sample containing portion 426. The sample containing portion 426 is preferable constructed of a resiliently compressible, flexible, and ultra-high strength material, such as polyethylene or polyurethane. The sample containing portion 426 can have a seamless, flattenable cross-section profile and thin-walled construction that is optimized for fast and uniform heat transfer, for maximum surface contact with the sample, and for high pressure resistance. In accordance with one embodiment, the sample containing portion 426 has a wall thickness of approximately 0.01 mm-0.3 mm. Preferably, the sample containing portion 426 of the sample vessel 416 is in a flattened state prior to introduction of the sample. Introduction of the sample to the sample containing portion 426 will cause the walls of the sample containing portion to separate and the volume of the sample containing portion to increase. Compression of a selected portion of the sample containing portion 426 can cause the sample to displace to another portion within the sample containing portion along the length of the sample vessel. The surface of the sample vessel can be chemically treated to reduce a surface effect on the reaction.

The embodiments of the sample vessel described herein in connection with FIGS. 14-16 and 18, are not limited to use with the embodiments of the sample processing device described herein. The sample vessel of the present invention may be used with any sample testing or processing system. Likewise, the sample processing device of the present invention is not limited to use with the sample vessels described herein. Other sample vessels may be used without departing from the scope of the present invention.

Certain changes may be made in the above constructions without departing from the scope of the invention. It is intended that all matter contained in the above description or shown in the accompanying drawings be interpreted as illustrative and not in a limiting sense.

The present disclosure is also directed to sample vessels that may be utilized to collect and process one or more samples in a closed system. Exemplary samples that may be collected, processed, or otherwise contained by the sample vessels disclosed herein include biological samples, such as blood, urine, saliva, tissue, cell suspensions, microbial organisms, viruses, nucleic acids, and oligonucleotides samples; soil; water; and any other sample materials that may be assayed using known assays. The term "collection" as used herein generally refers to the extraction or gathering of the sample from a sample source, the subsequent transfer of the sample into the sample vessel, or the combination of extraction and subsequent transferring of the sample into the sample vessel. Exemplary sample gathering may include pipetting, biopsying, swabbing, drawing a fluid sample or other methods for extracting a sample from a sample source. Exemplary sample sources may include humans or other animals, plants, water sources, cell cultures, food, other sample vessels, and chemical and biological assays. Sample sources may also include interim storage media, for example, test tubes, syringes, absorbent applicators and other interim storage media for containing a sample of interest. The term "processing" as used herein generally refers to the preparation, treatment, analysis, and/or the performance of other testing protocols or assays on a content of the sample vessel in one or more steps. Exemplary processing steps include, for example: displacing a content, e.g., the sample or a reagent, of the sample vessel within the sample vessel to, for example, adjust the volume of the content, separate content components, mix contents within the sample vessel; effecting a chemical or biological reaction within a segment of the sample vessel by, for example, introducing a reagent to the sample, agitating the sample, transferring thermal energy to or from the sample, incubating the sample at a specified temperature, amplifying components of the sample, extracting, separating and/or isolating components of the sample; or analyzing the sample to determine a characteristic of the sample, such as, for example, the quantity, count, volume, mass, concentration, or expression level of a molecule, a target, a content, a marker or an analyte, binding activity, nucleic acid sequence, or nucleic acid size or other analyte size, of the sample. One skilled in the art will appreciate that the forgoing exemplary processing steps are described herein for illustrative purposes only. Other processing steps may be employed without departing from the scope of the present disclosure.

FIGS. 20A-20C illustrate an exemplary embodiment of a sample vessel 1000 for collecting and processing one or more samples. The illustrated sample vessel 1000 comprises a tubule 1200 that provides a disposable, single use container and collection and processing vessel for the sample. The tubule 1200 may be constructed from any biocompatible material and may be manufactured by injection molding, insert molding, dip molding, blow-molding, extrusion, co-extrusion, lamination, assembling from a sheet material, or other processes generally used to manufacture medical devices and implants. The tubule 1200 may receive sample in solid or liquid form and, in certain embodiments, may be sized to collect and/or process sample volumes in the range of 2 microliters to 2000 microliters.

The tubule 1200 may be used with any known sample testing or processing system, including, for example, the systems described in U.S. Pat. No. 6,318,191, U.S. patent application Ser. No. 10/605,459, filed Sep. 30, 2003, which is a continuation of U.S. patent application Ser. No. 09/339,055, abandoned, and U.S. Pat. No. 6,780,617. Each of the aforementioned patents and patents applications is incorporated herein by reference.

In the exemplary embodiment illustrated in FIGS. 20 and 21, the tubule 1200 may include an opening 1400 for receiving a volume of sample material. The tubule 1200 may include a compressible segment 1600 having a wall 1800 constructed at least partially from a material having sufficient flexibility to permit compression of the opposed segments of the wall 1800 into contact. For example, the wall 1800 may be constructed to converge when the compressible segment 1600 of the tubule 1200 is compressed in a direction perpendicular to the longitudinal axis of the tubule such that the volume of the compressed segment 1600 of the tubule 1200 decreases, without fracturing of the sample vessel. The walls 1800 of the compressible segment 1600 may be constructed of a resiliently compressible, flexible, and ultra-high strength material, such as polyethylene, polyurethane, polyvinyl chloride, polypropylene, or any other plastic material suitable for biomedical or chemical assaying applications. In one illustrative embodiment, the walls 1800 of the compressible segment 1600 have a wall thickness of approximately 0.01 mm to 0.5 mm. Experimental results indicate that constructing a compressible segment of a tubule having a wall thickness within this range significantly increases the efficiency of sample processing, such as heat transfer to the sample and sample transfer between the segments, and detection. In the illustrated embodiment, the compressible segment 1600 of tubule 1200 extends the entire length of the tubule 1200. Alternatively, as discussed below, the tubule 1200 may include one or more discrete compressible segment 1600 spaced apart from one or more segments having different (e.g., non-flexible) properties.

In other exemplary embodiments, the tubule 1200 may comprise a multi-layer wall structure. For example, the tubule 1200 may include an inner layer providing bio-compatibility, using material such as polyethylene or polyurethane, and an outer layer providing lower permeability, using material such as high density polyethylene or a metal foil, such as aluminum foil or a metal deposition. One skilled in the art will appreciate that one or more additional layers may also be employed, depending on, for example, the sample type, the reagent(s) employed, and the assay(s) being performed.

The material selected to construct portions of the wall of the tubule 1200, for example an optional detection segment of the tubule 1200, can be optically transmissive over a selected wavelength range to facilitate optical analysis of the sample within the tubule 1200.

The sample vessel 1000 of the exemplary embodiment illustrated in FIGS. 20A-20C may comprise a general rigid container 2000 for receiving all or at least a portion of the tubule 1200. In the illustrated embodiment, the container 2000 is sized to receive the complete length of the tubule 1200. The container 2000 may be constructed of a material having increased rigidity compared to the material of the tubule 1200 to facilitate handling of the tubule 1200. In certain embodiments, the container 2000 may be constructed of a material having a lower permeability than the material of the tubule 1200. In the illustrated embodiment, the container 2000 is a glass vacuum tube. Suitable glass vacuum tubes are available under the trademark VACUTAINER® from Becton-Dickenson. The sample vessel 1000 can be used in a manner similar to a glass vacuum tube to collect a sample, such as a blood sample. A container 2000 may be optionally used with any of the tubule embodiments disclosed herein.

The sample vessel 1000 may comprise an interface 3000 that is in fluid communication with the opening 1400 in the tubule 1200. The interface 3000 may permit collection of the sample within the tubule 1200 by facilitating delivery of the sample material to the tubule 1200 through the opening 1400. In certain exemplary embodiments, the interface 3000 may include an instrument for collecting the sample form a sample source. In the exemplary embodiment illustrated in FIGS. 20A and 20B, the interface 3000 is a stopper 3200 that may be coupled to the tubule 1200 and may selectively seal the opening 1400 in the tubule 1200 to facilitate collection of the sample from a separate instrument. In the exemplary embodiment, the stopper 3200 is removably and replaceably connected to the rigid container 2000 and seals an opening 2200 in the container 2000. The stopper 3200 may include a first annular portion 3400 having an opening 3600 sized and shaped to receive the tubule 1200 in a fluid tight relationship. The first annular portion 3400 is further sized and shaped to engage the walls of the container in a fluid tight relationship. The stopper 3200 may include a second annular portion 3800 that has a diameter greater than the diameter of both the first annular portion 3400 and the container 2000. The opening 3600 extends through the second annular portion 38 to form an interface channel 3700. A penetrable, self-sealing portion 4000, such as a self-sealing membrane, may be provided to selectively seal the opening 3600 and, thus, permit selective transfer of the sample (from, for example, the sample collection instrument) through the interface channel 3700 into the tubule 1200. The self-sealing portion 4000 may be constructed of any biocompatible, resilient, self-sealing material that can be penetrated by a needle or other sample collection instrument. Suitable materials may include rubber and silicon. In certain embodiments, the stopper 3200 may be constructed completely from a biocompatible, resilient, self-sealing material such as rubber or an elastomeric polymer. The interface channel 3700 may taper or otherwise narrow through the cross-section of the stopper 3200 to provide a guide for a needle or other instrument transferring the sample to the tubule 1200.

Alternatively, the interface 3000 may include other mechanisms for selectively sealing the opening 1400 in the tubule 1200. For example, the interface may include a self-sealing elastomeric duckbill closure. Alternatively, the interface 3000 may include a valve for selectively closing and opening the interface channel 3700.

The sample vessel 1000 may include a clamp 5000 for compressing the compressible segment 1800 of the tubule to adjust the volume of the tubule 1200. The clamp 5000 may be configured to compress opposing wall portions of the compressible section 1600 into contact thereby dividing the tubule 1200 into two segments, 1600A and 1600B, as best illustrated in FIG. 20B. When the clamp 5000 is employed, the segment 1600A remains in fluid communication with the interface channel 3700 and segment 1600B is sealed from segment 1600A by the clamp 5000. Once the sample is delivered to the segment 1600A of the tubule 1200, the clamp 5000 may be removed, providing additional volume in the tubule 1200 that may permit future segmentation of the tubule and displacement of the sample within the tubule 1200 by compression of the tubule 1200.

The clamp 5000 may be positioned at any location along the longitudinal axis of the tubule 1200. Additional clamps may also be employed to divide the tubule into additional segments. In illustrated exemplary embodiment, the clamp 5000 is disk-shaped and includes a radial slot 5200 that is sized to receive the tubule 1800 in a compressed state. One skilled in the art will appreciate that other devices may used to compress and, thereby, divide the tubule 1200.

In certain exemplary embodiments, the tubule 1200 may be wholly or partially evacuated to place the lumen 4200 of the tubule 1200 under negative pressure, e.g., at a pressure less than atmospheric pressure, to facilitate fluid flow into the tubule 1200. Negative pressure can be generated by, for example, compressing the tubule 1200 to collapse the lumen 4200. An apparatus suitable for compressing the tubule is illustrated in FIGS. 36A-36C, described below. Alternatively the tubule 1200 may be compressed by hand. The tubule 1200 may also be manufactured to include a negative pressure.

In certain embodiments, the container 2000 may be wholly or partially evacuated to a negative pressure. For example, the container 2000 may be evacuated to inhibit loss of negative pressure within the tubule 1200 and to hold the shape of the tubule 1200 during storage.

A reagent may be pre-packaged in the tubule 1200 or can be introduced to the tubule 1200 after the sample is introduced to the tubule 1200. For example, a reagent can be introduced using a reagent injector cartridge associated with the sample processing system, by a needle, or by another device capable of fluid communication with the tubule 1200. The reagent can be, for example, an anticoagulant, a cell lyses reagent, a nucleotide, an enzyme, a DNA polymerase, a template DNA, an oligonucleotide, a primer, an antigen, an antibody, a dye, a marker, a molecular probe, a buffer, or a detection material. The reagent can be in liquid or solid form. In the case of a solid reagent, the reagent may be coated onto the walls of the tubule 1200.

In certain exemplary embodiments, the interface 3000 may include one or more chambers 44 that are in fluid communication with the tubule 1200 to selectively receive a volume of fluid, such as the sample material or a reagent, from the tubule 1200. In certain exemplary embodiments, the chamber 4400 may be evacuated or constructed to have a substantially small initial volume and may be expendable when receiving fluid. The chamber 4400 can be used as a waste container to receive and store overflow sample, wash buffer, or reaction mixture during the sample processing. For example, compressing a segment of the tubule 1200 may move a portion of the sample to the chamber 4400.

In the exemplary embodiment illustrated in FIGS. 21A-21C, for example, the stopper 3200 includes an annular chamber 4400 that is in fluid communication with the interface channel 3700 in the stopper 3200, and, thus, the tubule 1200, through a pressure gate 4800. In certain embodiments described herein, one or more pressure gates may be employed to selectively control the flow of fluid between segments, lumens, and other portions of the tubule, as well as between the tubule and external devices. For example, the illustrated pressure gate 4800 provides a fluid tight seal between the chamber 4400 and the interface channel 3700 under normal operating conditions. The pressure gate 4800 may open upon the application of a fluid pressure greater than a certain threshold pressure, for example, approximately 3 atmospheres. When a fluid pressure equal to or greater than the threshold pressure is applied to the pressure gate 4800, the pressure gate 4800 can open, allowing the sample or a reagent to flow from the high-pressure compartment, e.g., from the tubule 1200 or from the chamber 4400, to the low-pressure compartment. In certain embodiments, the pressure gate may be reversible, i.e., the pressure gate may be configured to re-close if the fluid pressure is reduced to value less than the threshold pressure. In other embodiments, the pressure gate may be irreversible, i.e., the pressure gate may be initially closed and may remain open once opened. For example, once a threshold pressure is exceeded the irreversible pressure gate remains open, even if the pressure applied to the pressure gate is reduced to below the threshold pressure. One example of an irreversible pressure gate is the pressure gate described below in connection with FIGS. 22A-22B.

In the illustrated embodiment of FIGS. 21A and 21B, the pressure gate 4800 is a slit formed in the stopper 3200 between the interface channel 3700 and the chamber 4400. The material forming the stopper 3200 may be selected to be sufficiently flexible and resilient to allow the slit to open at the threshold pressure and to close at pressures lower than the threshold pressure.

A label 6000 identifying the sample within the sample vessel 1200 may be attached to the interface 3000, the container 2000, or the tubule 1200. The label 6000 can be a bar code or other indicia for identifying the sample.

FIGS. 22A and 22B illustrate another exemplary embodiment of a sample vessel 10000. The sample vessel 10000 comprises a tubule 11200, which can be analogous in construction to the tubule 1200, having a plurality of lumens 14200A and 14200B. The plurality of lumens 14200A and 14200B can be separated by a pressure gate 148 that permits selective fluid flow between the lumens 14200A and 14200B. FIG. 22A illustrates the pressure gate 14800 in a closed position and FIG. 22B illustrates the pressure gate in an open position that permits fluid flow between the lumens.

In the exemplary embodiment, the lumens 14200A and 14200B are parallel to each other and extend in a direction generally parallel to the longitudinal axis of the tubule 1200. One skilled in the art will appreciate that other lumen orientations are possible. The lumens 14200A and 14200B may be uniform in size (e.g., diameter, width, length) and shape or, alternatively, the lumens 14200A and 14200B may be different in size and shape, as in the illustrated embodiment. For example, in the illustrated embodiment, the lumen 14200B has a smaller diameter than the lumen 14200A. Although two lumens are illustrated in the exemplary embodiment, one skilled in the art will appreciate that the tubule 1200 may be constructed of any number of lumens.

The pressure gate 14800 in the present embodiment is coextensive with the lumens 14200A and 14200B, i.e. the pressure gate 14800 extends along the entire length of the lumens. Alternatively, the pressure gate 14800 may extend along only a portion or portions of the lumens, particularly in embodiments in which the tubule 1200 is segmented into discrete longitudinally extending segments, as in the case of the embodiment illustrated in FIGS. 26A-26C. In such embodiments, one or more pressure gates may be provided between adjacent lumens.

In the exemplary embodiment, the opposed portions of the wall 11800 of the tubule 11200 are compressed into contact to form a longitudinally extending seam 17000 that divides the tubule 11200 into two lumens, lumens 14200A and 14200B. In addition to dividing the tubule 11200 into multiple lumens, the seam 17000 may further provide an irreversible pressure gate, pressure gate 14800, between the lumens 14200A and 14200B. The seam 17000 may be formed by mechanically clamping or otherwise compressing a cylindrical tubule or by applying vacuum pressure to the interior of a cylindrical tubule. Alternatively, the seam 17000 may be formed during manufacturing of the tubule by, for example, extrusion, molding, or lamination processes. The opposed wall portions that are compressed into contact to form the seam 17000, and the pressure gate 14800, may be bonded together by mechanical or chemical bonding, by heating sealing, for example, by bringing hot surfaces into contact with the tubule wall immediately after extrusion, by ultrasonic welding, by mechanical interlocking, or both other connection mechanisms, to create the irreversible pressure gate 14800.

The pressure gate 14800 is initially in a closed configuration that inhibits fluid flow between the lumens 14200A and 14200B. The pressure gate 14800 may open by separating the compressed opposed walls forming the pressure gate 14800. Applying a threshold pressure to the pressure gate 14800, as described above, may open the pressure gate 14800. Alternatively, energy may be applied to the pressure gate 14800 to weaken the bond between the compressed opposed walls. For example, thermal energy or light, e.g., ultra-violet light, may be applied to the pressure gate 14800 or to selected portions or all of the tubule 11200. The threshold pressure and/or the amount energy to open the pressure gate 14800 may vary depending on the type and strength of the bond. Alternatively, the bond between the compressed opposed wall portions may be weakened or broken by chemical reaction with reagent or the sample.

In certain exemplary embodiments, one or more of the lumens may include one or more reagents. Reagents may be provided to one or more lumens prior to sample collection, e.g., one or more reagents pre-packaged with the tubule, or after sample collection. In the exemplary embodiment illustrated in FIGS. 22A and 22B, for example, a reagent may be provided in lumen 14200B. Lumen 14200A may be utilized for sample collection and processing. Sample collection may occur with the pressure gate 14800 in a closed configuration, as illustrated in FIG. 22A. Upon transfer of the sample to lumen 14200A, the pressure gate 14800 may be opened automatically due to release of pressure within the lumen 14200A, or selectively by applying energy to the pressure gate and/or a threshold fluid pressure. In other embodiments, the lumen 14200A or 14200B may be compress to provide the threshold pressure. Upon opening the pressure gate 14800, the reagent(s) can mix with and interact with the sample in the lumen 14200A, as illustrated in FIG. 22B. Automatic release of the pressure gate 14800 and mixing of the reagent with the sample may be beneficial in certain applications, such as the mixing of an anticoagulant with a blood sample.

FIG. 23 illustrates another embodiment of a multi-lumen tubule 11200 that includes three lumens, namely a first lumen 14200A, a second lumen 14200B, and a third lumen 14200C. Each lumen may be separated a pressure gate 14800, for example, an irreversible pressure gate, as described above. Each of the lumens 14200A, 14200B, and 14200C may be provided with one or more reagents and/or may be used for sample collection and processing. For example, second lumen 14200B may be provided with one or more prepackaged reagents and first lumen 14200A may be used for sample collection and processing. Upon sample collection in first lumen 14200A, pressure gate 14800A may be opened allowing fluid communication between the second lumen 14200B and the first lumen 14200B. FIG. 23 illustrates the pressure gate 14800A in an open configuration. Lumen 14200C may be utilized as an injection channel for receiving one or more reagents, typically, but not necessarily, after sample collection in first lumen 14200A. The lumen 14200C may be free of sample material until pressure gate 14800A is transitioned to an open configuration. FIG. 23 illustrates pressure gate 14800B in a closed configuration that inhibits fluid communication between third lumen 14200C and first lumen 14200A. Reagent may be delivered to the third lumen 14200C by a needle 19000, such as a needle from a reagent injection cartridge, or by other instruments that can penetrate the lumen or otherwise provide fluid communication between a reagent source and the lumen 14200C. The lumen 14200C may be free of sample and reagent material until reagent is injected to avoid cross contamination of the injection needle 19000. The portion of the wall 11800C proximal the third lumen 14200C may be constructed of a resilient, self-sealing material to facilitate re-sealing of the wall 11800 after penetration to deliver reagent.

One or more lumens of the tubule 11200 may include a reinforced wall portion 17100, as illustrated in FIG. 24. The reinforced wall portion 17100 may have an increased wall thickness compared with the remainder of the tubule wall 11800 to facilitate needle penetration and re-sealing. For example, the reinforced portion may have a wall thickness of approximately 1 mm to 5 mm greater than other portions of the wall. The reinforced portion 17100 may be constructed from a different material, having increased strength and/or resiliency, for example, than the remainder of the tubule wall 11800. Needle guides 17200 may be provided to direct needle penetration and inhibit tearing of the tubule wall 11800.

FIGS. 25A-25E illustrate another exemplary embodiment of a multi-lumen tubule 11200 that includes a pair of parallel lumens, namely first lumen 14200A and 14200B. In the illustrated embodiment, the lumens 14200A and 14200B are connected parallely by a thin layer fluid channel 17600 in the form of a slit opening that extends the length of the tubule 11200. Although one fluid channel is illustrated, additional fluid channels may be provided. The fluid channel 17600 permits the sample to be moved between the first lumen 14200A and the second lumen 14200B and to occupy both lumens simultaneously. For example, during sample collection, portions of the sample, or the entire sample, can be transferred from the opening 11400 along the length of the first lumen 14200A, through the fluid channel 17600, and along the length of the second lumen 14200B. FIGS. 25B-25E illustrate the flow of a sample, in fluid form, through the first lumen to the end of the first lumen due to relatively low flow resistance of the lumen relative to the fluid channel 17600 (FIG. 25B), through a portion 17400 of the fluid channel 17600 distal to the opening in the first lumen 14200A (FIG. 25C), along the fluid channel 17600 and through the second lumen 14200B (FIG. 25D) to fill both lumens (FIG. 25D). In embodiments in which a solid reagent is packed into the lumens 14200A and/or 14200B of the tubule 11200, flow of the sample through the lumens via the fluid channel 17600 can facilitate mixing of the solid reagent with the sample. For example, in the case of blood samples, the inventors have determined that by allowing the blood sample to flow through the first lumen 14200A and the second lumen 14200B via the fluid channel 17600 can improve mixing of the sample with an anticoagulant coated on the inner walls of the two lumens.

FIGS. 26A-26C illustrate another exemplary embodiment of a multi-lumen tubule 11200 having three parallel lumens, namely a first lumen 14200A, a second lumen 14200B, and a third lumen 14200C. In the exemplary embodiment, each lumen of the tubule 11200 is divided into a plurality of longitudinally extending segments 18000. For example, the third lumen 14200C, illustrated in cross-section in FIG. 26B, includes five segments 18000A-E. Each of the segments 18000 can be used for one or more sample collection and/or sample processing steps, including the processing steps described above. In PCR (polymer chain reaction) testing, for example, one segment may used for sample collection, one segment may be used for sample pretreatment, e.g., nucleic acid extraction, one or more segments may used for sample processing, e.g., thermocycling, and one or more segments may be used for sample analysis. Any number of segments may be provided. In addition, one or more segments may be used to store reagent or as an injection channel for the delivery of reagent. The number of segments may be varied depending of the sample being processed and the processing steps selected.

Each of the segments 18000 may be separated by a seal 18200 that provides a temporary or permanent fluid seal between adjacent segments 18000. A seal 18200 may be a pressure gate, such as the reversible and irreversible pressure gates described above. Alternatively, a seal 18200 may be formed by bonding or fusing of compressed opposed wall sections of the tubule. The seal 18200 may be formed by applying energy, such as thermal energy or RF energy, by ultrasonic welding, or by using a bonding agent. A clamp may also be applied to the exterior of the tubule to compress the wall of the tubule and form a seal separating the segments in the tubule. For example, the clamp may be an electro-mechanical clamping mechanism as described below in connection with FIG. 29. Any other mechanism for provided an external compressive force on the tubule may be employed as the clamping mechanism. One or more clamps may be provided as part of the sample processing system used to process the sample within the tubule 11200. The segments may be connected by one or more micro-fluidic flow channels that provide selective fluid connection between the segments, as described below. A seal 18200 may be a filter disposed within the tubule to separate selected components of a fluid within the tubule from other segment or components of the fluid within the tubule.

In the illustrated exemplary embodiment, the interface 3000 for facilitating delivery of the sample to the tubule 11200 includes a needle 18400 for direct collection of the sample to be processed with the sample vessel 10000. The needle 18400 is positioned a proximal end of the tubule and is fluid communication with an opening in the tubule 11200. In the illustrated exemplary embodiment, the needle 18400 is in fluid communication with an opening in the first lumen 14200A, however, the needle 18400 may be connected to any one or all of the lumens 14200 of the tubule 11200. A removable and replaceable needle cover 18600 may be provided to secure the needle 18400 prior to and after use. Alternatively, the needle cover 18600 may be connected by a hinge, as shown in FIG. 27, or by another mechanism that allows to the cover 18600 to be moved into and out of position about the needle 18400. A needle safety mechanism may be coupled to the needle and the sample vessel.

FIG. 28 illustrates another embodiment of the cover 18600 in which the sample collection instrument, e.g., the needle 18400, is connected to the cover 18600. In the illustrated exemplary embodiment, the proximal end 18400A of the needle 18400 may be used for sample collection from a sample source and the distal end 18400B of the needle 18400 may be used to provide a fluid connection with an opening in the tubule 11200 through interface 3000. For example, the distal end 18400B may be used to penetrate a self-sealing membrane 4000 provided in the interface 3000. In another embodiment, a cover 19000 may include a sample instrument in the form of a needle 18400 and may have a compressible portion in fluid communication with the needle to facilitate drawing a fluid sample into the needle 18400 and transferring the sample to the sample vessel 11000. Cover 19000 may be particularly useful as a finger prick for collection a blood sample.

FIG. 29 illustrates a processing station 30000 of an exemplary sample processing device, such as a sample processing device described in U.S. Pat. No. 6,318,191 and U.S. patent application Ser. No. 09/782,732, filed Feb. 13, 2001. The exemplary processing station 30000 includes multiple compression members, namely first compression member 30200A, second compression member 30200B, and third compression member 30200C. Each compression member 30200 is adapted to compress a sample vessel, for example, the tubule 1200 of sample vessel 1000 described above, and thereby displace the contents of the sample vessel, e.g. reagent or sample, within the sample vessel. Although the exemplary processing station 30000 is illustrated in connection with sample vessel 1000, one skilled in the art will appreciate that any of the sample vessels disclosed herein may be used in with the exemplary processing station 30000. A plurality of compression members 30200 may be oriented parallel to the longitudinal axis of the tubule 1200, as illustrated in FIG. 29A. Alternatively, a plurality of compression members 30200 may be oriented transverse to the longitudinal axis of the tubule, i.e., oriented latitudinally, as illustrated in FIG. 34B described below, or in other orientations depending on the compression configuration desired. A driver may be coupled to one or more of the compression members 30200 to selectively move the compression member into contact with the sample vessel. The driver can be, for example, an electromagnetic actuating mechanism, a motor, a solenoid, or any other device for imparting motion on the compression members 30200. A stationary member 30400 or another compression member may be provided opposite compression member 30200.

A compression member 30200 may be employed to compress a portion of the wall 1800 of the tubule 1200 into contact with another portion of the wall 11800 of the tubule 1200 to form a seal in the tubule 1200 and thereby divide the tubule 1200 into multiple segments. In alternative embodiments, a compression member 30200 may compress a portion of the wall 1800 of the tubule 1200 into proximity with another portion of the wall 1800 of the tubule 1200 to form a micro-fluidic channel 30600 between segments of the tubule 1200. For example, in the embodiment illustrated in FIG. 29, compression member 30200B compresses a portion of wall 1800 into proximity with another portion of the wall to create a micro-fluidic channel 30600 that connects a first segment 18000A and a second segment 18000B of the tubule 1200. The width of the micro-fluid channel 30600 may be adjusted by displacing the compression member 30200B towards or away from the tubule 1200. Micro-fluid channels may be formed having a gap less than 200 microns, preferably 10 to 30 microns.

The compression members 30200 may be arranged in a variety of orientations to compress the tubule 1200 into a variety of configurations. For example, in FIG. 29B, the width of the micro-fluidic channel 30600 extends across the entire width of the tubule 1200. Such a compressed configuration may be formed by a compression member 30200B having a planar compression surface 30800 for engaging the tubule 1200 that is sized to engage the entire compressed wall surface of the tubule. In other embodiments, the size or shape of the compression surface 30800 may be varied and the number and orientation of compression members 30200B may be varied. For example, FIG. 30A illustrates a compressed tubule 1200 having a centrally located flow channel 30600 that may be formed by a compression member 30200 having a groove formed on the bottom surface thereof or by three compression members 30200 aligned transverse to the longitudinal axis of the tubule 1200. A centrally positioned compression member may compress wall portion 1800A into proximity with an opposed wall portion, while a pair of compression members, one on either side of the central compression member, may compress side wall portions 1800B and 1800C, respectively. FIG. 30B illustrates a compressed tubule 1200 having a centrally located lumen 30600 formed by compressing the tubule 1200 into a non-planar configuration. In this illustrated embodiment, a triangular profile flow channel is formed, which inherently forces a cell or particle to flow through the central line of the channel, thus reducing the need to regulate the tolerance in forming the flow channel. FIG. 30C illustrates a compressed tubule 1200 having a flow channel 30600 formed off-set from the center of the tubule 1200. In the illustrated embodiment, the flow channel is formed on a lateral edge of the tubule 1200.

At least a portion of the wall of the tubule 1200 may be optically transparent to allow monitoring or detection of the sample or reaction. The transparent portion of the wall may be located in the flow channel section, thus allowing the monitoring of sample or reaction under flow or through a thin layer of liquid, for processes such as counting cells, reaction hybridization, or detection, for example, microarray spots.

One skilled in the art will appreciate that while it may be desirable in certain applications for the wall of the tubules disclosed herein to be uniform along the circumference and the longitudinal axis of the tubule, only a portion of the wall along the circumference and/or longitudinal axis of the tubule need be resilient and compressible. Thus, the tubule need not have a uniform cross-section, either along the longitudinal axis or transverse to the longitudinal axis. In certain exemplary embodiments, for example, a section of the wall of the tubule may be formed of a material selected to provide a property distinct from a property of another section of the wall. Exemplary properties that may be varied include permeability, flexibility, hardness, resiliency, optical transparency, biocompatibility, surface smoothness of the inner wall, and surface chemistry of the inner wall, for example the hydrophobic or hydrophilic properties of the inner wall surface. Surface properties may be rendered by coating with a layer of material, such as a thermoset urethane aired by UV energy or other cross linking methods.

FIGS. 34A and 34B illustrate an exemplary embodiment of a sample vessel 1000 in the form of a tubule 1200 having wall sections 1800A that are formed of a material selected to provide a property distinct from a property of a plurality of other wall sections 1800B of the tubule 1200. Wall sections 1800A may be opposed to one another, as illustrated, or positioned at other positions in the cross section of the tubule 1200. Wall sections 1800A may similar in size, shape and material properties, as illustrated, or may vary in size, shape, and material properties from one another. In the illustrated embodiment, wall sections 1800A are selected from a material having sufficient flexibility to permit compression of the tubule 1200, as illustrated in FIG. 34B. Wall sections 1800B are formed of a material having increased rigidity compared to the material of wall sections 1800A. In the illustrated embodiment, wall sections 1800B preferably have sufficient rigidity to resist flexing during compression and thereby maintain a planar configuration. Wall sections 1800B may be opposed to one another, as illustrated, or positioned at other positions in the cross section of the tubule 1200. Wall sections 1800B may be similar in size, shape and material properties, as illustrated, or may vary in size, shape, and material properties from one another. In the illustrated embodiment, the wall sections 1800A and 1800B are spaced latitudinally, i.e., about the circumference of the tubule 1200 and transverse to the longitudinal axis. Wall sections 1800A and 1800B are interposed between one another in an alternating arrangement about the circumference of the tubule 1200. Wall sections 1800A and 1800B may be formed from the same material or a different material. For example, wall sections 1800A may be formed of a relatively low durometer polyurethane, for example, in the range of from 40A to 90A depending on thickness, and wall sections 1800B may be formed of a polyurethane having a relatively higher durometer, for example, in the range of from 40D to 90D depending on thickness. A tubule having wall sections of varying properties may be manufactured by conventional extrusion, co-extrusion, injection molding, insert molding, dip molding, blow molding, transfer molding, or lamination processes.

During compression of the tubule 1200 illustrated in FIGS. 34A and 34B, the wall sections 1800A flex allowing a first wall section 1800B to be moved into proximity or contact with second wall section 1800B'. Wall sections 1800B may provide improved sealing surfaces due to the increased rigidity compared with wall sections 1800A. In addition, walls sections 1800B permit the formation of a precisely defined micro-fluid flow channel 30600, as illustrated in FIG. 34B. The increased rigidity of the wall sections 1800B allows for the formation of a smaller and more uniform flow channel than more flexible wall sections. FIG. 34B illustrates the formation of a micro-fluidic flow channel 30600 between segments 18000A and 18000B of the tubule 1200. In the illustrated embodiment, the compression members 30200A-C are oriented transverse to the longitudinal axis of the tubule to form a flow channel 30600 that extends latitudinally, i.e., transverse to the longitudinal axis, between first segment 18000A and second segment 18000B.

In other exemplary embodiments, the number of wall sections of differing properties may be varied. For example, a single wall section 1800B having increased rigidity may be provided or three or more wall sections having increased rigidity may be provided.

In certain exemplary embodiments, a flow channel 30600 may be pre-formed in a section of the wall 1800 of the tubule as illustrated in FIGS. 31 and 32A-B. The pre-formed flow channel 30600 may be a groove 31600 formed in a wall section of the tubule 1200. The groove 31600 may be formed by scoring or etching the wall 1800 of the tubule 1200 or may be formed during the extrusion or molding of the tubule 1200. The groove 31600 in the illustrated embodiments extends longitudinally, however, the groove 31600 may be formed in any direction, including latitudinally. More than one groove 31600 may be provided. The groove 31600 may have a variety of cross-section shapes and sizes. In the embodiment illustrated in FIG. 31, the groove 31600 has a triangular cross-section. In the embodiment illustrated in FIGS. 32A-32B, the groove 31006 has a rectangular cross-section. The cross-sectional size of the groove 31600 can be selected based on desired shear rate profile of the flow channel 30600.

The groove 31600 may be formed in any section of the wall 1800 of the tubule 1200. For example, the groove 31600 may be formed in a wall section 1800B having increased rigidity compared to other wall sections of the tubule 1200, as is the case for the illustrated embodiments of FIGS. 31 and 32A-B. During compression of the tubule 1200, as illustrated in FIG. 32B, the wall section 1800B contacts wall section 1800B' to provide a fluid tight seal. Groove 31600 provides a flow channel 30600 that extends longitudinally through the fluid tight seal.

FIGS. 33A and 33B illustrate an exemplary embodiment of a sample vessel 40000 comprising a tubule 41200 having a plurality of flow channels 30600 and one or a plurality of depressions 40800 formed on an interior wall surface 41000 of the wall 41800 of the tubule 41200. Each depression 40800 can form a micro-cup during compression of the tubule 41200 that can hold a fixed volume of sample or reagent. The volume of a depression forming a micro-cup can be from 0.1 microliter to 10 microliter, preferably, from 0.5 microliter to 4 microliter. A pattern of one or more grooves 31600 and depressions 40800 may be formed on the interior wall surface 41000 of the tubule 41200 and may interconnect to provide a network of micro-cups interconnected by micro-fluidic flow channels 30600, as best illustrated in FIG. 33B. Such a network may be used to perform a variety of processing steps within one or more micro-cups and may permit the transport of small, precise volumes of sample and reagent between the micro-cups via micro-fluid flow channels by selectively compressing the tubule 41200. The network of grooves and depressions may be formed using semi-conductor processing techniques. For example, a mask pattern may be applied to an interior wall surface of the tubule 1200 using conventional photolithographic techniques. The grooves and depressions may then be formed by etching or otherwise removing portions of the interior wall surface based on the pattern imaged onto the interior wall surface. It may be desirable to form the network of grooves and depressions on a planar substrate 41800A constructed of a material suitable for use in the tubule 41200, as illustrated in FIGS. 33A and 33B. A second layer 41800B of material can be attached to the planar substrate 41800A to form the wall 41800 of the tubule 41200.

Referring to FIGS. 33A and 33B, one or more sample or reagent processing devices 41400 may be provided on the interior wall surface 41000 of the tubule 41200. For example, a microarray device may be embedded on the interior wall surface 41000 of the tubule 41200. An exemplary microarray device 41400 may comprise a plurality of reagent coated zones for simultaneous analysis of a plurality of analytes within a sample. The processing device 41400 may also be a micro-fluid device or a lab-on-a-chip device, or any other device for processing a sample. The processing device 41400 may be interconnected with one or more depressions 40800 or other processing devices via flow channels 30600. Any number of processing devices of any type may be provided in the tubule 41200.

Figure 37:
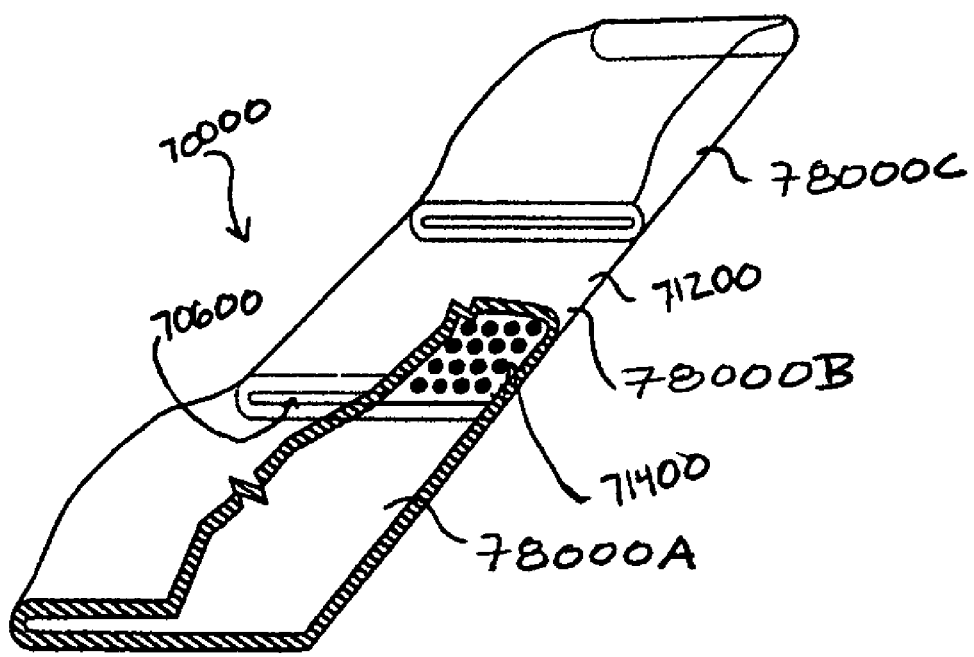
FIG. 37 is a perspective view of another exemplary embodiment of a sample vessel, illustrating the sample vessel with a portion of the wall removed to show a microarray on an interior surface of the wall of the sample vessel.

Referring to FIG. 37, a sample vessel 70000 comprising a tubule 71200 divided into multiple segments 78000A-C. Segment 78000B may be constructed of a rigid, generally non-flexible material and may have a processing device, such as a microarray 71400, embedded on the interior wall thereof. The segment 78000B may provide a pre-formed flow channel between two compressible segments 78000A and 78000C. By alternately compressing the two flexible segments 70800A and 78000C, the sample may flow through the flow channel 70600 to facilitate high efficient hybridization or binding of analytes to the reagent spots of the microarray 71400. A flow channel 706 having a small gap may also increase wash efficiency as a laminar flow is formed.

FIGS. 35A-35E illustrates an exemplary embodiment of a sample vessel 1000 comprising a tubule 1200 and an adapter 50000 that is connected to the tubule 1200 of the sample vessel 1000. The adapter 50000 may be provided to facilitate handling of the sample vessel 1000 and/or to facilitate connection of the tubule 1200 to an external device, such as a micro-fluid device, a lab-on-a-chip device, a microarray device, a reagent source, another sample vessel, or any other device suitable for containing or processing a sample. In the illustrated embodiments, the adapter 50000 is a generally planar tab that is coextensive with the tubule 1200. One skilled in the art will appreciate that the adapter 50000 need not be coextensive with the tubule and may be constructed of varying sizes and shapes depending upon the application. Moreover, more than one adapter may be provided.

The adapter 50000 may be constructed of any material suitable for use in construction the tubule 1200. For example, the adapter may be constructed of polyurethane. The adapter 50000 may be constructed of the same or a different material than the tubule 1200. To facilitate handling, the adapter 50000 may be constructed of a material having increased rigidity compared to the material of the tubule 1200, for example a high durometer polyurethane. In certain embodiments, the adapter 50000 may be manufactured with the tubule 1200 in, for example, a co-extrusion process or an injection molding process. Alternatively, the adapter 50000 may be manufactured independently and attached to the tubule 1200 in a post-forming process by, for example, bonding.

The exemplary embodiment of FIGS. 35A-35E also includes a container 2000 and an interface 3000, as described above. The container 2000 removably and replaceably encloses the tubule 1200 to protect the sample tubule 1200 and when removed, may allow direct manipulation of tubule 1200. A portion of adapter 50000 may not be enclosed by container 2000. The exposed portion of the adapter 50000 can be directly accessed by a user for labeling, handling and other processing. The interface 3000 includes an interface channel 3700 that communicates with an opening in the tubule 1200 to facilitate delivery of a sample to the tubule 1200. In the illustrated embodiment, a removable and replaceable cover 58600 is provided to selectively open and close the interface channel 3700. The exemplary cover 58600 includes a sample collection instrument in the form of a tissue swab 584 for collecting tissue samples from a sample source.

Figure 35A:
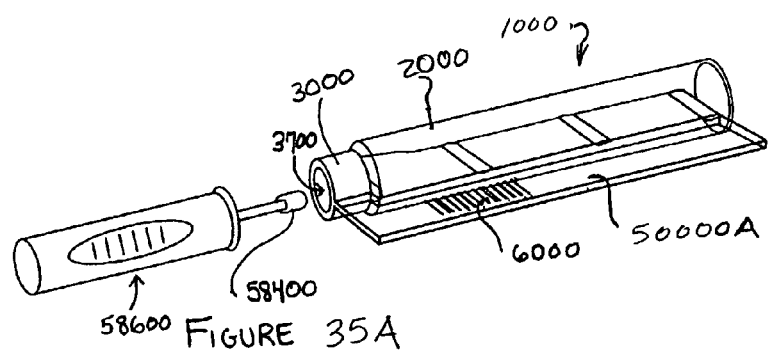
FIG. 35A is a perspective view of an exemplary embodiment of a sample vessel having an adapter for facilitating handling of the sample vessel and/or connecting of the sample vessel to an external device.
Figure 35B:
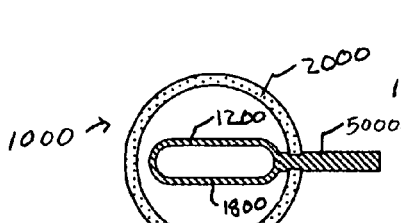
FIGS. 35B-35E are side elevational views in cross-section of a plurality of exemplary embodiments of an adapter connected to the sample vessel illustrated in FIG. 35A.

FIGS. 35A-B illustrate an embodiment of the adapter 50000 that is constructed to facilitate handling of the sample vessel 1000.

Figure 35C:
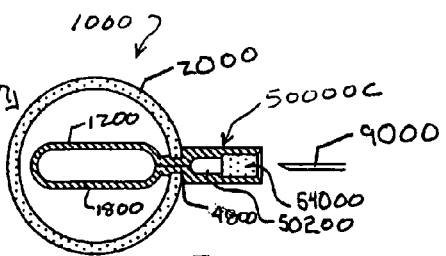

FIG. 35C illustrates an embodiment of the adapter 50000C that is designed to facilitate delivery of a reagent or a sample from an external device, such as a needle 9000 from a reagent injector cartridge. The adapter 50000C includes a reversible or irreversible pressure gate 4800 that provides a fluid channel to permit selective displacement of a fluid, e.g., a sample or reagent, between the tubule 1200 and the external device, in the present embodiment, needle 9000. The adapter 50000C may include a self-sealing membrane 54000, valve, or other sealing mechanism to facilitate selective communication with the external device. A reservoir 50200 may be provide to contain a fluid delivered from the external device or fluid from the tubule 1200. In use, the needle 9000 may penetrate the self-sealing membrane 54000 to deliver fluid to the reservoir 50200 or to withdraw fluid from the reservoir 50200. Pressure gate 4800 may be opened in the manner described above, e.g. by compressing the tubule 1200 or the reservoir 50200, to withdraw fluid from the reservoir 50200 or to deliver fluid to the reservoir 50200 from the tubule 1200. The needle 9000 may be coupled with a sensor, such as an electrode, a fiber optical sensor, for penetrating the self sealing membrane 54000 and measuring a sample property.

Figure 35D:
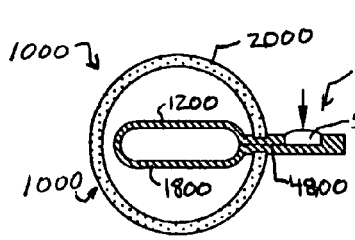

FIG. 35D illustrates an embodiment of the adapter 50000D that comprises a compressible reservoir 50600 and a reversible or irreversible pressure gate 4800 that provides a fluid channel to permit selective displacement of a fluid, e.g., a sample or reagent, to the tubule 1200 from the compressible reservoir 50600. The compressible reservoir 50600 may contain a pre-packed reagent. In certain embodiments, the compressible reservoir 50600 may be a blister pack. Upon compression of the compressible reservoir 50600, pressure gate 4800 may open and fluid with the compressible reservoir 50600 can be displaced in to the tubule 1200.

Figure 35E:
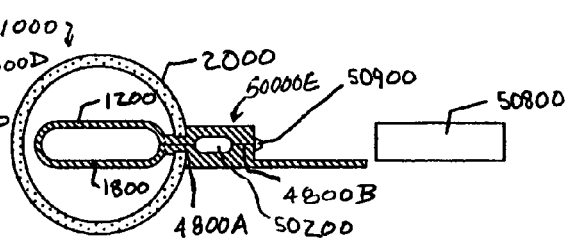

FIG. 35E illustrates an embodiment of the adapter 50000E that comprises a reservoir 50200, a first reversible or irreversible pressure gate 4800A that provides a fluid channel to permit selective displacement of a fluid, e.g., a sample or reagent, between the tubule 1200 and the reservoir 50200, and a second reversible or irreversible pressure gate 4800B that provides a fluid channel to permit selective displacement of a fluid, e.g., a sample or reagent, between an external device 50800 and the reservoir 50200. A connector 50900 may be provided to interface with the external device 50800. Such device may be an Access™ card for Micronics Inc., a LabChip® product from Caliper, Inc. or a GeneChip® from Affymetrix, Inc.

FIGS. 36A-E illustrate another exemplary embodiment of a sample vessel 60000 that comprises a tubule 1000 and an apparatus 60200 for drawing a sample into the tubule 1200 of the sample vessel 1000. The apparatus 60200 includes a cylindrical housing 60400 having an opening 60600 for receiving the tubule 1200. The opening 60200 extends from a proximal end 60800 to a distal end 61000 of the housing 60400. Both the housing 60400 and the opening 60600 can be sized and shaped to accommodate the size and shape of the tubule 1200 or other sample vessels. For example, the housing 60400 and opening 60600 are cylindrical in shape and have a circular cross-section analogous to that of the tubule 1200. The adapter 60000 comprises first means 61200 for compressing a first portion of the tubule 1200 and second means 61400 for compressing a second portion of the tubule 1200. The first compression means 61200 may be spaced apart from the second compression means 61400. For example, the first compression means 61200 may be positioned at the proximal end 60800 of the housing 60200 and the second compression means 61400 may be positioned at the distal end 61000 of the housing 60200. The spacing between the first and second compression means may be selected based on the desired sample collection volume in the tubule 1200.

The first compression means 61200 may comprise a first pair of spaced apart rollers, 61600A and 61600B. At least one of the rollers 61600A-B may be selectively movable into contact with the other roller to compress the tubule 1200 between the rollers 61600A-B. A first activator 62000 may be coupled to the rollers 61600A, 61600B to effect separation or compression of the rollers. The second compression means 61200 may comprise a second pair of spaced apart rollers, 61800A and 61800B. At least one of the rollers 61800A-B may be selectively movable into contact with the other roller to compress the tubule 1200 between the rollers 61800A-B. A second activator 62200 may be coupled to the rollers 61800A, 61800B to effect separation or compression of the rollers. In addition to rollers, or other compression mechanisms may be employed for the first and second compression means, including the compression members described above. Any structure suitable for selective compression of the tubule 1200 may be employed. The first and second compression means need not be the same structure.

In use, the tubule 1200 is inserted into the opening 60600 at the proximal end 60800 of the housing 60400 and drawn completely through the opening 60600 to the distal end 61000 of the housing 60400. As the tubule 1200 is drawn through the housing 60400, the tubule 1200 is flatten and compressed, as illustrated in FIG. 36B, to evacuate the tubule 1200. At the time of sample collection, a cover 68600 may be removed to expose a sample collection instrument, such as a needle 68400, that is in fluid connection with the tubule 1200. The needle 68400 can be inserted into the sample source and the first compression means 61200 may be separated to draw the sample into the tubule 1200, as illustrated in FIG. 36C. The sample vessel 1000 may then be inserted into a device 63000 for removing the needle 68400, or other sample collection instrument, as illustrated in FIG. 36D. The device 63000 may also include a mechanism for sealing the proximal end of the tubule 1200 after the needle 68400 is removed, by, for example, compressing and heating the wall of the tubule 1200 at the proximal end to bond or fuse the walls together. The second compression means 61400 may separate and the adapter 60000 may be removed from the tubule 1200, as illustrated in FIG. 36E.

While the sample vessels disclosed herein have been particularly shown and described with references to exemplary embodiments thereof, it will be understood by those skilled in the art that various changes in form and details may be made therein without departing from the spirit and scope of the disclosure. Those skilled in the art will recognize or be able to ascertain using no more than routine experimentation, many equivalents to the exemplary embodiments described specifically herein. Such equivalents are intended to be encompassed in the scope of the present disclosure.

The invention claimed is:

1. A temperature cycling apparatus for repeatedly heating and cooling a reaction mixture, the system comprising:
   a first heater translatable between a first orientation in which the first heater affects the temperature of the reaction mixture and a second orientation in which the first heater does not substantially affect the temperature of the reaction mixture, and a first prime mover for moving the first heater between the first heater's first and second orientations,
   a second heater adjacent the first heater, the second heater translatable between a first orientation in which the second heater affects the temperature of the reaction mixture and a second orientation in which the second heater does not substantially affect the temperature of the reaction mixture, and a second prime mover for moving the second heater between the second heater's first and second orientations,
   the second heater being in the second orientation when the first heater is in the first orientation, and the second heater being in the first orientation when the first heater is in the second orientation during temperature cycling.

2. The apparatus of claim 1, wherein the first prime mover includes a first stepper motor coupled to the first heater to move the first heater between the first heater's first and second orientations, and the second prime mover includes a second stepper motor coupled to the second heater to move the second heater between the second heater's first and second orientations.

3. The apparatus of claim 1, wherein the first heater includes a first heater element and a second heater element spaced apart from the first heater element and coupled to the first prime mover, and wherein the second heater includes a first heater element and a second heater element spaced apart from the first heater element and coupled to the second prime mover.

4. The apparatus of claim 3, wherein the first prime mover includes a first stepper motor and the second prime mover includes a second stepper motor.

5. The apparatus of claim 3, wherein the first prime mover includes a first bladder and the second prime mover includes a second bladder.

6. The apparatus of claim 5, wherein the first and second heater elements are electronic heat elements.

7. A temperature cycling system for repeatedly heating and cooling a reaction mixture, the system comprising:
   a flexible reaction vessel configured to contain the reaction mixture therein, the reaction vessel including a body having first and second portions coupled together,
   a first heater translatable between a first orientation in which the first heater affects the temperature of the first portion and a second orientation in which the first heater does not substantially affect the temperature of the first portion, and
   a second heater translatable between a first orientation in which the second heater affects the temperature of reaction mixture in the second portion and a second orientation in which the second heater does not substantially affect the temperature of reaction mixture in the second portion.

8. The system of claim 7, wherein the vessel further includes a cap coupled to the body and a sample area within the cap normally separated from the body by a seal.

9. The system of claim 7, wherein the first heater includes two heater elements and the second heater includes two heater elements, and wherein the vessel is positioned between the heater elements of each heater.

10. The system of claim 9, wherein one of the heater elements of each of the first and second heaters is stationary and the other heater element of each of the first and second heaters is movable.

11. The system of claim 10, further including a first motor coupled the movable heater element of the first heater and a second motor coupled to the movable heater element of the second heater.

12. The system of claim 11, wherein each of the first and second motors are stepper motors.

13. The system of claim 9, wherein each heater element includes a temperature sensor.

14. The system of claim 7, further including a first prime mover for moving the first heater between the first heater's first and second orientations and a second prime mover for moving the second heater between the second heater's first and second orientations.

15. The system of claim 14, wherein the first and second prime movers each include a stepper motor.

16. The system of claim 15, wherein the first heater includes a stationary heater element and a movable heater element spaced-apart from the stationary heater element and coupled to the first prime mover, and wherein the second heater includes a stationary heater element and a movable heater element spaced-apart from the stationary heater element and coupled to the second prime mover.

17. The system of claim 7, wherein the first heater is configured such that when the first heater is moved from the first orientation to the second orientation, the first heater forces the reaction mixture into the second portion of the reaction vessel, and wherein the second heater is configured such that when the second heater is moved from the first orientation to the second orientation, the second heater forces the reaction mixture into the first portion of the reaction vessel.

18. A method for thermal cycling a fluid sample, the sample provided in a flexible reaction vessel comprising a first region and a second region adjacent to and in fluid communication with the first region, comprising:
   a. compressing the second region to force the sample into the first region and into contact with a first pair of heaters at a first temperature, and
   b. subsequently compressing the first region to force the sample into the second region and into contact with a second pair of heaters at a second temperature, the second temperature being different from the first temperature.

19. The method of claim 18 further comprising repeating steps a and b throughout a plurality of temperature cycles.

20. A method for amplifying a nucleic acid in a biological sample comprising:
   a. placing the biological sample into a flexible reaction vessel comprising a first region and a second region adjacent to and in fluid communication with the first region,
   b. compressing the first region to force the sample into the second region and into contact with a pair of denaturation heaters at a denaturation temperature,
   c. compressing the second region to force the sample into the first region and into contact with a pair of annealing heaters at an annealing temperature, and
   d. repeating steps b and c for a plurality of amplification cycles.

21. The method of claim 20 wherein the nucleic acid is amplified by PCR and the sample vessel further comprises therein reagents for performing PCR.

22. The method of claim 21 wherein the reagents include a polymerase and primers.

23. The method of claim 22 wherein the reaction vessel further comprises a fluorescent entity therein, the fluorescent entity capable of providing a fluorescent signal related to the quantity of the nucleic acid.

24. The method of claim 23 further comprising monitoring the fluorescent signal during each of the amplification cycles.

25. The method of claim 24 wherein the vessel further comprises an end adjacent to the second region and the monitoring step further comprises measuring the fluorescent signal at a plurality of points along the end to obtain a plurality of data points for each amplification cycle.

26. The method of claim 20, wherein the flexible reaction vessel comprises a plurality of individual reaction vessels arranged to form a row of reaction vessels,
   the method further comprising simultaneously amplifying a plurality of additional nucleic acids in a plurality of additional biological samples wherein step (a) comprises placing each respective additional biological sample in its respective individual reaction vessel.

27. A method for repeatedly heating and cooling a reaction mixture contained within a flexible reaction vessel comprising:
   placing the reaction vessel adjacent a first heater and a second heater,
   heating the first heater to a first temperature,
   heating the second heater to a second temperature, alternately opening and closing the first and second heaters so that the reaction mixture is in thermal contact with the respective heater when the heater is in the opened position and the reaction mixture is not in thermal contact with the respective heater when the heater is in the closed position.

28. The method of claim 27, wherein opening and closing includes moving the first heater to a closed position to move substantially all of the reaction mixture to a position adjacent the second heater, heating the reaction mixture to the second temperature, moving the first pair of heaters to an opened position and moving the second pair of heaters to a closed position to move substantially all of the reaction mixture to a position adjacent the first pair of heaters, and heating the reaction mixture to the first temperature.

29. A method for heating and cooling a reaction mixture contained within a flexible reaction vessel comprising:
heating a first pair of heaters positioned in a first zone to a first temperature,
heating a second pair of heaters positioned in a second zone to a second temperature,
placing the reaction vessel between each of the first and second pair of heaters so that the first heater engages a first portion of the reaction vessel and the second heater engages a second portion of the reaction vessel, and
moving the reaction mixture between the first zone in thermal contact with the first pair of heaters and the second zone in thermal contact with the second pair of heaters by alternately opening and closing the first and second pairs of heaters around the reaction vessel.

30. A device for thermal cycling a sample provided in a flexible vessel, comprising
a first heating element for heating the sample to a first temperature, the first heating element repeatably movable between an open position and a closed position, the first heating element defining a first gap for receiving a first portion of the flexible vessel,
a second heating element for heating the sample to a second temperature, the second heating element repeatably movable between an open position and a closed position, the second heating element defining a second gap contiguous with the first gap, the second gap for receiving a second portion of the flexible vessel, wherein when the first heating element is in the closed position, the sample is forced from the first portion of the flexible vessel, and when the second heating element is in the closed position, the sample is forced from the second portion of the flexible vessel.

31. The device of claim 30, wherein during thermal cycling when the first heating element is in the closed position, the second heating element is in the open position and the sample is forced into the second portion of the sample vessel and when the second heating element is in the closed position, the first heating element is in the open position and the sample is forced into the first portion of the sample vessel.

32. The device of claim 30, further comprising a third heating element for heating the sample to a third temperature, the third heating element repeatably movable between an open position and a closed position, the third heating element defining a third gap for receiving a third portion of the flexible vessel, wherein when the third heating element is in the closed position, the sample is forced from the third portion of the flexible vessel.

33. The device of claim 32, wherein the fluorimeter is positioned to measure fluorescence in the second portion of the flexible vessel and wherein the first temperature is higher than the second temperature.

34. The device of claim 30, further comprising a fluorimeter positioned to measure fluorescence in the reaction vessel.

35. The device of claim 30, wherein the first and second gaps are configured for receiving a plurality of flexible vessels, each of the plurality of flexible vessels having a first portion and a second portion.

36. The device of claim 35, wherein the plurality of reaction vessels received within the first and second gaps are in a parallel arrangement.

37. The device of claim 36, wherein the plurality of flexible reaction vessels are arranged to form a row.

38. The device of claim 30, wherein the first heating element comprises a first stationary heating element, a first movable heating element, and a means for moving the first movable heating element from the open position toward the first stationary heating element and to the closed position.

39. The device of claim 38, wherein the second heating element comprises a second stationary heating element, a second movable heating element, and a means for moving the second movable heating element, from the open position toward the second stationary heating element and to the closed position.

40. The device of claim 30, further comprising a pneumatic system, and wherein the first heating element comprises a first stationary heating element and a first movable heating element coupled to the pneumatic system to move the first movable heating element toward the first stationary heating element, and wherein the second heating element comprises a second stationary heating element and a second movable heating element coupled to the pneumatic system to move the second movable heating element toward the second stationary heating element.

41. A thermal cycling device for repeatedly heating and cooling a reaction mixture, the device comprising:
a first energy transfer element translatable between a first orientation in which the first energy transfer element affects the temperature of the reaction mixture and a second orientation in which the first energy transfer element does not substantially affect the temperature of the reaction mixture, and a first driver for moving the first energy transfer element between the first energy transfer element's first and second orientations,
a second energy transfer element adjacent the first energy transfer element, the second energy transfer element translatable between a first orientation in which the second energy transfer element affects the temperature of the reaction mixture and a second orientation in which the second energy transfer element does not substantially affect the temperature of the reaction mixture, and a second driver for moving the second energy transfer element between the second energy transfer element's first and second orientations,
the second energy transfer element being in the second orientation when the first energy transfer element is in the first orientation, and the second energy transfer element being in the first orientation when the first energy transfer element is in the second orientation during temperature cycling.

42. The device of claim 41, wherein the first driver includes a first stepper motor coupled to the first energy transfer element to move the first energy transfer element between the first energy transfer element's first and second orientations, and the second driver includes a second stepper motor coupled to the second energy transfer element to move the second energy transfer element between the second energy transfer element's first and second orientations.

43. The device of claim 41, further comprising a third energy transfer element spaced apart from the first energy transfer element to define a first gap, and further comprising a fourth energy transfer element spaced apart from the second energy transfer element to define a second gap.

44. The device of claim 43, wherein the first driver includes a first stepper motor and the second driver includes a second stepper motor.

45. The device of claim 43, further comprising a processor coupled to the drivers to control their moving speeds.

46. The device of claim 43, wherein the first driver is coupled to a first inflatable membrane and the second driver is coupled to a second inflatable membrane.

47. The device of claim 46, further comprising means for controlling the inflation of the inflatable membranes.

48. The device of claim 47, further comprising means for controlling the inflation of the inflatable membranes separately.

49. The device of claim 46, wherein the first and second inflatable membranes are movable in a floating motion to bias the respective first and second energy transfer elements back and forth.

50. The device of claim 43, wherein at least one heater element comprises a Kapton heater.

51. The device of claim 43, wherein at least one driver or energy transfer element comprises a curved, angular, or non-planar surface.

52. The device of claim 43, wherein the respective gap between the first and third energy transfer elements or between the second and fourth energy transfer elements in the first orientation is in the range of approximately 0.1 millimeters to 1.4 millimeters.

53. The device of claim 43, wherein the respective gap between the first and third energy transfer elements or between the second and fourth energy transfer elements in the second orientation is in the range of approximately 0.02 millimeters to 1 millimeter.

54. A thermal cycling device for repeatedly heating and cooling a reaction mixture, the device comprising:
a sample vessel configured to contain the reaction mixture therein, the sample vessel including a body having first and second segments coupled together,
a first energy transfer element translatable between a first orientation in which the first energy transfer element affects the temperature of reaction mixture in the first segment and a second orientation in which the first energy transfer element does not substantially affect the temperature of reaction mixture in the first segment,
a second energy transfer element translatable between a first orientation in which the second energy transfer element affects the temperature of reaction mixture in the second segment and a second orientation in which the second energy transfer element does not substantially affect the temperature of reaction mixture in the second segment.

55. The system of claim 54, wherein the sample vessel further includes an interface coupled to the body and a sample area within the interface normally separated from the body by a stopper or pressure gate.

56. The device of claim 54, further comprising third and fourth energy transfer elements, wherein the sample vessel is positioned between the first and third energy transfer elements and between the second and fourth energy transfer elements.

57. The device of claim 56, wherein one of the first and third energy transfer elements is stationary and the other is movable, and wherein one of the second and fourth energy transfer elements is stationary and the other is movable.

58. The device of claim 57, wherein one movable energy transfer element is coupled to a first inflatable membrane, and the other movable energy transfer element is coupled to a second inflatable membrane.

59. The system of claim 57, wherein a first motor is coupled to one movable energy transfer element, and a second motor is coupled to the other movable energy transfer element.

60. The device of claim 59, wherein each of the first and second motors are stepper motors.

61. The device of claim 56, wherein each energy transfer element includes a temperature sensor.

62. The device of claim 54, further including a first compression member for moving the first energy transfer element between the first energy transfer element's first and second orientations and a second compression member for moving the second energy transfer element between the second energy transfer element's first and second orientations.

63. The device of claim 62, wherein the first and second compression members each include a stepper motor.

64. The device of claim 63, further comprising third and fourth energy transfer elements, and wherein:
the first and third energy transfer elements are spaced-apart from one another;
one of the first and third energy transfer elements is stationary and the other is movable, the movable element being coupled to the first compression member;
the second and fourth energy transfer elements are spaced-apart from one another; and
one of the second and fourth energy transfer elements is stationary and the other is movable, the movable element being coupled to the second compression member.

65. The system of claim 54, wherein the first energy transfer element is configured such that when the first energy transfer element is moved from the first orientation to the second orientation, the first energy transfer element forces the reaction mixture into the second portion of the sample vessel, and wherein the second energy transfer element is configured such that when the second energy transfer element is moved from the first orientation to the second orientation, the second energy transfer element forces the reaction mixture into the first portion of the sample vessel.

66. A method for thermal cycling a fluid sample, the sample provided in a flexible sample vessel comprising a first segment and a second segment adjacent to and in fluid communication with the first segment, the method comprising:
a. compressing the second segment to force the sample into the first segment and into contact with a first pair of energy transfer elements at a first temperature; and
b. subsequently compressing the first segment to force the sample into the second segment and into contact with a second pair of energy transfer elements at a second temperature, the second temperature being different from the first temperature.

67. The method of claim 66 further comprising repeating steps a and b throughout a plurality of temperature cycles.

68. The method of claim 66 further comprising monitoring the fluorescent signal during each of the temperature cycles.

69. The method of claim 66, wherein the flexible reaction vessel comprises a plurality of individual reaction vessels arranged to form a row of reaction vessels,
the method further comprising simultaneously thermal cycling a plurality of samples in a plurality of reaction vessels wherein the first step comprises placing each respective additional sample in its respective individual reaction vessel.

70. A method for amplifying a nucleic acid in a biological sample, comprising:
- a. placing the biological sample into a flexible sample vessel comprising a first segment and a second segment adjacent to and in fluid communication with the first segment;
- b. compressing the first segment to force the sample into the second segment and into contact with a pair of denaturation energy transfer elements at a denaturation temperature;
- c. compressing the second segment to force the sample into the first segment and into contact with a pair of annealing energy transfer elements at an annealing temperature; and
- d. repeating steps b and c for a plurality of amplification cycles.

71. The method of claim 70 wherein the nucleic acid is amplified by polymerase chain reaction (PCR) and the sample vessel further comprises therein reagents for performing PCR.

72. The method of claim 71 wherein the reagents include a polymerase and primers.

73. The method of claim 70 wherein the sample vessel further comprises a fluorescent probe therein, the fluorescent probe capable of providing a fluorescent signal related to the quantity of the nucleic acid.

74. The method of claim 73 further comprising monitoring the fluorescent signal during each of the amplification cycles.

75. The method of claim 70 further comprising sensing a light signal emanating from the sample vessel using a charge coupled device.

76. The method of claim 75, further comprising analyzing the signal by signal processing.

77. A method for repeatedly heating and cooling a reaction mixture contained within a flexible sample vessel, the method comprising:
- placing the sample vessel adjacent a first energy transfer element and a second energy transfer element;
- heating the first energy transfer element to a first temperature;
- heating the second energy transfer element to a second temperature; and
- alternately opening and closing the first and second energy transfer elements so that the reaction mixture is in thermal contact with the respective energy transfer element when the energy transfer element is in the opened position and the reaction mixture is not in thermal contact with the respective energy transfer element when the energy transfer element is in the closed position.

78. The method of claim 77, wherein opening and closing includes moving the first energy transfer element to a closed position to move substantially all of the reaction mixture to a position adjacent the second energy transfer element, heating the reaction mixture to the second temperature, moving the first pair of energy transfer elements to an opened position and moving the second pair of energy transfer elements to a closed position to move substantially all of the reaction mixture to a position adjacent the first pair of energy transfer elements, and heating the reaction mixture to the first temperature.

79. A method for heating a reaction mixture contained within a flexible sample vessel, the method comprising:
- heating a first pair of energy transfer elements positioned in a first processing station to a first temperature;
- heating a second pair of energy transfer elements positioned in a second processing station to a second temperature;
- placing the sample vessel between each of the first and second pair of energy transfer elements so that the first energy transfer element engages a first segment of the sample vessel and the second energy transfer element engages a second segment of the sample vessel; and
- moving the reaction mixture between the first processing station in thermal contact with the first pair of energy transfer elements and the second processing station in thermal contact with the second pair of energy transfer elements by alternately opening and closing the first and second pairs of energy transfer elements around the sample vessel.

80. A device for thermal cycling a sample provided in a flexible sample vessel, comprising
- a first energy transfer element for heating or cooling the sample to a first temperature, the first energy transfer element repeatably movable between an open position and a closed position, the first energy transfer element defining a first gap for receiving a first segment of the flexible sample vessel,
- a second energy transfer element for heating or cooling the sample to a second temperature, the second energy transfer element repeatably movable between an open position and a closed position, the second energy transfer element defining a second gap contiguous with the first gap, the second gap for receiving a second segment of the flexible sample vessel, wherein when the first energy transfer element is in the closed position, the sample is forced from the first segment of the flexible sample vessel, and when the second energy transfer element is in the closed position, the sample is forced from the second segment of the flexible sample vessel.

81. The device of claim 80, wherein the device is configured so that during thermal cycling:
- when the first energy transfer element is in the closed position, the second energy transfer element is in the open position and the sample is forced into the second segment of the sample vessel; and
- when the second energy transfer element is in the closed position, the first energy transfer element is in the open position and the sample is forced into the first segment of the sample vessel.

82. The device of claim 80, further comprising a third energy transfer element for heating or cooling the sample to a third temperature, the third energy transfer element repeatably movable between an open position and a closed position, the third energy transfer element defining a third gap for receiving a third segment of the flexible sample vessel, wherein when the third energy transfer element is in the closed position, the sample is forced from the third segment of the flexible sample vessel.

83. The device of claim 80, further comprising a reaction sensor sensitive to fluorescent light and positioned to measure fluorescence in the sample vessel.

84. The device of claim 83, wherein the reaction sensor is positioned to measure fluorescence in the second segment of the sample vessel and wherein the first temperature is higher than the second temperature.

85. The device of claim 80, wherein each energy transfer element defines two or more gaps so that each energy transfer element is capable of receiving two or more sample vessels.

86. The device of claim 85, wherein the two or more sample vessels are received in their respective gaps in a parallel arrangement.

87. The device of claim 85, further comprising a reaction sensor sensitive to fluorescent light and positionable in a plurality of positions to measure fluorescence in the two or more sample vessels.

88. The device of claim 80, wherein the first energy transfer element comprises a first stationary element, a first movable element, and a means for moving the first movable element from the open position toward the first stationary element and to the closed position.

89. The device of claim 88, wherein the second energy transfer element comprises a second stationary element, a second movable element, and a means for moving the second movable element from the open position toward the second stationary element and to the closed position.

90. A temperature cycling system for repeatedly heating and cooling a reaction mixture contained within a flexible reaction vessel, the reaction vessel including a body having first and second portions coupled together, the system comprising:
- a first zone configured for receiving the first portion of the reaction vessel, the first zone comprising a first heater, the first zone movable between an open orientation in which the first heater affects the temperature of the reaction mixture contained within the first portion, and a closed orientation in which the reaction mixture is forced from the first portion and the first heater does not substantially affect the temperature of the reaction mixture, and
- a second zone configured for receiving the second portion of the reaction vessel, the second zone comprising a second heater, the second zone movable between an open orientation in which the second heater affects the temperature of the reaction mixture contained within the second portion, and a closed orientation in which the reaction mixture if forced from the second portion and the second heater does not substantially affect the temperature of the reaction mixture.

91. The temperature cycling system of claim 90 further comprising a processor for controlling movement of the first and second zones such that during temperature cycling the first zone is in the open orientation when the second zone is in the closed orientation and the first zone is in the closed orientation when the second zone is in the open orientation.

92. The temperature cycling system of claim 90 wherein the flexible reaction vessel comprises a plurality of individual reaction vessels arranged to form a row of reaction vessels, each individual reaction vessel including a body having a first and second portions coupled together, wherein
- the first zone is configured to receive a row of the first body portions, and
- the second zone is configured to receive a row of the second body portions.

93. The temperature cycling system of claim 90 wherein the second zone is set at a temperature different from that of the first zone.

94. A temperature cycling apparatus for repeatedly heating and cooling a reaction mixture, the system comprising:
- a first heater movable between a first orientation in which the first heater affects the temperature of the reaction mixture and a second orientation in which the first heater does not substantially affect the temperature of the reaction mixture, and a first prime mover, comprising a first bladder, for moving the first heater between the first heater's first and second orientations,
- a second heater adjacent the first heater, the second heater movable between a first orientation in which the second heater affects the temperature of the reaction mixture and a second orientation in which the second heater does not substantially affect the temperature of the reaction mixture, and a second prime mover, comprising a second bladder, for moving the second heater between the second heater's first and second orientations,
- the second heater being in the second orientation when the first heater is in the first orientation, and the second heater being in the first orientation when the first heater is in the second orientation during temperature cycling.

* * * * *